(12) United States Patent
Bonazzi et al.

(10) Patent No.: US 12,281,125 B2
(45) Date of Patent: Apr. 22, 2025

(54) RAPAMYCIN DERIVATIVES

(71) Applicant: NOVARTIS AG, Basel (CH)

(72) Inventors: Simone Bonazzi, Cambridge, MA (US); Michael Connolly, Salem, MA (US); David Jonathan Glass, Cortland Manor, NY (US); Manuel Mihalic, Grenzach-Wyhle (DE); Andrew W. Patterson, Somerville, MA (US); Silvio Roggo, Muttenz (CH); Tea Shavlakadze, Hawthorne, NY (US); Patrik Zueger, Basel (CH)

(73) Assignee: NOVARTIS AG, Basel (CH)

( * ) Notice: Subject to any disclaimer, the term of this patent is extended or adjusted under 35 U.S.C. 154(b) by 825 days.

(21) Appl. No.: 17/414,696

(22) PCT Filed: Dec. 17, 2019

(86) PCT No.: PCT/IB2019/060957
§ 371 (c)(1),
(2) Date: Jun. 16, 2021

(87) PCT Pub. No.: WO2020/128861
PCT Pub. Date: Jun. 25, 2020

(65) Prior Publication Data
US 2022/0064185 A1    Mar. 3, 2022

Related U.S. Application Data

(60) Provisional application No. 62/781,242, filed on Dec. 18, 2018.

(51) Int. Cl.
C07D 498/18 (2006.01)
A61K 31/436 (2006.01)
A61K 45/06 (2006.01)

(52) U.S. Cl.
CPC .......... *C07D 498/18* (2013.01); *A61K 31/436* (2013.01); *A61K 45/06* (2013.01)

(58) Field of Classification Search
CPC .... C07D 498/18; A61K 31/436; A61K 45/06; A61K 31/439; A61P 1/16; A61P 13/12; A61P 35/00; A61P 43/00
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit |
| 4,650,803 A | 3/1987 | Stella et al. |
| 5,120,842 A | 6/1992 | Failli et al. |
| 5,151,413 A | 9/1992 | Caufield et al. |
| 5,258,389 A | 11/1993 | Goulet et al. |
| 5,362,718 A | 11/1994 | Skotnicki et al. |
| 5,527,907 A | 6/1996 | Or et al. |
| 5,665,772 A | 9/1997 | Cottens et al. |
| 5,985,890 A | 11/1999 | Cottens et al. |
| 6,384,046 B1 | 5/2002 | Schuler et al. |
| 8,906,374 B2 | 12/2014 | Kim et al. |
| 9,358,236 B2 | 6/2016 | Murphy et al. |
| 9,427,463 B2 | 8/2016 | Kim et al. |
| 9,669,032 B2 | 6/2017 | Liu et al. |
| 9,683,048 B2 | 6/2017 | Freeman et al. |

(Continued)

FOREIGN PATENT DOCUMENTS

| | | |
|---|---|---|
| CN | 101389337 A | 3/2009 |
| EA | 011488 B1 | 4/2009 |

(Continued)

OTHER PUBLICATIONS

Extended European Search Report and Written Opinion received for European Patent Application No. 24150040.4 mailed on Jun. 11, 2024, 9 pages.

(Continued)

*Primary Examiner* — Rayna Rodriguez
(74) *Attorney, Agent, or Firm* — Morrison & Foerster LLP

(57) ABSTRACT

The disclosure provides 32-deoxo-rapamycin derivatives of Formula (I), or a pharmaceutically acceptable salt thereof, pharmaceutical compositions and pharmaceutical combinations comprising a compound of Formula (I), and methods of making same. Also provided herein are methods of using a compound of Formula (I) or a pharmaceutically acceptable salt thereof for treating the diseases and disorders described herein.

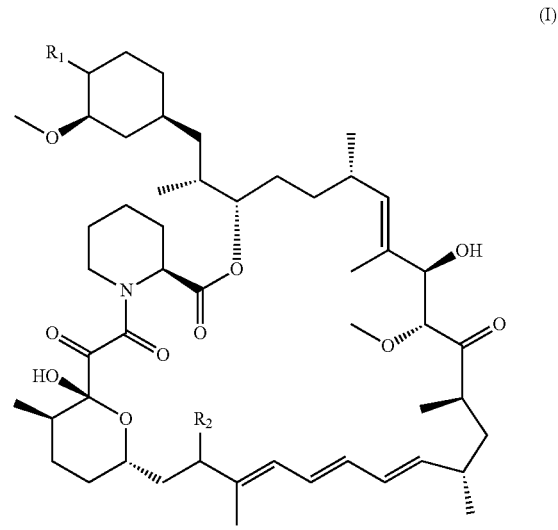

(I)

14 Claims, 10 Drawing Sheets

(56) References Cited

U.S. PATENT DOCUMENTS

| | | | |
|---|---|---|---|
| 10,800,793 | B2 | 10/2020 | Bonazzi et al. |
| 12,091,424 | B2 | 9/2024 | Bonazzi et al. |
| 2020/0392159 | A1 | 12/2020 | Bonazzi et al. |
| 2022/0202787 | A1 | 6/2022 | Bonazzi et al. |
| 2022/0242878 | A1 | 8/2022 | Bonazzi et al. |

FOREIGN PATENT DOCUMENTS

| | | |
|---|---|---|
| EP | 1212331 B1 | 4/2004 |
| JP | H07509246 A | 10/1995 |
| JP | 2000510815 A | 8/2000 |
| JP | 2002508971 A | 3/2002 |
| JP | 2002514165 A | 5/2002 |
| JP | 2002514893 A | 5/2002 |
| JP | 2009527520 A | 7/2009 |
| KR | 19990022780 A | 3/1999 |
| RU | 2126409 C2 | 2/1999 |
| RU | 2325906 C2 | 6/2008 |
| WO | WO-1994002136 A1 | 2/1994 |
| WO | WO-1996041807 A1 | 12/1996 |
| WO | WO-1996041865 A1 | 12/1996 |
| WO | WO-1997035575 A1 | 10/1997 |
| WO | WO-1999036553 A2 | 7/1999 |
| WO | WO-2001014387 A1 | 3/2001 |
| WO | WO-2008022256 A2 | 2/2006 |
| WO | WO-2007085400 A1 | 8/2007 |
| WO | WO-2007096174 A1 | 8/2007 |
| WO | WO-2012103959 A1 | 8/2012 |
| WO | WO-2016207205 A1 | 12/2016 |
| WO | WO-2017044720 A1 | 3/2017 |
| WO | WO-2018204416 A1 | 11/2018 |

OTHER PUBLICATIONS

Bae-Jump et al., (2010). "Rapamycin inhibits cell proliferation in type I and type II endometrial carcinomas: a search for biomarkers of sensitivity to treatment," Gynecol Oncol, 119(3):579-585, 18 pages.

Baker et al., (2016). "Naturally occurring p16(Ink4a)-positive cells shorten healthy lifespan", Nature, 530(7589):184-203, 30 pages.

Baraz et al., (2014). "mTOR inhibition by everolimus in childhood acute lymphoblastic leukemia induces caspase-independent cell death," PLoS One, 9(7):e102494.

Battelli et al., (2011). "mTOR inhibitors in renal cell carcinoma," Therapy, 8(4):359-367, 14 pages.

Bayle et al., (2006). "Rapamycin Analogs with Differential Binding Specificity Permit Orthogonal Control of Protein Activity," Chemistry and Biology, 13(1):99-107.

Buss et al., (2009). "Beneficial Effects of Mammalian Target of Rapamycin Inhibition on Left Ventricular Remodeling After Myocardial Infarction", Journal of American College of Cardiology, 54(25):2435-2446.

Buss et al., (2010). "Augmentation of autophagy by mTOR-inhibition in myocardial infarction: When size matters", Autophagy, 6(2):304-306.

Cai et al., (2013). "mTOR inhibitor RAD001 (everolimus) induces apoptotic, not autophagic cell death, in human nasopharyngeal carcinoma cells," Int J Mol Med, 31(4):904-912.

Cassano et al., (2019). "Early intrathecal infusion of everolimus restores cognitive function and mood in a murine model of Alzheimer's disease," Exp Neurol, 311:88-105.

Chang et al., (2017). "Regression of Neonatal Cardiac Rhabdomyoma in Two Months Through Low-Dose Everolimus Therapy: A Report of Three Cases," Pediatr Cardiol, 38(7):1478-1484.

Chinnery (2015). "Mitochondrial disease in adults: what's old and what's new", EMBO Molecular Medicine, 7(2):1503-1512.

Ciołczyk-Wierzbicka et al., (2020). "mTOR inhibitor everolimus reduces invasiveness of melanoma cells," Hum Cell, 33(1):88-97.

Cuppens et al., (2017). "Potential Targets Analysis Reveals Dual PI3K/mTOR Pathway Inhibition as a Promising Therapeutic Strategy for Uterine Leiomyosarcomas—an Enitec Group Initiative," Clin Cancer Res, 23(5):1274-1285.

Doi et al., (2010). "Multicenter phase II study of everolimus in patients with previously treated metastatic gastric cancer," J Clin Oncol, 28(11):1904-1910.

Ehninger et al., (2008). "Reversal of learning deficits in a Tsc2+/− mouse model of tuberous sclerosis", Nature Medicine, 14(8):843-848, 15 pages.

Elnaggar et al., (2016). "Addition of Everolimus Post VEGFR Inhibition Treatment Failure in Advanced Sarcoma Patients Who Previously Benefited from VEGFR Inhibition: A Case Series," PLoS One, 11(6):e0156985, 7 pages.

Fanoudi et al., (2018). "Everolimus, a mammalian target of rapamycin inhibitor, ameliorated streptozotocin-induced learning and memory deficits via neurochemical alterations in male rats," Excli J, 17:999-1017.

Ghidini et al., (2017). "Clinical development of mTor inhibitors for renal cancer," Expert Opin. Investig. Drugs, 26:1229-1237.

Guenther et al., (2009). "Phase I/II Study with Single Agent Everolimus (RAD001) in Patients with Relapsed or Refractory Multiple myeloma," Blood, 114(22):3850, 2 pages.

Gulhati et al., (2012). "Sorafenib enhances the therapeutic efficacy of rapamycin in colorectal cancers harboring oncogenic KRAS and PIK3CA," Carcinogenesis, 33(9):1782-1790.

Günther et al., (2015). "Activity of everolimus (RAD001) in relapsed and/or refractory multiple myeloma: a phase I study," Haematologica, 100(4):541-547.

Guo et al., (2016). "Everolimus exhibits anti-tumorigenic activity in obesity-induced ovarian cancer," Oncotarget, 7(15):20338-20356.

Harrison et al., (2009). "Rapamycin fed late in life extends lifespan in genetically heterogeneous mice", Nature, 460(7253):392-396, 11 pages.

Holmes (2007). "Tuberous Sclerosis Complex and Epilepsy: Recent Developments and Future Challenges," Epilepsia, 48(4):617-630.

Hujber et al., (2017). "Rapamycin (mTORC1 inhibitor) reduces the production of lactate and 2-hydroxyglutarate oncometabolites in IDH1 mutant fibrosarcoma cells," J Exp Clin Cancer Res, 36(1):74, 12 pages.

International Search Report and Written Opinion received for International Patent Application No. PCT/IB2018/057422 mailed on Jan. 3, 2019, 10 pages.

International Search Report and Written Opinion received for International Patent Application No. PCT/IB2019/060957 mailed on Mar. 19, 2020, 10 pages.

International Search Report and Written Opinion received for International Patent Application No. PCT/IB2020/052825 mailed on May 28, 2020, 11 pages.

Johnston et al., (2018). "Phase 2 study of everolimus for relapsed or refractory classical Hodgkin lymphoma," Exp Hematol Oncol., 7:12, 10 pages.

Kabat et al., (2012). "Focal cortical dysplasia—review," Pol. J Radial., 77(2):35-43.

Kaeberlein et al., (2005). "Regulation of Yeast Replicative Life Span by TOR and Sch9 in Response to Nutrients," Science, 310(5751):1193-1196.

Kaeberlein et al., (2019). "Rapamycin and Alzheimer's disease: Time for a clinical trial?" Sci Transl Med, 11(476):aar4289, 10 pages.

Kang et al., (2021). "Impact of everolimus on survival after liver transplantation for hepatocellular carcinoma," Clin Mol Hepatol, 27(4):589-602.

Kapahi et al., (2004). "Regulation of Lifespan in Drosophila by Modulation of Genes in the TOR Signaling Pathway," Current Biology, 14:885-890, 8 pages.

Khan et al., {2017). "mTORC1 Regulates Mitochondrial Integrated Stress Response and Mitochondrial Myopathy Progression," Cell Metabolism, 26:419-428, 16 pages.

Koopman et al., {2016). "Mitochondrial disorders in children: toward development of small-molecule treatment strategies," EMBO Molecular Medicine, 8(4):311-327.

Kümmerer (2010). "Pharmaceuticals in the environment," Annual Review of Environment and Resources, 35:57-75.

(56) References Cited

OTHER PUBLICATIONS

Kwitkowski et al., (2010). "FDA Approval Summary: Temsirolimus as Treatment for Advanced Renal Cell Carcinoma," The Oncologist, 15(4):428-435.
Laplante et al., (2012). "mTOR Signaling in Growth Control and Disease," Cell, 149(2):274-293.
Lee et al., (2007). "mTOR Pathway as a Target in Tissue Hypertrophy," Ann. Rev. Pharmacol. Toxicol., 47:7.1-7.25.
Lin et al., (2017). "Rapamycin rescues vascular, metabolic and learning deficits in apolipoprotein E4 transgenic mice with pre-symptomatic Alzheimer's disease," J Cereb Blood Flow Metab, 37(1):217-226.
Ljungberg et al., (2009). "Rapamycin suppresses seizures and neuronal hypertrophy in a mouse model of cortical dysplasia," Dis Model Mech., 2(7-8):389-398.
Luengo et al., (1995). "Structure-Activity Studies of Rapamycin Analogs: Evidence That The C-7 Methoxy Group Is Part of The Effector Domain and Positioned at The Fkbp12-Frap Interface," Chemistry and Biology, 2(7):471-481.
Mabuchi et al., (2009). "mTOR is a promising therapeutic target both in cisplatin-sensitive and cisplatin-resistant clear cell carcinoma of the ovary," Clin Cancer Res, 15(17):5404-5413, 21 pages.
Mannick et al., (2014). "mTOR inhibition improves immune function in the elderly," Science Translational Medicine, 6(268), 12 pages.
Manning et al., (2002). "Identification of the Tuberous Sclerosis Complex-2 Tumor Suppressor Gene Product Tuberin as a Target of the Phosphoinositide 3-Kinase/Akt Pathway," Molecular Cell, 10:151-162.
Martin et al., (2012). "Effectiveness and molecular interactions of the clinically active mTORC1 inhibitor everolimus in combination with tamoxifen or letrozole in vitro and in vivo," Breast Cancer Res, 14(5):R132, 15 pages.
Marz et al., (2013). "Large FK506-Binding Proteins Shape the Pharmacology of Rapamycin," Molecular and Cellular Biology, 33(7):1357-1367.
McAlpine et al., (1991). "Revised NMR assignments for rapamycin," J. Antibiot. (Tokyo) 44:688-690.
Meikle et al., (2008). "Response of a Neuronal Model of Tuberous Sclerosis to Mammalian Target of Rapamycin (mTOR) Inhibitors: Effects on mTORC1 and Akt Signaling Lead to Improved Survival and Function," The Journal of Neuroscience, 28(21):5422-5432.
Miklja et al., (2020). "Everolimus improves the efficacy of dasatinib in PDGFRα-driven glioma," J Clin Invest, 130(10):5313-5325.
Miller et al., (2014). "Rapamycin-mediated lifespan increase in mice is dose and sex dependent and metabolically distinct from dietary restriction," Aging Cell, 13(3): 468-477.
Milowsky et al., (2013). "Phase II study of everolimus in metastatic urothelial cancer," BJU Int, 112(4):462-470.
Molinolo et al., (2012). "mTOR as a molecular target in HPV-associated oral and cervical squamous carcinomas," Clin Cancer Res, 18(9):2558-2568, 19 pages.
Moriya et al., (2014). "Antitumor effect and antiangiogenic potential of the mTOR inhibitor temsirolimus against malignant pleural mesothelioma," Oncol Rep, 31(3):1109-1115.
Ozcelik et al., (2013). "Rapamycin attenuates the progression of tau pathology in P301S tau transgenic mice," PLoS One, 8(5):e62459, 7 pages.
Pleniceanu et al., (2018). "mTORC1 Inhibition Is an Effective Treatment for Sporadic Renal Angiomyolipoma," Kidney International Reports, 3:155-159.
Poore et al., (2019). "Inhibition of mTORC1 in pediatric low-grade glioma depletes glutathione and therapeutically synergizes with carboplatin," Neuro Oncol, 21(2):252-263.
Ray-Coquard et al., (2013). "Everolimus as second- or third-line treatment of advanced endometrial cancer: Endorad, a phase II trial of Gineco," Br J Cancer, 108(9):1771-1777.
Royce et al., (2015). "Everolimus in the Treatment of Metastatic Breast Cancer," Breast Cancer: Basic and Clinical Research, 9:73-79.

Selman et al., (2009). "Ribosomal Protein S6 Kinase 1 Signaling Regulates Mammalian Life Span," Science, 326(5949):140-144.
Shavlakadze et al., (2018). "Short-term Low-Dose mTORC1 Inhibition in Aged Rats Counter-Regulates Age-Related Gene Changes and Blocks Age-Related Kidney Pathology," J Gerontol A Biol Sci Med Sci., 73(7):845-852.
Silic-Benussi et al., (2022). "mTOR inhibition downregulates glucose-6-phosphate dehydrogenase and induces ROS-dependent death in T-cell acute lymphoblastic leukemia cells," Redox Biol, 51:102268, 14 pages.
Siman et al., (2015). "The mTOR Inhibitor Rapamycin Mitigates Perforant Pathway Neurodegeneration and Synapse Loss in a Mouse Model of Early-Stage Alzheimer-Type Tauopathy," PLoS One, 10(11):e0142340, 21 pages.
Spilman et al., (2011). "Inhibition of mTOR by rapamycin abolishes cognitive deficits and reduces amyloid-beta levels in a mouse model of Alzheimer's disease," PLoS One, 5(4):e9979, 8 pages.
Sun et al., (2012). "Chemopreventive and chemotherapeutic actions of mTOR inhibitor in genetically-defined head and neck squamous cell carcinoma mouse model," Clin Cancer Res, 18(19):5304-5313, 18 pages.
Vellai et al., (2003). "Influence of TOR kinase on lifespan in C. elegans," Nature, 426:620.
Vera Aguilera et al., (2018). "Phase II Study of Everolimus in Metastatic Malignant Melanoma (NCCTG-N0377, Alliance)," Oncologist, 23(8):887-e94.
Villamil et al., {2014). "Fibrosis progression in maintenance liver transplant patients with hepatitis C recurrence: a randomised study of everolimus vs. calcineurin inhibitors," Liver, 34(10):1513-1521, 9 pages.
Wolpin et al., (2013). "Multicenter phase II study of tivozanib (AV-951) and everolimus (RAD001) for patients with refractory, metastatic colorectal cancer," Oncologist, 18:377-378.
Wong (2013). "Mammalian target of rapamycin (mTOR) activation in focal cortical dysplasia and related focal cortical malformations," Experimental Neurology, 244:22-26, 11 pages.
Yao et al., (2011). "Everolimus for advanced pancreatic neuroendocrine tumors," N Engl J Med, 364(6):514-523.
Yao et al., (2016). "Everolimus for the treatment of advanced, nonfunctional neuroendocrine tumours of the lung or gastrointestinal tract (Radiant-4): a randomised, placebo-controlled, phase 3 study," Lancet, 387(10022):968-977, 20 pages.
Yi et al., (2020). "Safety and efficacy of sirolimus combined with endocrine therapy in patients with advanced hormone receptor-positive breast cancer and the exploration of biomarkers," Breast, 52:17-22.
Yoo et al., (2013). "Multicenter phase II study of everolimus in patients with metastatic or recurrent bone and soft-tissue sarcomas after failure of anthracycline and ifosfamide," Invest New Drugs, 31(6):1602-1608.
Young et al., (2016). "Human mitochondrial DNA replication machinery and disease," Current Opinion in Genetics & Development, 38:52-62, 20 pages.
Yu et al., (2021). "Efficient Everolimus Treatment for Metastatic Castration Resistant Prostate Cancer with AKT1 Mutation: A Case Report," Onco Targets Ther, 14:5423-5428.
Zeng et al., (2008). "Rapamycin Prevents Epilepsy in a Mouse Model of Tuberous Sclerosis Complex," Ann. Neuorol., 63(4):444-453, 16 pages.
Zeng et al., {2009). "The Mammalian Target of Rapamycin Signaling Pathway Mediates Epileptogenesis in a Model of Temporal Lobe Epilepsy," The Journal of Neuroscience, 29(21):6964-6972.
Zhou et al., {2009). "Pharmacological Inhibition of mTORC1 Suppresses Anatomical, Cellular, and Behavioral Abnormalities in Neural-Specific Pten Knock-Out Mice," The Journal of Neuroscience, 29(6):1773-1783.
Zhu et al., (2011). "Phase 1/2 study of everolimus in advanced hepatocellular carcinoma," Cancer, 117(22):5094-5102.
Zureick et al., (2019). "Successful treatment of a TSC2-mutant glioblastoma with everolimus," BMJ Case Rep, 12(5):e227734, 4 pages.

(56) References Cited

OTHER PUBLICATIONS

Bastin et al., (2000). "Salt Selection and Optimisation Procedures for Pharmaceutical New Chemical Entities," Organic Process Research & Development, 4(5):427-435.
Belikov, (2007). "Chapter 2.6: Relationship between the chemical structure, properties of substances and their effect on the body," in Pharmaceutical Chemistry Med Press Inform, pp. 27-29, 9 pages. English translation.
Berge et al., (1977). "Pharmaceutical salt," J. Pharmaceutical Sciences, 66:1-19.
Durnov et al., (2002). "Pediatric Oncology," 2nd edition, Moscow: "Meditsina" publishing house, p. 139, 5 pages. English translation.
Emsley et al., (2010). "Features and development of Coot," Acta Crystallographica Section D: Biological Crystallography, D66:486-501.
Inoki et al., (2005). "Dysregulation of the TSC-mTOR pathway in human disease," Nature Genetics, 37(7):19-24, 13 pages.
Kabsch, (2010). "XDS," Acta Cryst. D, 66:125-132.
Mashkovsky, (2001). "Medicines", 14th edition, vol. 1, Moscow, p. 11, 3 pages. English translation.
Murshudov et al., (2011). "REFMAC5 for the refinement of macromolecular crystal structures," Acta Crystallographica Section D: Biological Crystallography, 67(Pt 4):355-367.
Pinto-Leite et al., (2012). "Everolimus enhances gemcitabine-induced cytotoxicity in bladder-cancer cell lines," J Toxicol Environ Health A, 75(13-15):788-99. Abstract Only.
Collaborative Computational Project, No. 4 (1994). "The CCP4 suite: programs for protein crystallography," Acta Crystallogr D Biol Crystallogr, 50(Pt 5):760-3.
D'Arcy et al., (2007). "An automated microseed matrix-screening method for protein crystallization," Acta Crystallogr D Biol Crystallogr, 63(Pt 4):550-554. Abstract Only.
Dickman et al., (2000). "Antifungal rapamycin analogues with reduced immunosuppressive activity," Bioorganic & Medicinal Chemistry Letters, 10(13):1405-1408.
Hughes et al., (1992). "The Isolation, synthesis and characterization of an Isomeric Form of Rapamycin," Tetrahedron Letters, 33(33):4739-4742. Abstract Only.
Jiang et al., (2014). "Temsirolimus promotes autophagic clearance of amyloid-β and provides protective effects in cellular and animal models of Alzheimer's disease," Pharmacol Res, 81:54-63.
Leslie (2015). "A Putative Antiaging Drug Takes a Step From Mice to Men," Science, 342(6160):789.
Luengo et al., (1994). "Manipulation of The Rapamycin Effector Domain. Selective Nucleophilic Substitution of The C7 Methoxy Group," Journal of Organic Chemistry, 59(22): 6512-6513.
Merli et al., (2015). "Everolimus in diffuse large B-cell lymphomas," Future Oncol, 11(3):373-83.
Mlerke et al., (1991). "Conformational Analysis of the cis- and trans-Isomers of FK506 by NMR and Molecular Dynamics," Helvetica Chimica Acta, 74(5):1027-1045. Abstract Only.
Van Duyne et al., (1991). "Atomic Structure of the Rapamycin Human Immunophilin FKBP-12 Complex," J. Am. Chem. Soc., 113(19):7433-7434. Abstract Only.
Nakagawa et al., (2013). "New immunosuppressive drug: mTOR inhibitor and thymoglobulin," Journal of the Japanese Society of Nephrology, 55(2):112-118. English translation.
Combe et al., (2007). "Early rheumatoid arthritis: strategies for prevention and management," Best Practice & Research Clinical Rheumatology, 21(1):27-42.
Eynott et al., (2003). "Effects of cyclosporin A and a rapamycin derivative (SAR943) on chronic allergic inflammation in sensitized rats," Immunology, 109(3):461-467.
Kasai (2016). "What causes human cancer? Approaches from the chemistry of DNA damage," Genes and Environment, 38(19), 13 pages.
Paschoal et al., (2017). "mTORC1 inhibition with rapamycin exacerbates adipose tissue inflammation in obese mice and dissociates macrophage phenotype from function," Immunobiology, 222(2):261-271.

RAPAMYCIN DERIVATIVES

CLAIM OF PRIORITY

This application is an U.S. National Phase filing of International Application Serial No. PCT/IB2019/060957 filed 17 Dec. 2019 and claims priority from U.S. Provisional Application Ser. No. 62/781,242 filed 18 Dec. 2018, respectively, each of which are incorporated herein by reference in their entireties.

FIELD

The disclosure provides 32-deoxo-rapamycin derivatives, to their preparation, and to their methods of use.

BACKGROUND

In mammalian cells, the target of rapamycin (mTOR) kinase exists in two distinct multiprotein complexes, described as the mTORC1 complex and the mTORC2 complex, both of which sense the availability of nutrients and energy, and integrate inputs from growth factors and stress signaling. mTORC1 integrates signals from growth factors and nutrients and controls cell growth and metabolism (Laplante M. et al. Cell. (2012) 149(2):274-93), and is a key regulator of protein translation and autophagy. The mTORC1 complex is sensitive to allosteric mTOR inhibitors such as rapamycin and rapamycin analogs (so called 'rapalogs'). Rapamycin and previously-produced rapalogs' mode of action involves the formation of an intracellular complex with and of the FK506 binding proteins, such as FKBP12, FKBP12.6, FKBP13, FKBP25, FKBP51, or FKBP52 (these FKBPs will be referenced here as "FKBP" or "FKBPs"), followed by the binding of the FKBP-rapalog complex to the FRB (FK506-rapamycin binding) domain of mTOR. März A. M. et al. Mol Cell Biol. (2013) 33(7):1357-1367. Such interaction of the FKBP-rapalog complex with mTORC1 results in allosteric inhibition of the complex. Rapamycin and rapalogs, such as RAD001 (everolimus; Afinitor®), have gained clinical relevance by inhibiting the activity of mTORC1, which is associated with both benign and malignant proliferation disorders. Royce M. E. et al. Breast Cancer (Auckl). (2015) 9:73-79; Pleniceanu O. et al. Kidney Int Rep. (2018) 3(1):155-159.

Rapamycin is a known macrolide antibiotic produced by *Streptomyces hygoscopius*, see e.g. McAlpine, J. B., et al., J. Antibiotics (1991) 44:688; Schreiber, S. L.; et al., J. Am. Chem. Soc. (1991) 113:7433; U.S. Pat. No. 3,929,992. The following numbering convention for rapamycin and its derivatives used in this document is shown below:

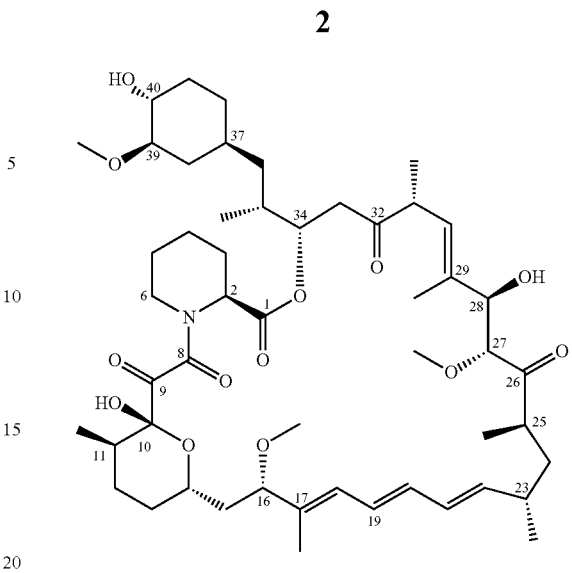

Rapamycin is a potent immunosuppressant and has also been shown to have antitumor and antifungal activity. It has been shown to be useful in preventing or treating systemic lupus erythematosus, pulmonary inflammation, insulin-dependent diabetes mellitus, skin disorders such as psoriasis, smooth muscle cell proliferation and intimal thickening following vascular injury, adult T-cell leukemia/lymphoma, malignant carcinomas, cardiac inflammatory disease, anemia and increased neurite outgrowth. Its utility as a pharmaceutical, however, is restricted by its very low and variable bioavailability. Moreover, rapamycin is challenging to formulate, making it difficult to obtain stable galenic compositions.

In animal models, rapalogs extend lifespan and delay the onset of age-related diseases. Aging, like other biological processes, is regulated by signaling pathways such as the TOR pathway (named "TOR" in this case, to include the yeast and *C elegans* systems) and, in mammals, the mTORC1 pathway. Modulation of TOR and mTORC1 signaling prolongs lifespan and delays the onset of age-related diseases in a wide array of organisms, from flies to mammals. For instance, inhibition of the TOR pathway by genetic mutation extended lifespan in yeast, *C elegans*, and *drosophila*, and inhibition of the mTORC1 pathway extended lifespan in mice (Kaeberlein et al., Science (2005) 310:1193-1196; Kapahi et al., Curr Biol (2004) 14:885-890; Selman et al., Science (2009) 326:140-144; Vellai et al., Nature (2003) 426:620). In addition, the mTORC1 inhibitor rapamycin extended the lifespan of mice even when given late in life (Harrison et al., Nature (2009) 460(7253):392-395). These data raise the possibility that drugs that target the mammalian TOR (mTOR) pathway will have therapeutic effects in aging and age-related diseases in humans. A report of a clinical trial using rapamycin in elderly men was described by M. Leslie in Science, 2013, 342. J. Mannick et al. describe in Sci Transl Med. (2014) 6(268): 268ra179 that mTOR inhibition improves the immune function in the elderly. However, investigators have been wary of using currently available mTOR inhibitors in human aging trials due to their side effects (including immunosuppression, cytopenias, stomatitis, GI distress and interstitial pneumonitis).

Pharmacological inhibition of the mTOR pathway, either before or immediately following neurological insults, can prevent pathological changes in animal brains and the development of spontaneous recurrent seizure in an acquired epilepsy model (Zeng et al., The mammalian target of rapamycin signaling pathway mediates epileptogenesis in a model of temporal lobe epilepsy; J. Neurosci., (2009) pp. 6964-6972). Rapamycin and rapalogs are therefore also considered to be of potential value in such indications.

Rapalogs have been shown to be efficacious in human beings in the setting of liver fibrosis. See, e.g., Liver Int. (2014) 34(10):1513-21.

Mitochondrial myopathy (MM) is the most common manifestation of adult-onset mitochondrial disease and shows a multifaceted tissue-specific stress response: (1) transcriptional response, including metabolic cytokines FGF21 and GDF15; (2) remodeling of one-carbon metabolism; and (3) the mitochondrial unfolded protein response. In Cell Metabolism 26, 419-428, Aug. 1, 2017, it is described by Khan et al. that these processes are part of one integrated mitochondrial stress response (ISRmt), which is controlled by mTORC1 in skeletal muscle. A mtDNA replication defect activates mTORC1, which drives an integrated mitochondrial stress response through ATF4 activation, inducing de novo nucleotide and serine synthesis, the 1C-cycle, and FGF21 and GDF15 production. mTORC1 inhibition by rapamycin downregulated all components of ISRmt (the integrated mitochondrial stress response), improved all MM hallmarks, and reversed the progression of even late-stage MM, without inducing mitochondrial biogenesis. Rapamycin and rapalogs are therefore also considered to be of potential value in such indications.

Thus, there remains a need to provide new mTOR inhibitors that are good drug candidates exhibiting a balance of good potency, stability, and bioavailability.

SUMMARY

The compounds of Formula (I) are mTORC1 inhibitors and are useful in the treatment of disorders, particularly age-related disorders, or diseases and disorders currently approved for treatment using rapalogs. Full reduction of the ketone at C32 and the replacement of the C16 methoxy group as described herein, provides compounds exhibiting a balance of good potency, stability and bioavailability.

Without wishing to be bound by theory, the compounds of Formula (I) are effective in inhibiting mTORC1 by binding to FKBP12 in settings where FKBP12 levels are sufficient to inhibit mTORC1. The compounds of Formula (I) may also be effective in inhibiting mTORC1 by binding to FKBP25, FKBP51 and/or FKBP52 in settings where FKBP12 levels are insufficient to inhibit mTORC1, but where FKBP25, FKBP51 and/or FKBP52 are sufficient to inhibit mTORC1. Thus, in certain cell types (e.g., and therefore in different potential indications, e.g., such as the diseases and disorders described herein), FKBP levels may vary. As a result, RAD001 may be effective in such cell types with sufficient levels of FKBP12. However, compounds of Formula (I) may be effective in certain cell types with sufficient or insufficient levels of FKBP12.

In one aspect, the disclosure provides a compound of Formula (I) or a pharmaceutically acceptable salt thereof, wherein:

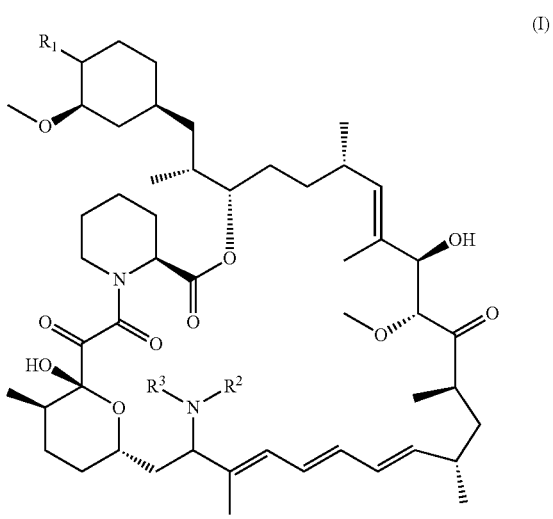

$R^1$ is selected from the group consisting of —$OR^a$ and a 5-6 membered heteroaryl;

$R^2$ and $R^3$ are each independently selected from the group consisting of H, $C_{1-6}$alkyl, —$OR^b$, —$C_{0-6}$alkylene-$SO_2R^4$, and —$C(O)OR_5$;

$R^4$ is —$OR^5$, $C_{1-6}$alkyl, $C_{1-6}$haloalkyl, hetero$C_{1-6}$alkyl, $C_{1-6}$hydroxyalkyl, $C_{3-8}$cycloalkyl$C_{0-6}$alkyl;

$R^5$ is H or $C_{1-6}$alkyl;

$R^a$ is selected from the group consisting of H, —P(O)($R^b$)$_2$, —C(O)$R^c$, —C(O)O$R^c$, $C_{1-6}$alkyl, and $C_{1-6}$hydroxyalkyl;

each $R^b$ is independently selected from the group consisting of H and $C_{1-6}$alkyl; and each $R^c$ is independently selected from the group consisting of H, $C_{1-6}$alkyl, and $C_{1-6}$hydroxyalkyl.

In an embodiment, the disclosure provides a pharmaceutical composition comprising a therapeutically effective amount of a compound of Formula (I) or a pharmaceutically acceptable salt thereof and one or more pharmaceutically acceptable carriers.

In an embodiment, the disclosure provides a pharmaceutical combination comprising a therapeutically effective amount of a compound of Formula (I) or a pharmaceutically acceptable salt thereof and one or more therapeutically active agents.

In another aspect, the disclosure provides a method for treating a disorder or a disease mediated by the mTOR pathway in a subject in need thereof, the method comprising administering to the subject a therapeutically effective amount of a compound of Formula (I), or a pharmaceutical composition, or a pharmaceutical combination thereof.

In another aspect, the disclosure provides a method for treating a disease or disorder in a subject, wherein the target tissue, organ, or cells associated with the pathology of the disease or disorder has FKBP12 levels insufficient to inhibit mTORc1, the method comprising administering to the subject in need thereof a therapeutically effective amount of a compound of Formula (I) or a pharmaceutically acceptable salt thereof, or a pharmaceutical composition described herein, or a pharmaceutical combination described herein.

In an embodiment, the compound of Formula (I) or a pharmaceutically acceptable salt thereof has higher affinity binding to FKBP12, FKBP51, and/or FKBP52, sufficient to inhibit mTORc1, e.g., as compared to rapamycin or RAD001.

In an embodiment, a compound of Formula (I) or a pharmaceutically acceptable salt thereof may complex with FKBP12, FKBP25, FKBP51, and/or FKBP52, to bind and inhibit mTORc1 more potently as compared to rapamycin or RAD001.

In an embodiment, the higher affinity binding to FKBP12, FKBP25, FKBP51, and/or FKBP52, results in greater efficacy, e.g., as compared to rapamycin or RAD001.

In an embodiment, efficacy of treatment is determined empirically, e.g., as compared to rapamycin or RAD001.

In another aspect, the disclosure provides a method for treating a disease or disorder in a subject having, or determined to have, FKBP12 levels insufficient to inhibit mTORc1, the method comprising administering to the subject in need thereof a therapeutically effective amount of a compound of Formula (I) or a pharmaceutically acceptable salt thereof, or a pharmaceutical composition described herein, or a pharmaceutical combination described herein.

In an embodiment, the subject has, or is determined to have, FKBP12 levels in the target tissue, organ, or cells associated with the pathology of the disease or disorder insufficient to inhibit mTORc1.

In an embodiment, a compound of Formula (I) or a pharmaceutically acceptable salt thereof has higher affinity binding to FKBP12, FKBP25, FKBP51, and/or FKBP52, sufficient to inhibit mTORc1, e.g., as compared to rapamycin or RAD001.

In an embodiment, efficacy of treatment is determined empirically, e.g., as compared to rapamycin or RAD001.

In another aspect, the disclosure provides a method of treating a disease or disorder in a subject having, or previously determined to have, FKBP12 levels sufficient to inhibit mTORc1, the method comprising administering to the subject in need thereof a therapeutically effective amount of a compound of Formula (I) or a pharmaceutically acceptable salt thereof, or a pharmaceutical composition described herein, or a pharmaceutical combination described herein.

In another aspect, the disclosure provides a method for treating an age-related disease or disorder in a subject in need thereof, the method comprising administering to the subject a therapeutically effective amount of a compound of Formula (I) or a pharmaceutically acceptable salt thereof, or a pharmaceutical composition described herein, or a pharmaceutical combination described herein.

In an embodiment, the disease or disorder is selected from sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

In another aspect, the disclosure provides a method for treating a disease or disorder in a subject in need thereof, the method comprising administering to the subject a therapeutically effective amount of a compound of Formula (I) or a pharmaceutically acceptable salt thereof, or a pharmaceutical composition, or a pharmaceutical combination thereof, wherein the disorder or disease is selected from:

Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Asthma;
Multi-drug resistance (MDR);
Fungal infections;
Inflammation;
Infection;
Age-related diseases;
Neurodegenerative diseases;
Proliferative disorders, e.g., cancer;
Seizures and seizure related disorders; and
Mitochondrial myopathy and mitochondrial stress.

In another aspect, the disclosure provides a method for treating cancer in a subject in need thereof, the method comprising administering to the subject a therapeutically effective amount of a compound of Formula (I) or a pharmaceutically acceptable salt thereof, or a pharmaceutical composition described herein, or a pharmaceutical combination described herein.

In an embodiment, the method further comprises a PD-1/PDL-1 inhibitor.

In an embodiment, the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, and neck cancer.

In an embodiment, the disorder is a liver disorder that includes the process of fibrosis and/or inflammation, e.g., liver fibrosis that occurs in end-stage liver disease; liver cirrhosis; liver failure due to toxicity; non-alcohol-associated hepatic steatosis or NASH; and alcohol-associated steatosis.

In an embodiment, the disorder is a kidney disorder that includes the process of fibrosis or inflammation in the kidney, e.g., kidney fibrosis, which occurs as a result of acute kidney injury, leading to chronic kidney disease and diabetic nephropathy.

In an embodiment, the disorder is a heart dysfunction, e.g., myocardial infarction or cardiac hypertrophy. In an embodiment, the heart dysfunction is systolic and/or diastolic dysfunction. In an embodiment, the heart dysfunction is hypertension. In an embodiment, the heart dysfunction results in a decline in ejection fraction.

In an embodiment, the disorder is an immune-senescence leading to cancer due to a decrease in immune-surveillance.

In an embodiment, the disorder is cancer, including tumors which are treated by immunotherapy, and those which have been previously treated by either rapamycin, RAD001, or another rapalog. In an embodiment, the cancer includes tumors where the mTOR pathway is shown to be activated, including settings where there is a mutation in the Tsc1 gene, or where the tumor microenvironment is appropriately treated by a rapalog.

The details of one or more embodiments of the disclosure are set forth herein. Other features, objects, and advantages of the disclosure will be apparent from the Figures, the Detailed Description, the Examples, and the Claims.

BRIEF DESCRIPTION OF THE DRAWINGS

FIG. 4A shows immunoblot images of phosphorylated (p-) and total (t-) S6 proteins in rat livers treated with a vehicle or 1, 3 or 10 mg/kg of Compound 2 and analyzed at 3 hours following treatment. GAPDH (glyceraldehyde 3-phosphate dehydrogenase) was used to control for protein loading. The histogram in FIG. 4B shows densitometric quantification of p-S6 to t-S6. In the histogram depicted in FIG. 4B, average arbitrary values that indicate p-S6/t-S6 ratios are shown above each bar. X axis represents orally given doses (1, 3, or 10 mg/kg). Y-axis represents arbitrary units. Six rats were used in each experimental group. Data are mean±standard deviation. Data were analyzed with a one way ANOVA followed by Dunnett's multiple comparison tests, where means from all groups were compared to the vehicle treated group. ****P<0.001.

DETAILED DESCRIPTION

Figure 1:
FIG. 1 depicts the x-ray co-crystal structure of Compound 2 with FKBP12. The C16 substituent is in (S)-configuration.

The compounds disclosed herein are mTORc1 inhibitors useful in the treatment of disorders, particularly age-related disorders, or disorders currently approved for treatment using rapalogs, such as RAD001.

Definitions

Unless specified otherwise, the term "compounds of the disclosure," "compound of the disclosure," "a compound of Formula (I)," and "compounds of Formula (I) refers to compounds of Formula (I), subformulae (I)-A, (I)-B, (I)-C, (I)-D, (I)-E, (I)-F, exemplified compounds, and salts thereof, as well as all stereoisomers (including diastereoisomers and enantiomers), rotamers, tautomers and isotopically labeled compounds (including deuterium substitutions), as well as inherently formed moieties.

The term "a therapeutically effective amount" of a compound of the disclosure refers to an amount of the compound of the disclosure that will elicit the biological or medical response of a subject, for example, reduction or inhibition of an enzyme or a protein activity, or ameliorate symptoms, alleviate conditions, slow or delay disease progression, or prevent a disease, etc. In an embodiment, the term "a therapeutically effective amount" refers to the amount of the compound of the disclosure that, when administered to a subject, is effective to (1) at least partially alleviate, or ameliorate a condition, or a disorder or a disease (i) mediated by the mTOR pathway, or (ii) associated with mTOR activity, or (iii) characterized by activity (normal or abnormal) of mTOR; or (2) reduce or inhibit the activity of mTOR; or (3) reduce or inhibit the expression of mTOR. In an embodiment, the term "a therapeutically effective amount" refers to the amount of the compound of the disclosure that, when administered to a cell, or a tissue, or a non-cellular biological material, or a medium, is effective to at least partially reduce or inhibit the activity of mTOR; or at least partially reduce or inhibit the expression of mTOR.

As used herein, the term "subject" refers to primates (e.g., humans, male or female), dogs, cats, rabbits, guinea pigs, pigs, rats and mice. In certain embodiments, the subject is a primate. In yet other embodiments, the subject is a human.

The terms "administer," "administering," or "administration," as used herein refers to implanting, absorbing, ingesting, injecting, inhaling, or otherwise introducing an inventive compound, or a pharmaceutical composition thereof.

As used herein, the term "inhibit," "inhibition" or "inhibiting" refers to the reduction or suppression of a given condition, symptom, or disorder, or disease, or a significant decrease in the baseline activity of a biological activity or process.

As used herein, the term "treat", "treating," or "treatment" of any disease or disorder refers to alleviating, delaying the onset of, ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient. In an embodiment, "treatment," "treat," and "treating" require that signs or symptoms of the disease, disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the term "prevent", "preventing," or "prevention" of any disease or disorder refers to the prophylactic treatment of the disease or disorder; or delaying the onset or progression of the disease or disorder.

As used herein, "age-related disease or disorder" refers to any disease or disorder whose incidence in a population or severity in an individual correlates with the progression of age. More specifically, an age-related disease or disorder is a disease or disorder whose incidence is at least 1.5 fold higher among human individuals greater than 65 years of age relative to human individuals between the ages of 25-35. Examples of age-related disorders include, but are not limited to: sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

As used herein, a subject is "in need of" a treatment if such subject would benefit biologically, medically or in quality of life from such treatment.

As used herein, the term "a," "an," "the" and similar terms used in the context of the disclosure (especially in the context of the claims) are to be construed to cover both the singular and plural unless otherwise indicated herein or clearly contradicted by the context.

The term "alkyl" refers to a radical of a straight-chain or branched saturated hydrocarbon group having from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl).

"Alkylene" refers to a divalent radical of an alkyl group, e.g., —CH$_2$—, —CH$_2$CH$_2$—, and —CH$_2$CH$_2$CH$_2$—.

"Heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl").

"Haloalkyl" refers to a substituted alkyl group, wherein one or more of the hydrogen atoms are independently replaced by a halogen, e.g., fluoro, bromo, chloro, or iodo and includes alkyl moieties in which all hydrogens have been replaced by halo (e.g., perfluoroalkyl). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —CF$_3$, —CF$_2$CF$_3$, —CF$_2$CF$_2$CF$_3$, —CCl$_3$, —CH$_2$CH$_2$Cl, —CH$_2$CH$_2$CH$_2$Cl, —CFCl$_2$, —CF$_2$Cl, and the like.

"Hydroxy$C_{1-6}$alkyl" refers to an alkyl group substituted with one or more —OH groups. Examples of hydroxy$C_{1-6}$alkyl groups include HO—CH$_2$—, HO—CH$_2$CH$_2$—, and —CH$_2$—CH(OH)CH$_3$.

"Cycloalkyl" refers to a cyclic, bicyclic, tricyclic, or polycyclic non-aromatic hydrocarbon groups having 3 to 12 carbons. In an embodiment, the cycloalkyl is monocyclic having 3-6 carbons. The cycloalkyl groups can contain fused or spiro rings. Fused rings are rings that share a common carbon atom. Examples of cycloalkyl moieties include, but are not limited to, cyclopropyl, cyclobutyl, cyclopentyl, cyclohexyl, adamantyl, and norbornyl.

"Cycloalkylalkyl" refers to a (cycloalkyl)-alkyl radical where cycloalkyl and alkyl are as disclosed herein. The "cycloalkylalkyl" is bonded to the parent molecular structure through the alkyl group. In an embodiment, the cycloalkylalkyl moiety is a $C_3$cycloalkyl$C_{1-6}$alkyl group. In an embodiment, the cycloalkylalkyl moiety is a $C_4$cycloalkyl$C_{1-6}$alkyl group. In an embodiment, the cycloalkylalkyl is a $C_5$cycloalkyl$C_{1-6}$alkyl group. In an embodiment, the cycloalkylalkyl is a $C_6$cycloalkyl$C_{1-6}$alkyl group. In an embodiment, the cycloalkylalkyl moiety is a $C_3$cycloalkyl$C_{1-3}$alkyl group. In an embodiment, the cycloalkylalkyl moiety is a $C_4$cycloalkyl$C_{1-3}$alkyl group. In an embodiment, the cycloalkylalkyl is a $C_5$cycloalkyl$C_{1-3}$alkyl group. In an embodiment, the cycloalkylalkyl is a $C_6$cycloalkyl$C_{1-3}$alkyl group.

"Heteroaryl" refers to a stable, aromatic, mono- or bicyclic ring radical having the specified number of ring atoms and comprising one or more heteroatoms individually selected from nitrogen, oxygen and sulfur. The heteroaryl radical may be bonded via a carbon atom or heteroatom. In an embodiment, the heteroaryl is a 5- or 6-membered heteroaryl. In an embodiment, the heteroaryl is a 5-membered heteroaryl. In an embodiment, the heteroaryl is a 6-membered heteroaryl. Examples of heteroaryl groups include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl, pyridyl, quinolinyl, isoquinolinyl, indolyl, indazolyl, oxadiazolyl, benzothiazolyl, quinoxalinyl, and the like.

As used herein, "hydroxy" or "hydroxyl" refers to —OH.

As used herein, the definition of each expression, e.g., alkyl, m, n, etc., when it occurs more than once in any structure, is intended to be independent of its definition elsewhere in the same structure.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Certain compounds of the disclosure may exist in particular geometric or stereoisomeric forms. If, for instance, a particular enantiomer of a compound of the disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise stated, structures depicted herein are also meant to include geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the disclosed compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the disclosed structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the disclosure.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100*100\%=80\%.$$

Thus, a composition containing 90% of one enantiomer and 10% of the other enantiomer is said to have an enantiomeric excess of 80%. The compounds or compositions described herein may contain an enantiomeric excess of at least 50%, 75%, 90%, 95%, or 99% of one form of the compound, e.g., the S-enantiomer. In other words such compounds or compositions contain an enantiomeric excess of the S enantiomer over the R enantiomer.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The compounds disclosed herein may also contain unnatural proportions of atomic isotopes at one or more of the atoms that constitute such compounds. For example, the compounds may be radiolabeled with radioactive isotopes, such as for example deuterium ($^{2}$H), tritium ($^{3}$H), carbon-13 ($^{13}$C), or carbon-14 ($^{14}$C). All isotopic variations of the compounds disclosed herein, whether radioactive or not, are intended to be encompassed within the scope of the present disclosure. In addition, all tautomeric forms of the compounds described herein are intended to be within the scope of the disclosure.

The term "tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base. Tautomeric forms may be relevant to the attainment of the optimal chemical reactivity and biological activity of a compound of interest.

Compounds

In one aspect, the disclosure provides a compound of Formula (I) or a pharmaceutically acceptable salt thereof, wherein:

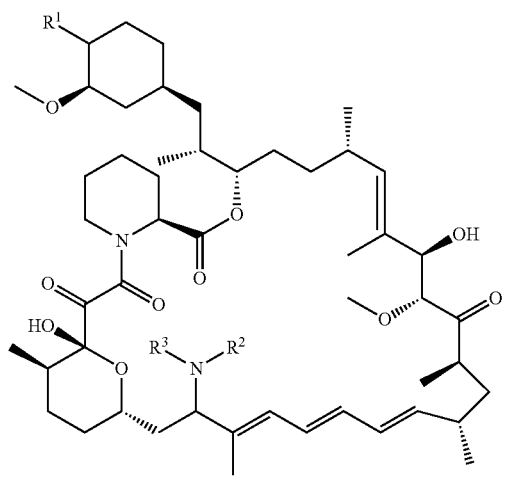

(I)

$R^1$ is selected from the group consisting of —$OR^a$ and a 5-6 membered heteroaryl;

$R^2$ and $R^3$ are each independently selected from the group consisting of H, $C_{1-6}$alkyl, —$OR^b$, —$C_{0-6}$alkylene-$SO_2R^4$, and —$C(O)OR^5$;

$R^4$ is —$OR^5$, $C_{1-6}$alkyl, $C_{1-6}$haloalkyl, heteroC$_{1-6}$alkyl, $C_{1-6}$hydroxyalkyl, $C_{3-8}$cycloalkylC$_{0-6}$alkyl;

$R^5$ is H or $C_{1-6}$alkyl;

$R^a$ is selected from the group consisting of H, —P(O)($R^b$)$_2$, —C(O)$R^c$, —C(O)O$R^c$, $C_{1-6}$alkyl, and $C_{1-6}$hydroxyalkyl;

each $R^b$ is independently selected from the group consisting of H and $C_{1-6}$alkyl; and each $R^c$ is independently selected from the group consisting of H, $C_{1-6}$alkyl, and $C_{1-6}$hydroxyalkyl.

In an embodiment, $R^1$ is —$OR^a$. In an embodiment, $R^1$ is a 5-6 heteroaryl, e.g., a 5-membered heteroaryl. In an embodiment, $R^1$ is selected from the group consisting of hydroxy,

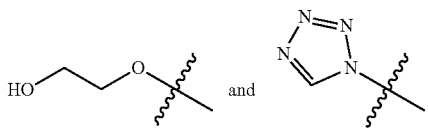

and

.

In an embodiment, $R^2$ and $R^3$ are each independently selected from the group consisting of H and —$OR^b$. In an embodiment, $R^2$ and $R^3$ are each independently selected from the group consisting of H, $C_{1-6}$alkyl, and —$C_{0-6}$alkylene-$SO_2R^4$. In an embodiment, $R^2$ and $R^3$ are each independently selected from the group consisting of H, hydroxyl, —$C_{0-6}$alkylene-$SO_2R^4$, and —$C(O)OR^5$.

In an embodiment, the compound is a compound of Formula (I) or a pharmaceutically acceptable salt thereof, wherein:

$R^1$ is selected from the group consisting of hydroxy,

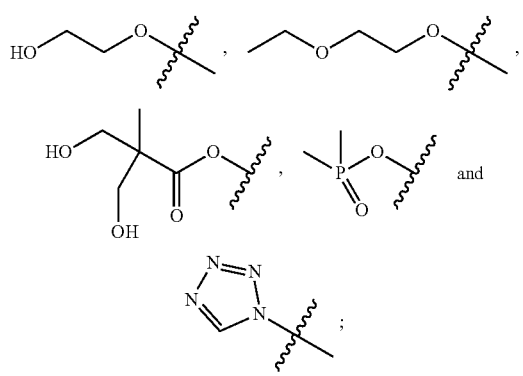

$R^2$ and $R^3$ are each independently selected from the group consisting of H, hydroxyl, —$C_{0-6}$alkylene-$SO_2R^4$, and —$C(O)OR^5$;

$R^4$ is —$OR^5$, $C_{1-6}$alkyl, $C_{1-6}$haloalkyl, $C_{1-6}$hydroxyalkyl, $C_{3-8}$cycloalkylC$_{0-6}$alkyl; and $R^5$ is H or $C_{1-6}$alkyl. In an embodiment, $R^2$ is H, hydroxyl, or $C_{1-6}$alkyl; and $R^3$ is —$C_{0-6}$alkylene-$SO_2R^4$ or —$C(O)OR^5$.

In an embodiment, the compound is a compound of Formula (I) or a pharmaceutically acceptable salt thereof, wherein:

$R^1$ is hydroxyl;

$R^2$ and $R^3$ are each independently selected from the group consisting of H and —$C_{0-6}$alkylene-$SO_2R^4$; and $R^4$ is $C_{1-6}$alkyl. In an embodiment, one of $R^2$ and $R^3$ is H and the other is —$C_{0-6}$alkylene-$SO_2R^4$.

In an embodiment, the compound is a compound having structural Formula (I)-A or (I)-B:

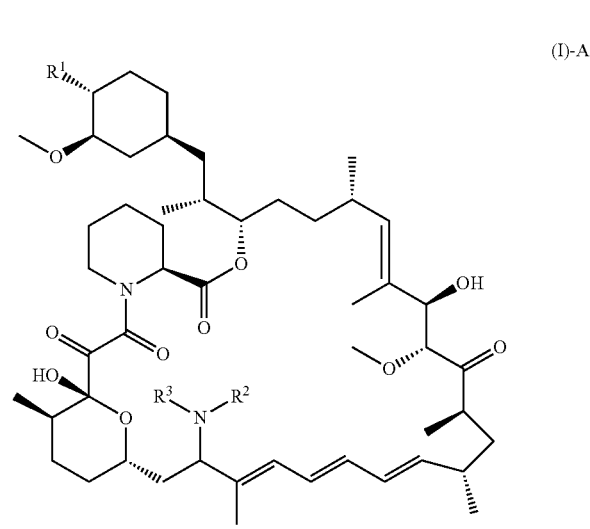

(I)-A

-continued
(I)-B
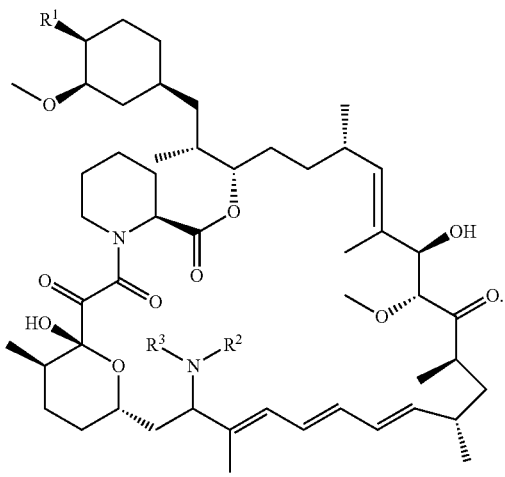
In an embodiment, the compound is a compound having structural Formula (I)-C or (I)-D:
(I)-C
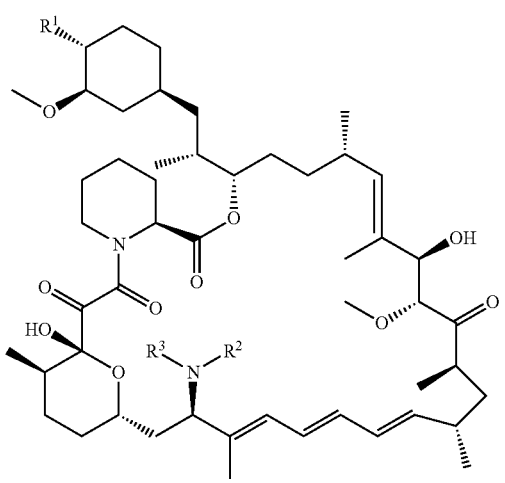
(I)-D
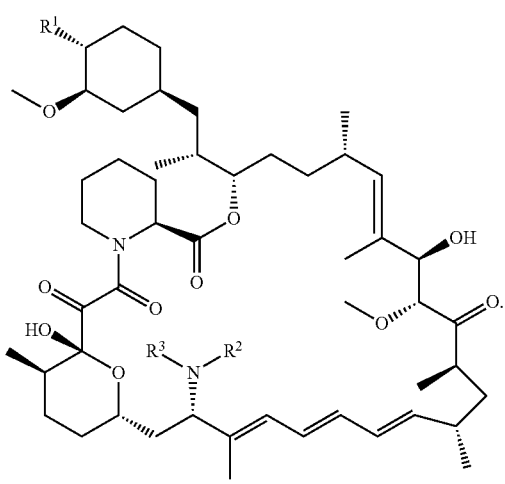
In an embodiment, the compound is a compound having structural Formula (I)-E or (I)-F:
(I)-E
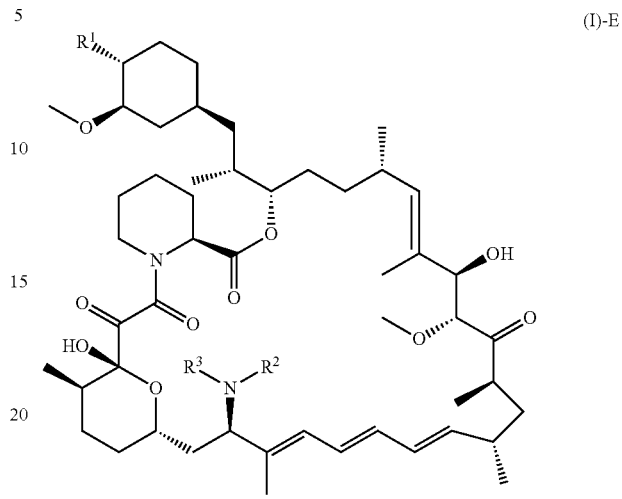
(I)-F
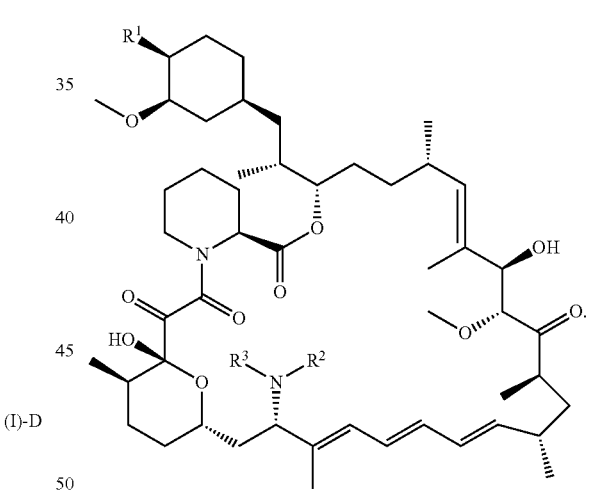
In an embodiment, the compound or pharmaceutically acceptable salt thereof is selected from Table 1.

TABLE 1

| Compound | Structure |
| --- | --- |
| 1 | 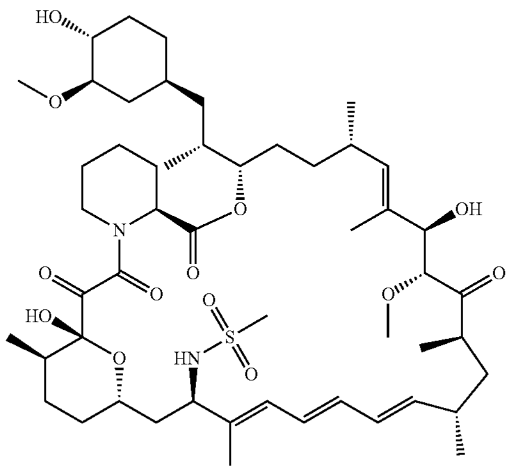 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@H]1O] |
| 2 | 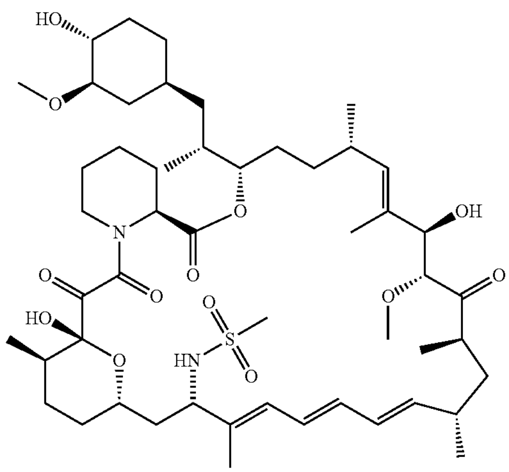 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@H]1O] |
| 3 | 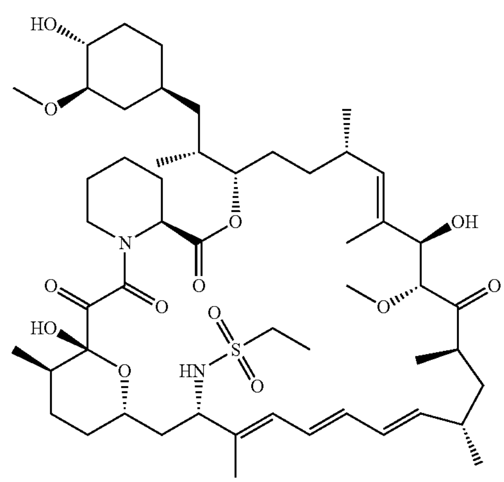 [SMILES: CCS(=O)(=O)N[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |

TABLE 1-continued
| Compound | Structure |
|---|---|
| 4 | 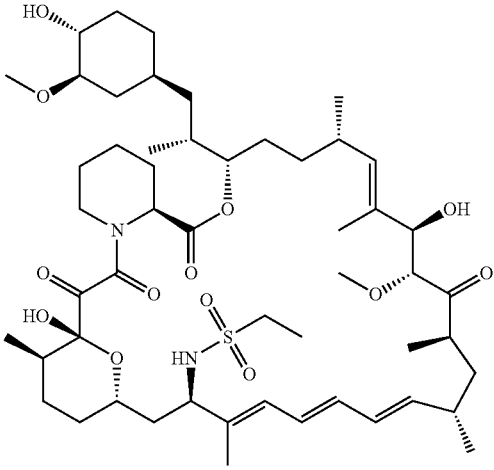 [SMILES: CCS(=O)(=O)N[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |
| 5 | 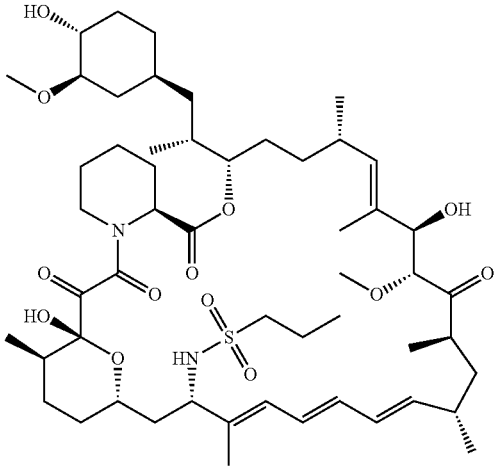 [SMILES: CCCS(=O)(=O)N[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |
| 6 | 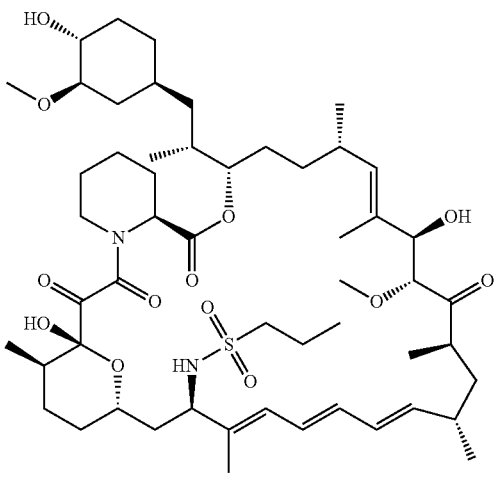 [SMILES: CCCS(=O)(=O)N[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |

TABLE 1-continued
| Compound | Structure |
|---|---|
| 7 | 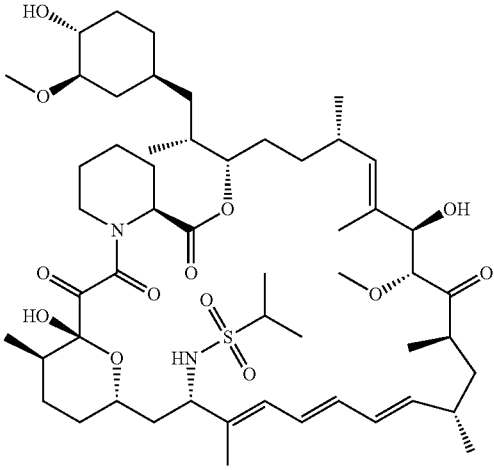 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C(C)C)C[C@@H]3CC[C@@H](C)[C@@](O)(O3)C(=O)C(=O)N3CCCC[C@H]3C(=O)O2)CC[C@H]1O] |
| 8 | 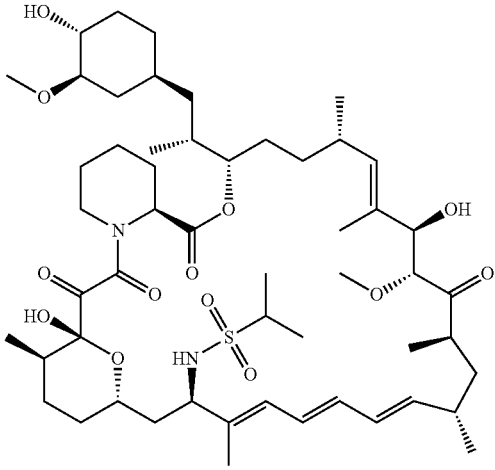 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)C(C)C)C[C@@H]3CC[C@@H](C)[C@@](O)(O3)C(=O)C(=O)N3CCCC[C@H]3C(=O)O2)CC[C@H]1O] |
| 9 | 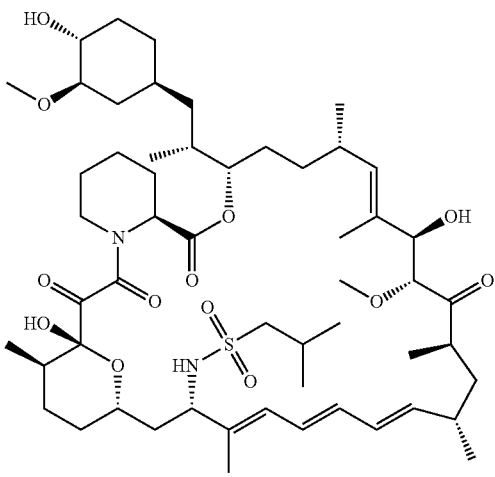 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)CC(C)C)C[C@@H]3CC[C@@H](C)[C@@](O)(O3)C(=O)C(=O)N3CCCC[C@H]3C(=O)O2)CC[C@H]1O] |

TABLE 1-continued
| Compound | Structure |
| --- | --- |
| 10 | 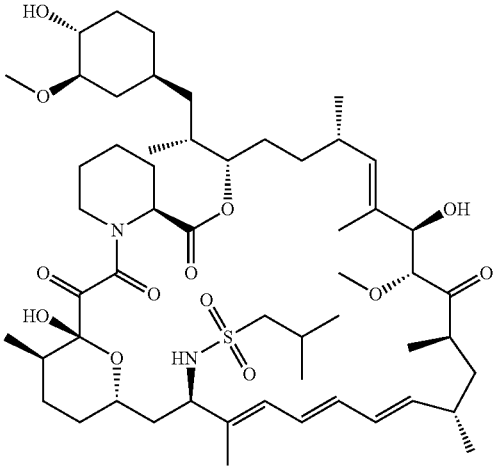 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)CC(C)C)C[C@@H]3CC[C@@H](C)[C@@](O)(O3)C(=O)C(=O)N3CCCC[C@H]3C(=O)O2)CC[C@H]1O] |
| 11 | 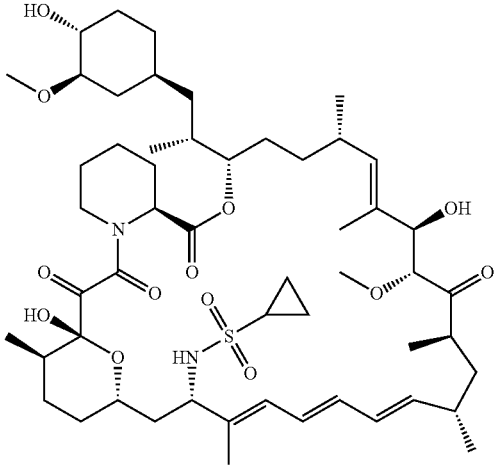 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C3CC3)C[C@@H]3CC[C@@H](C)[C@@](O)(O3)C(=O)C(=O)N3CCCC[C@H]3C(=O)O2)CC[C@H]1O] |
| 12 | 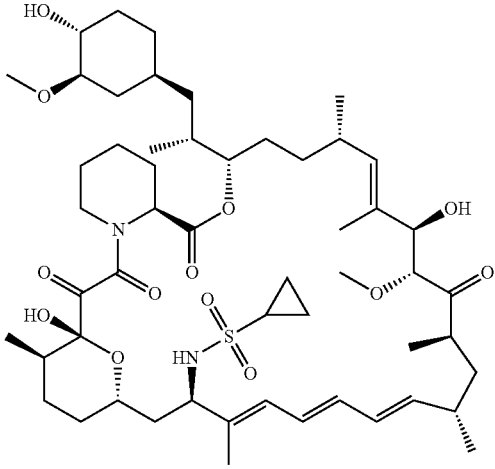 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)C3CC3)C[C@@H]3CC[C@@H](C)[C@@](O)(O3)C(=O)C(=O)N3CCCC[C@H]3C(=O)O2)CC[C@H]1O] |

TABLE 1-continued
| Compound | Structure |
|---|---|
| 13 | 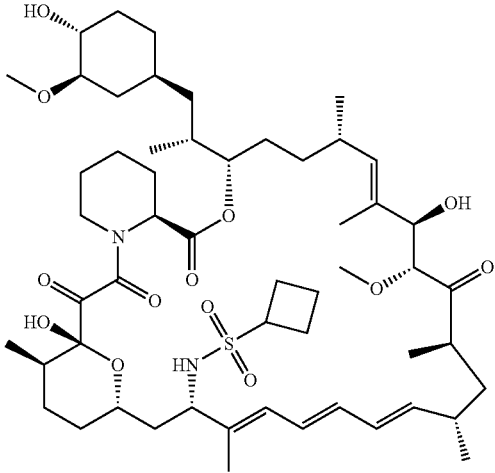 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C3CCC3)C[C@@H]3CC[C@@H](C)[C@@](O)(O3)C(=O)C(=O)N3CCCC[C@H]3C(=O)O2)CC[C@H]1O] |
| 14 | 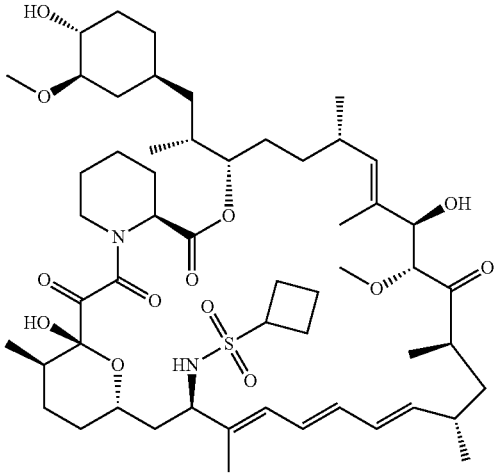 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)C3CCC3)C[C@@H]3CC[C@@H](C)[C@@](O)(O3)C(=O)C(=O)N3CCCC[C@H]3C(=O)O2)CC[C@H]1O] |
| 15 | 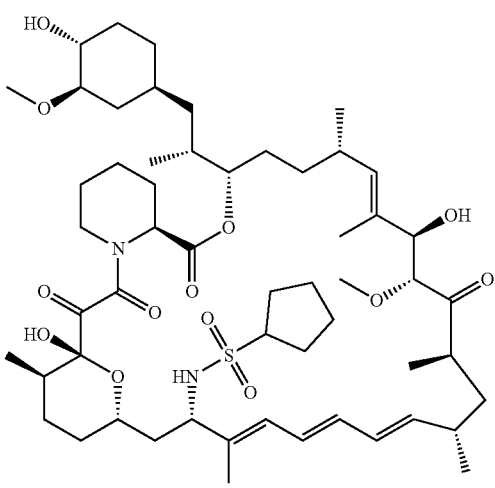 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C3CCCC3)C[C@@H]3CC[C@@H](C)[C@@](O)(O3)C(=O)C(=O)N3CCCC[C@H]3C(=O)O2)CC[C@H]1O] |

TABLE 1-continued

| Compound | Structure |
| --- | --- |
| 16 | 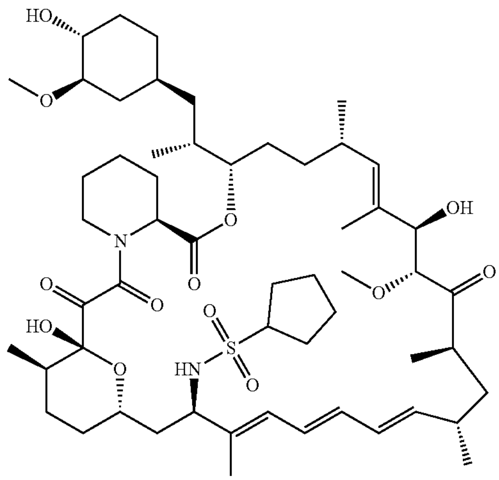 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)C3CCCC3)C[C@@H]3CC[C@@H](C)[C@@](O)(O3)C(=O)C(=O)N3CCCC[C@H]3C(=O)O2)CC[C@H]1O] |
| 17 | 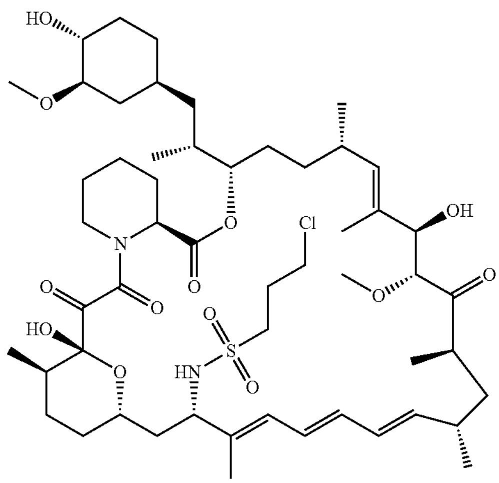 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)CCCCl)C[C@@H]3CC[C@@H](C)[C@@](O)(O3)C(=O)C(=O)N3CCCC[C@H]3C(=O)O2)CC[C@H]1O] |
| 18 | 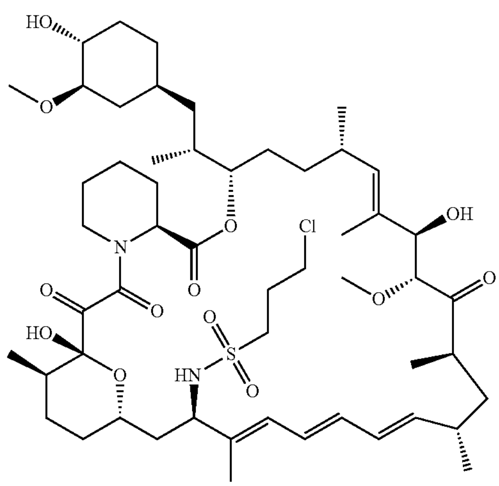 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)CCCCl)C[C@@H]3CC[C@@H](C)[C@@](O)(O3)C(=O)C(=O)N3CCCC[C@H]3C(=O)O2)CC[C@H]1O] |

TABLE 1-continued
| Compound | Structure |
|---|---|
| 19 | 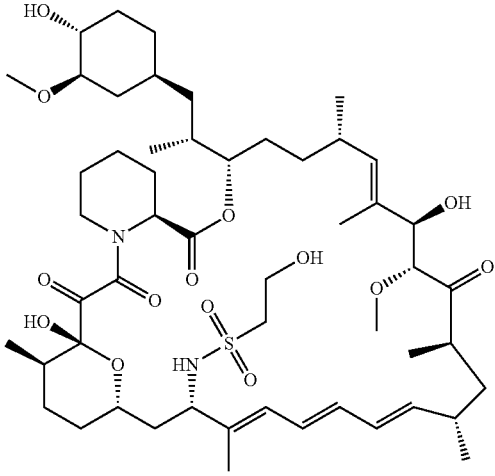 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)CCO)C[C@@H]3CC[C@@H](C)[C@@](O)(O3)C(=O)C(=O)N3CCCC[C@H]3C(=O)O2)CC[C@H]1O] |
| 20 | 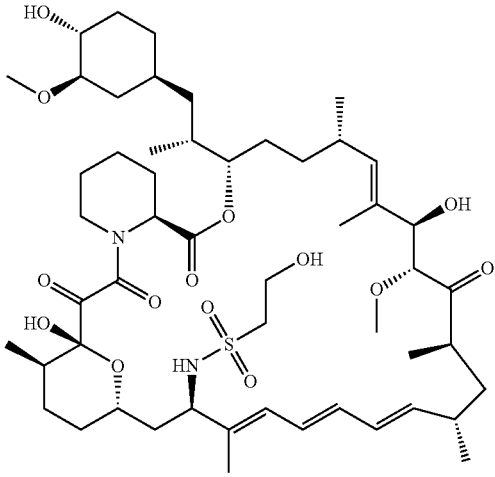 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)CCO)C[C@@H]3CC[C@@H](C)[C@@](O)(O3)C(=O)C(=O)N3CCCC[C@H]3C(=O)O2)CC[C@H]1O] |
| 21 | 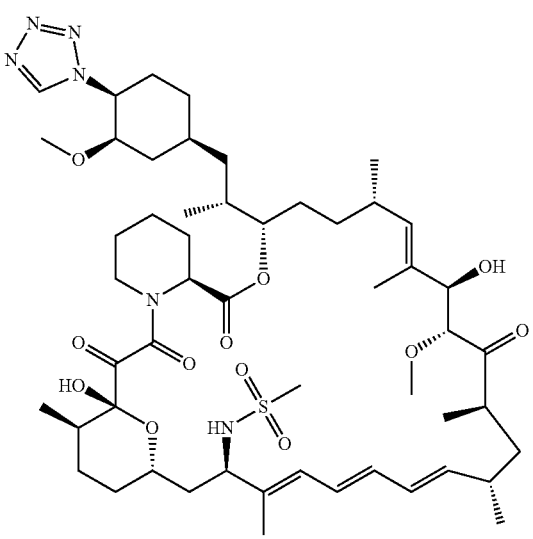 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@@H]1n1cnnn1] |

TABLE 1-continued

| Compound | Structure |
|---|---|
| 22 | 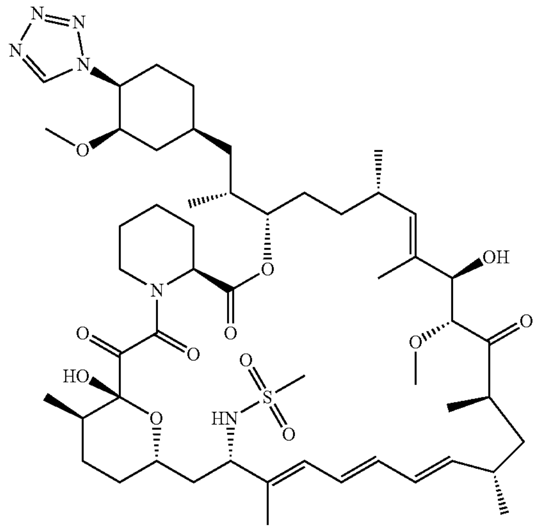 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@@H]1n1cnnn1] |
| 23 | 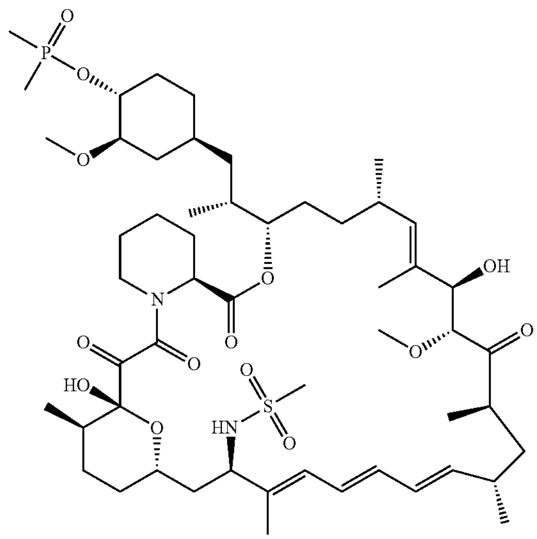 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@H]1OP(C)(C)=O] |
| 24 | 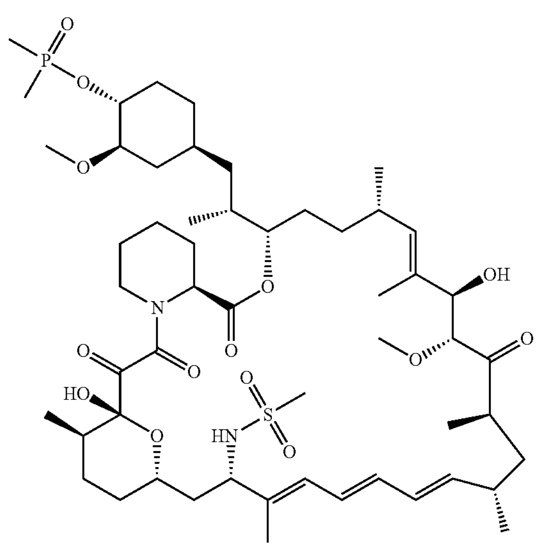 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@H]1OP(C)(C)=O] |

TABLE 1-continued
| Compound | Structure |
|---|---|
| 25 | 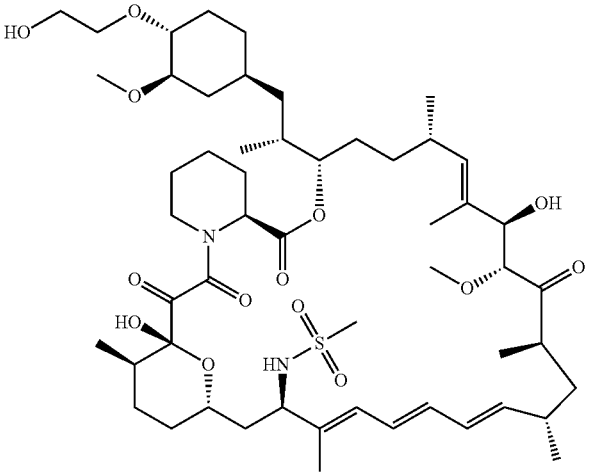 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@H]1OCCO] |
| 26 | 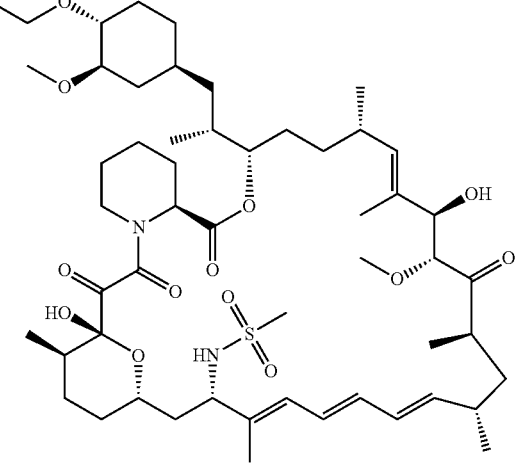 |
| 27 | 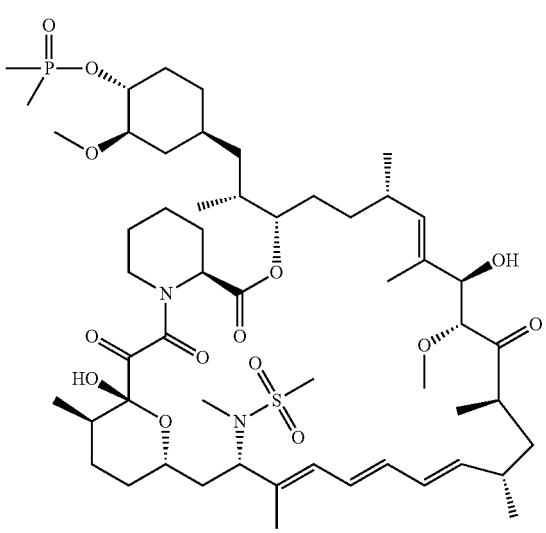 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(C)S(C)(=O)=O)C[C@@H]3CC[C@@H](C)[C@@](O)(O3)C(=O)C(=O)N3CCCC[C@H]3C(=O)O2)CC[C@H]1OP(C)(C)=O] |

TABLE 1-continued
| Compound | Structure |
|---|---|
| 28 | 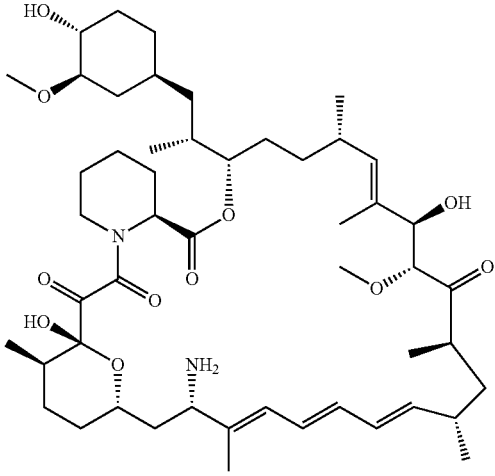 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N)C[C@@H]3CC[C@@H](C)[C@@](O)(O3)C(=O)C(=O)N3CCCC[C@H]3C(=O)O2)CC[C@H]1O] |
| 29 | 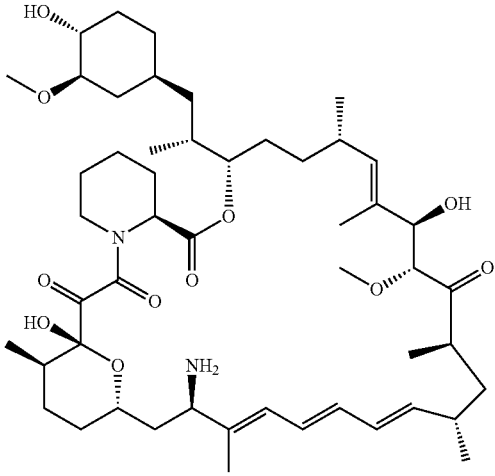 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N)C[C@@H]3CC[C@@H](C)[C@@](O)(O3)C(=O)C(=O)N3CCCC[C@H]3C(=O)O2)CC[C@H]1O] |
| 30 | 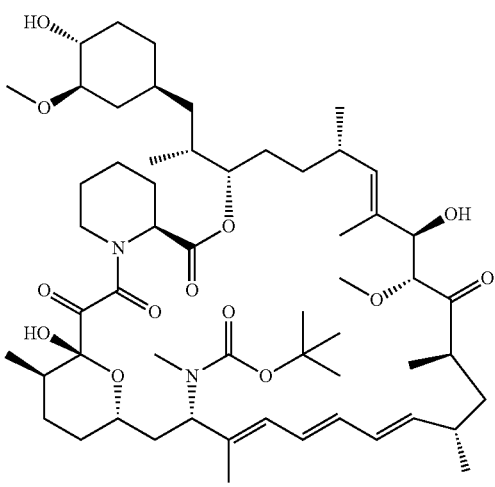 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(C)C(=O)OC(C)(C)C)C[C@@H]3CC[C@@H](C)[C@@](O)(O3)C(=O)C(=O)N3CCCC[C@H]3C(=O)O2)CC[C@H]1O] |

TABLE 1-continued

| Compound | Structure |
|---|---|
| 31 | 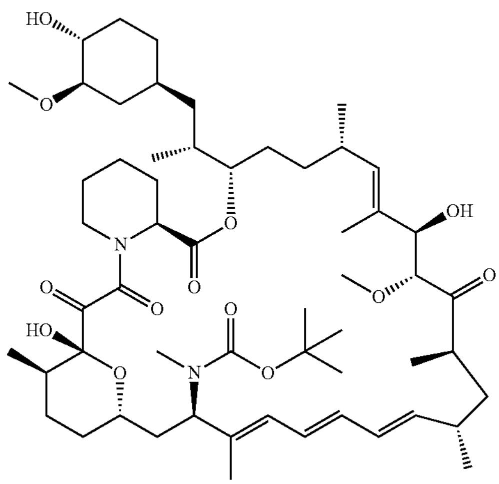 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N(C)C(=O)OC(C)(C)C)C[C@@H]3CC[C@@H](C)[C@@](O)(O3)C(=O)C(=O)N3CCCC[C@H]3C(=O)O2)CC[C@H]1O] |
| 32 | 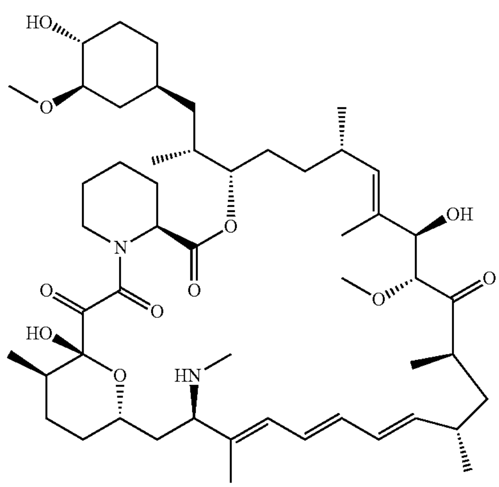 [SMILES: CN[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |
| 33 | 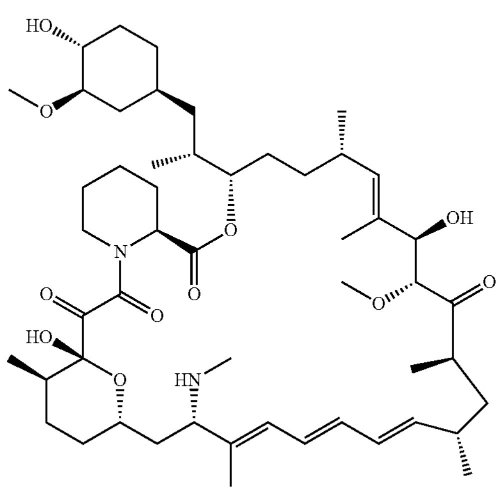 [SMILES: CN[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |

TABLE 1-continued

| Compound | Structure |
|---|---|
| 34 | 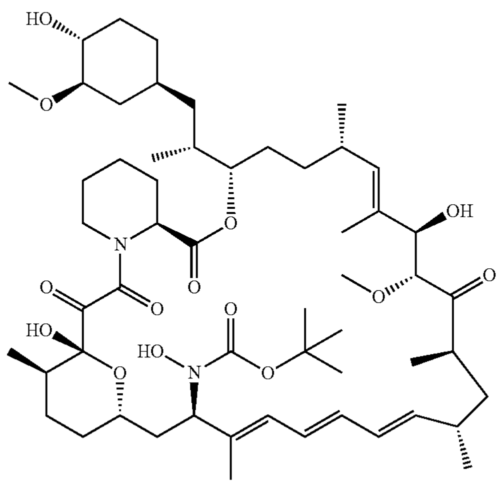 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N(O)C(=O)OC(C)(C)C)C[C@@H]3CC[C@@H](C)[C@@](O)(O3)C(=O)C(=O)N3CCCC[C@H]3C(=O)O2)CC[C@H]1O] |
| 35 | 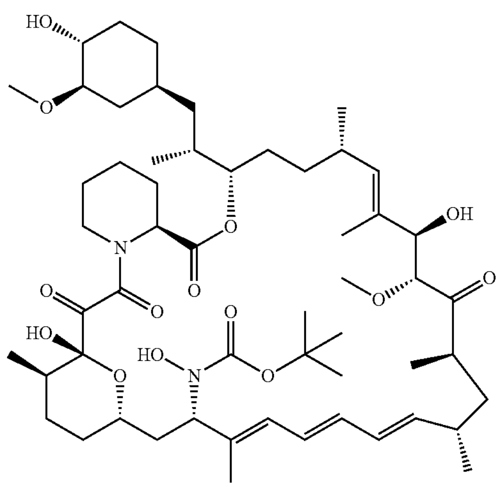 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(O)C(=O)OC(C)(C)C)C[C@@H]3CC[C@@H](C)[C@@](O)(O3)C(=O)C(=O)N3CCCC[C@H]3C(=O)O2)CC[C@H]1O] |
| 36 | 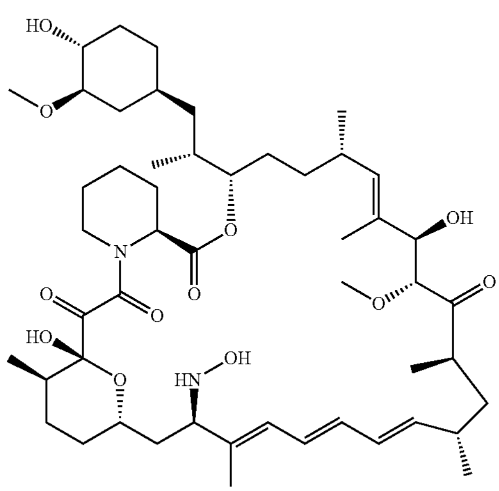 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NO)C[C@@H]3CC[C@@H](C)[C@@](O)(O3)C(=O)C(=O)N3CCCC[C@H]3C(=O)O2)CC[C@H]1O] |

TABLE 1-continued

| Compound | Structure |
|---|---|
| 37 | 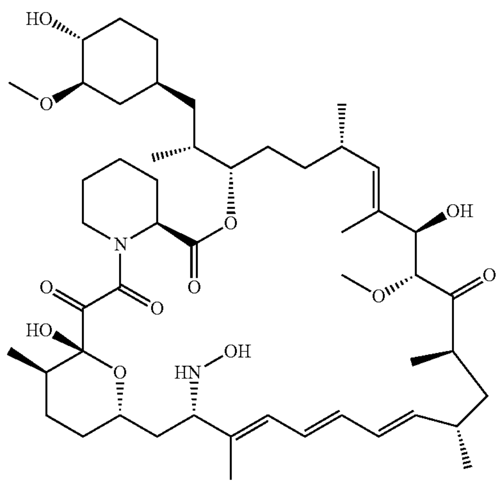 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NO)C[C@@H]3CC[C@@H](C)[C@@](O)(O3)C(=O)C(=O)N3CCCC[C@H]3C(=O)O2)CC[C@H]1O] |
| 38 | 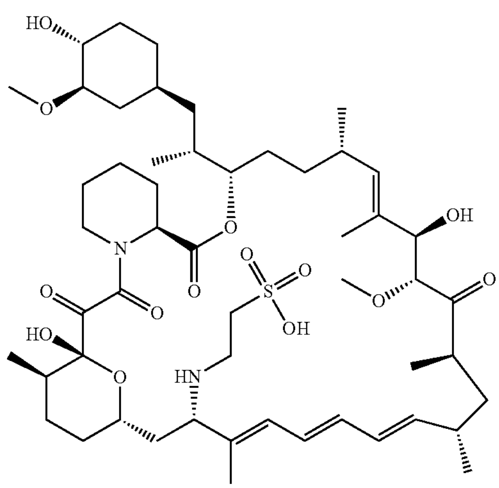 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NCCS(=O)(=O)O)C[C@@H]3CC[C@@H](C)[C@@](O)(O3)C(=O)C(=O)N3CCCC[C@H]3C(=O)O2)CC[C@H]1O] |
| 39 | 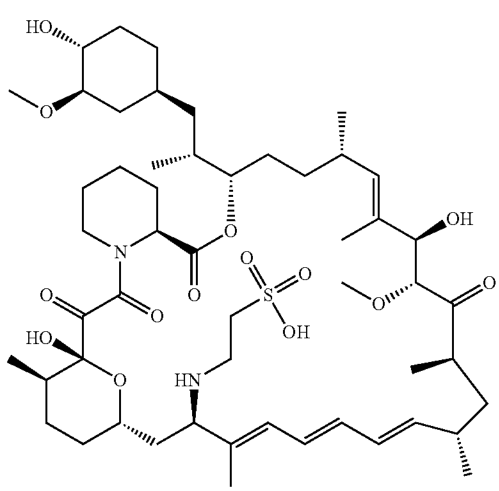 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NCCS(=O)(=O)O)C[C@@H]3CC[C@@H](C)[C@@](O)(O3)C(=O)C(=O)N3CCCC[C@H]3C(=O)O2)CC[C@H]1O] |

TABLE 1-continued

| Compound | Structure |
|---|---|
| 40 | 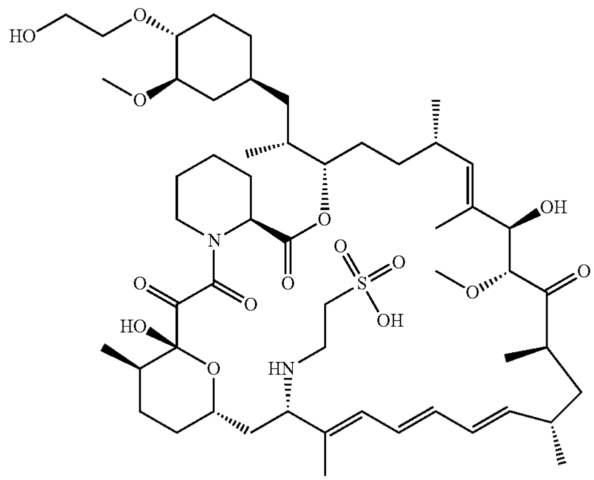 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NCCS(=O)(=O)O)C[C@@H]3CC[C@@H](C)[C@@](O)(O3)C(=O)C(=O)N3CCCC[C@H]3C(=O)O2)CC[C@H]1OCCO] |
| 41 | 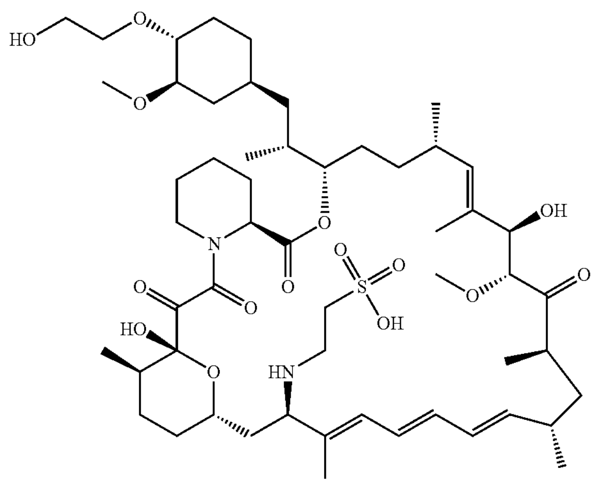 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NCCS(=O)(=O)O)C[C@@H]3CC[C@@H](C)[C@@](O)(O3)C(=O)C(=O)N3CCCC[C@H]3C(=O)O2)CC[C@H]1OCCO] |
| 42 | 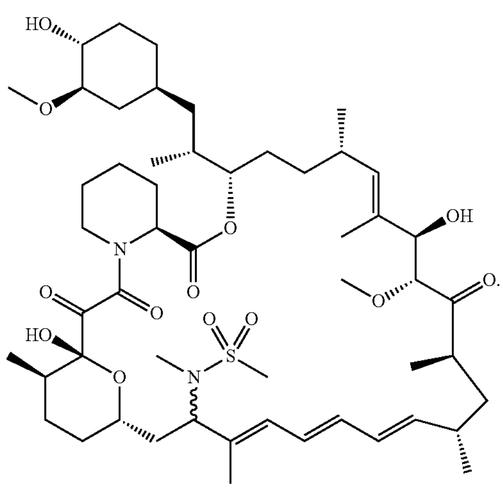 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N(C)S(C)(=O)=O)C[C@@H]3CC[C@@H](C)[C@@](O)(O3)C(=O)C(=O)N3CCCC[C@H]3C(=O)O2)CC[C@H]1O] |

* Absolute sterochemistry at C16 undetermined

Pharmaceutically Acceptable Salts

Pharmaceutically acceptable salts of these compounds are also contemplated for the uses described herein. As used herein, the terms "salt" or "salts" refer to an acid addition or base addition salt of a compound of the disclosure. "Salts" include in particular "pharmaceutical acceptable salts." The term "pharmaceutically acceptable salts" refers to salts that retain the biological effectiveness and properties of the compounds disclosed herein and, which typically are not biologically or otherwise undesirable. In many cases, the compounds disclosed herein are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides a compound of Formula (I), Formula (I)-A, Formula (I)-B, Formula (I)-C, Formula (I)-D, Formula (I)-E, and Formula (I)-F in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, glucepate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Pharmaceutical Compositions

In another aspect, the disclosure provides a pharmaceutical composition comprising one or more compounds of Formula (I), Formula (I)-A, Formula (I)-B, Formula (I)-C, Formula (I)-D, Formula (I)-E, and Formula (I)-F or a pharmaceutically acceptable salt thereof, and one or more pharmaceutically acceptable carrier. The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions of the disclosure are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween®, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. The amount of the compounds of the present disclosure that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Isotopically Labelled Compounds

A compound of Formula (I), Formula (I)-A, Formula (I)-B, Formula (I)-C, Formula (I)-D, Formula (I)-E, and Formula (I)-F or a pharmaceutically acceptable salt thereof is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$, respectively. The disclosure includes various isotopically labeled compounds as defined herein, for example, those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of Formula (I), (Ia) or (Ib) or a pharmaceutically acceptable salt thereof can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example, increased in vivo half-life or reduced dosage requirements or an improvement in therapeutic index. It is understood that deuterium in this context is regarded as a substituent of a compound of Formula (I), Formula (I)-A, Formula (I)-B, Formula (I)-C, Formula (I)-D, Formula (I)-E, and Formula (I)-F or a pharmaceutically acceptable salt thereof. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Dosages

Toxicity and therapeutic efficacy of compounds of the disclosure, including pharmaceutically acceptable salts and deuterated variants, can be determined by standard pharmaceutical procedures in cell cultures or experimental animals. The $LD_{50}$ is the dose lethal to 50% of the population. The ED50 is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed.

Any asymmetric atom (e.g., carbon or the like) of the compound(s) of the disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Diseases and Disorders

Compounds of Formula (I), Formula (I)-A, Formula (I)-B, Formula (I)-C, Formula (I)-D, Formula (I)-E, and Formula (I)-F are useful in the treatment of an age-related disease or disorder selected from:

Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Asthma;
Multi-drug resistance (MDR);
Fungal infections;
Inflammation;
Infection;
Age-related diseases;
Neurodegenerative diseases;
Proliferative disorders, e.g., cancer;
Seizures and seizure related disorders; and
Mitochondrial myopathy and mitochondrial stress.

In another aspect, a compound disclosed herein can be used to treat conditions which have been shown to make age-related diseases more likely, such as settings where there is an increase in senescence inducing cytokines (e.g. IL6).

In another aspect, a compound disclosed herein can be used to treat disorders that include the process of fibrosis and/or inflammation, e.g., liver and kidney disorders. Examples include, liver fibrosis, which occurs in end-stage liver disease; liver cirrhosis; liver failure due to toxicity; non-alcohol-associated hepatic steatosis or NASH; and alcohol-associated steatosis. Another example is kidney fibrosis, which occurs as a result of acute kidney injury, leading to chronic kidney disease. Diabetic nephropathy can induce kidney fibrosis and inflammation. Often kidney disease causes heart failure, as a result of an increase in blood pressure; this can also be associated with cardiac fibrosis.

In another aspect, the compounds of the disclosure can be used to treat cardiac failure. (Buss, S. J. et al. Beneficial effects of Mammalian target of rapamycin inhibition on left ventricular remodeling after myocardial infarction. J Am Coll Cardiol. (2009) 54(25): 2435-46; Buss, S. J. et al. Augmentation of autophagy by mTOR-inhibition in myocardial infarction: When size matters. Autophagy. (2010) 6(2):304-6.

In another aspect, the compounds of the disclosure can be used to treat liver fibrosis in patients who have undergone liver transplants. (Villamil, F. G. et al. Fibrosis progression in maintenance liver transplant patients with hepatitis C recurrence: a randomized study of RAD001 vs. calcineurin inhibitors. Liver Int. (2014) 34(10):1513-21).

Treatment of acute or chronic organ or tissue transplant rejection, include the treatment of recipients of e.g., heart, lung, combined heart-lung, liver, kidney, pancreatic, skin or corneal transplants. Compounds of the disclosure also indicated for the prevention of graft-versus-host disease, such as following bone marrow transplantation.

Transplant vasculopathies include atherosclerosis.

Autoimmune diseases and inflammatory conditions include in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of Formula (I), Formula (I)-A, Formula (I)-B, Formula (I)-C, Formula (I)-D, Formula (I)-E, and Formula (I)-F may be employed include, autoimmune hematological disorders (including e. g. hemolytic anemia, aplastic anemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e. g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

Compounds of the disclosure can also be useful in the treatment of multi-drug resistance (MDR), which includes enhancing the efficacy of other chemotherapeutic agents in the treatment and control of multidrug resistant conditions such as multidrug resistant cancer or multidrug resistant AIDS. MDR is particularly problematic in cancer patients and AIDS patients who will not respond to conventional chemotherapy because the medication is pumped out of the cells by Pgp.

Compounds of the disclosure can also be useful in the treatment of infection, which includes infection by pathogens having Mip or Mip-like factors.

Age-related diseases also include: sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

Neurodegenerative diseases include Huntington's Disease, Parkinson's disease, spinocerebellar ataxia type 3, Alzheimer's disease, motor neuron disease and peripheral neuropathy.

Proliferative disorders include cancer. Such conditions include those listed in U.S. Pat. No. 9,669,032, e.g., renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

Seizures and seizure related disorders include West syndrome, Focal Cortical Dysplasia (FCD), tuberous sclerosis complex (TSC), childhood absence epilepsy, benign focal epilepsies of childhood, juvenile myoclonic epilepsy (JME), temporal lobe epilepsy, frontal lobe epilepsy, refractory epilepsy, Lennox-Gastaut syndrome, occipital lobe epilepsy, Proteus syndrome, hemi-megalencephaly syndrome (HMEG), megalencephaly syndrome (MEG), megalencephaly-capillary malformation (MCAP) and megalencephaly-polymicrogyria-polydactyly-hydrocephalus syndrome (MPPH).

Mitochondrial myopathy and mitochondrial stress are mitochondrial disorders as described in Chinnery, P. F. (2015); EMBO Mol. Med. 7, 1503-1512; Koopman, W. J. et al., (2016); EMBO Mol. Med. 8, 311-327 and Young, M. J., and Yound and Copeland, W. C. (2016); Curr. Opin. Genet. Dev. 38, 52-62.

Treatable conditions which have been shown to make age-related diseases more likely include senescence, e.g., immune senescence. This is diagnosed by (i) an increase in circulating cytokines, such as IL-6, but also by (ii) senescent cells found in muscle, kidney, liver, brain, neurons, liver, pancreas, or the heart; or also (iii) a decline in the efficiency of DNA-repair, which can be shown by an increase in transcription of repetitive elements, including transposon-encoded genes.

Methods of Treatment

The disclosure provides a compound of Formula (I), Formula (I)-A, Formula (I)-B, Formula (I)-C, Formula (I)-D, Formula (I)-E, and Formula (I)-F or a pharmaceutically acceptable salt thereof for treatment of diseases and disorders described herein, e.g., age-related disorders, or diseases and disorders currently approved for treatment using rapalogs, such as RAD001.

In one aspect, the disclosure provides a method for treating a disorder or a disease mediated by the mTOR pathway in a subject in need thereof, the method comprising administering to the subject a therapeutically effective amount of a compound of Formula (I), Formula (I)-A, Formula (I)-B, Formula (I)-C, Formula (I)-D, Formula (I)-E, and Formula (I)-F or a pharmaceutically acceptable salt thereof.

In another aspect, the disclosure provides a method for treating a disease or disorder in a subject, wherein the target tissue, organ, or cells associated with the pathology of the disease or disorder has FKBP12 levels insufficient to inhibit mTORc1, the method comprising administering to the subject in need thereof a therapeutically effective amount of a compound of Formula (I), Formula (I)-A, Formula (I)-B, Formula (I)-C, Formula (I)-D, Formula (I)-E, and Formula (I)-F or a pharmaceutically acceptable salt thereof.

In an embodiment, the compound of Formula (I) or a pharmaceutically acceptable salt thereof has higher affinity binding to FKBP12, FKBP25, FKBP51, and/or FKBP52, e.g., as compared to rapamycin or RAD001.

In an embodiment, the compound of Formula (I) or a pharmaceutically acceptable salt thereof has high affinity binding to FKBP12, FKBP25, FKBP51, and/or FKBP52 sufficient to inhibit mTORc1.

In an embodiment, efficacy of treatment is determined empirically, e.g., as compared to rapamycin or RAD001.

In another aspect, the disclosure provides a method for treating a disease or disorder in a subject having, or determined to have, FKBP12 levels insufficient to inhibit mTORc1, the method comprising administering to the subject in need thereof a therapeutically effective amount of a compound of Formula (I), Formula (I)-A, Formula (I)-B, Formula (I)-C, Formula (I)-D, Formula (I)-E, and Formula (I)-F or a pharmaceutically acceptable salt thereof.

In an embodiment, the compound of Formula (I) or a pharmaceutically acceptable salt thereof has higher affinity binding to FKBP12, FKBP25, FKBP51, and/or FKBP52, e.g., as compared to rapamycin or RAD001.

In an embodiment, the subject has, or is determined to have, FKBP12 levels in the target tissue, organ, or cells insufficient to inhibit mTORc1.

In an embodiment, efficacy of treatment is determined empirically, e.g., as compared to rapamycin or RAD001.

In another aspect, the disclosure provides a method of treating a disease or disorder in a subject having, or previously determined to have, FKBP12 levels sufficient to inhibit mTORc1, the method comprising administering to the subject in need thereof a therapeutically effective amount of a compound of Formula (I) or a pharmaceutically acceptable salt thereof, or a pharmaceutical composition described herein, or a pharmaceutical combination described herein.

In an embodiment, the disease or disorder is selected from sarcopenia, skin atrophy, cherry angiomas, seborrheic keratoses, brain atrophy, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In an embodiment, the disorder is liver fibrosis.

In another aspect, the disclosure provides a method of treating a disease or disorder in a subject in need thereof, the method comprising administering to the subject a therapeutically effective amount of a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, wherein the disorder or disease is selected from:

Acute or chronic organ or tissue transplant rejection;
Transplant vasculopathies;
Smooth muscle cell proliferation and migration leading to vessel intimal thickening, blood vessel obstruction, obstructive coronary atherosclerosis, restenosis;
Autoimmune diseases and inflammatory conditions;
Asthma;
Multi-drug resistance (MDR);
Fungal infections;
Inflammation;
Infection;
Age-related diseases;
Neurodegenerative diseases;
Proliferative disorders, in particular cancer;
Seizures and seizure related disorders; and
Mitochondrial myopathy and mitochondrial stress.

In an embodiment, the disorder is a disorder that includes the process of fibrosis and/or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis.

In an embodiment, the kidney fibrosis occurs as a result of acute kidney injury.

In an embodiment, the kidney disorder is chronic kidney disorder.

In an embodiment, the kidney disorder is diabetic nephropathy.

In another aspect, the disclosure provides a method of treating an age-related disorder or disease in a subject in need thereof, the method comprising administering to the subject a therapeutically effective amount of a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, wherein the disorder or disease is selected from: sarcopenia, skin atrophy, cherry angiomas, seborrheic keratoses, brain atrophy, atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes including complications stemming from diabetes, such as kidney failure, blindness and neuropathy.

In another aspect, the disclosure provides a method of treating cancer in a subject, the method comprising administering to the subject a therapeutically effective amount of a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof.

In an embodiment, the method further comprises a PD-1/PDL-1 inhibitor.

In an embodiment, the cancer is selected from renal cancer, renal cell carcinoma, colorectal cancer, uterine sarcoma, endometrial uterine cancer, endometrial cancer, breast cancer, ovarian cancer, cervical cancer, gastric cancer, fibrosarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, and neck cancer.

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use as a medicament.

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use in the prevention or treatment of a disorder or disease mediated by the mTOR pathway.

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use in the prevention or treatment of a disorder or disease selected from:
  Acute or chronic organ or tissue transplant rejection;
  Transplant vasculopathies;
  Smooth muscle cell proliferation and migration leading to vessel intimal thickening, blood vessel obstruction, obstructive coronary atherosclerosis, restenosis;
  Autoimmune diseases and inflammatory conditions;
  Asthma;
  Multi-drug resistance (MDR);
  Fungal infections;
  Inflammation;
  Infection;
  Age-related diseases;
  Neurodegenerative diseases;
  Proliferative disorders, in particular cancer;
  Seizures and seizure related disorders; and
  Mitochondrial myopathy and mitochondrial stress.

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use in the prevention or treatment of a disorder or disease that includes the process of fibrosis and/or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis, which occurs as a result of acute kidney injury.

In an embodiment, the kidney disorder is chronic kidney disorder.

In an embodiment, the kidney disorder is diabetic nephropathy.

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use in the treatment of an age-related disorder or disease selected from sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability (e.g., frailty), cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use in the treatment of cancer.

In another aspect, the disclosure provides a compound of Formula (I), Formula (I)-A, Formula (I)-B, Formula (I)-C, Formula (I)-D, Formula (I)-E, and Formula (I)-F or a pharmaceutically acceptable salt thereof, a pharmaceutical composition comprising a compound of Formula (I), Formula (I)-A, Formula (I)-B, Formula (I)-C, Formula (I)-D, Formula (I)-E, and Formula (I)-F or a pharmaceutically acceptable salt thereof, or a pharmaceutical combination comprising a compound of Formula (I), Formula (I)-A, Formula (I)-B, Formula (I)-C, Formula (I)-D, Formula (I)-E, and Formula (I)-F or a pharmaceutically acceptable salt thereof, for use in the treatment of renal cancer, renal cell carcinoma, colorectal cancer, uterine sarcoma, endometrial uterine cancer, endometrial cancer, breast cancer, ovarian cancer, cervical cancer, gastric cancer, fibro-sarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament.

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament for the treatment of a disorder or disease mediated by the mTOR pathway.

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament for the treatment of a disorder or disease selected from:
  Acute or chronic organ or tissue transplant rejection;
  Transplant vasculopathies;
  Smooth muscle cell proliferation and migration leading to vessel intimal thickening, blood vessel obstruction, obstructive coronary atherosclerosis, restenosis;
  Autoimmune diseases and inflammatory conditions;
  Asthma;
  Multi-drug resistance (MDR);
  Fungal infections;
  Inflammation;
  Infection;
  Age-related diseases;
  Neurodegenerative diseases;
  Proliferative disorders, e.g., cancer;
  Seizures and seizure related disorders; and
  Mitochondrial myopathy and mitochondrial stress.

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament for the treatment of a disorder or disease that includes the process of fibrosis or inflammation.

In an embodiment, the disorder is selected from liver and kidney disorders.

In an embodiment, the liver disorder is selected from: liver fibrosis, which occurs in end-stage liver disease; liver cirrhosis; liver failure due to toxicity; non-alcohol-associated hepatic steatosis or NASH; and alcohol-associated steatosis.

In an embodiment, the kidney disorder is kidney fibrosis, which occurs as a result of acute kidney injury.

In an embodiment, the kidney disorder is chronic kidney disorder.

In an embodiment, the kidney disorder is diabetic nephropathy.

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament for the manufacture of a medicament for the prevention or treatment of an age-related disorder or disease selected from sarcopenia, skin atrophy, cherry angiomas, seborrheic keratoses, brain atrophy (also referred to as dementia), atherosclerosis, arteriosclerosis, pulmonary emphysema, osteoporosis, osteoarthritis, high blood pressure, erectile dysfunction, cataracts, macular degeneration, glaucoma, stroke, cerebrovascular disease (strokes), chronic kidney disease, diabetes-associated kidney disease, impaired hepatic function, liver fibrosis, autoimmune hepatitis, endometrial hyperplasia, metabolic dysfunction, renovascular disease, hearing loss, mobility disability, cognitive decline, tendon stiffness, heart dysfunction such as cardiac hypertrophy and/or systolic and/or diastolic dysfunction and/or hypertension, heart dysfunction which results in a decline in ejection fraction, immune senescence, Parkinson's disease, Alzheimer's disease, cancer, immune-senescence leading to cancer due to a decrease in immune-surveillance, infections due to an decline in immune-function, chronic obstructive pulmonary disease (COPD), obesity, loss of taste, loss of olfaction, arthritis, and type II diabetes (including complications stemming from diabetes, such as kidney failure, blindness and neuropathy).

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament for the manufacture of a medicament for the prevention or treatment of cancer.

In another aspect, the disclosure provides a use of a compound of Formula (I), Formula (I)-A, Formula (I)-B, Formula (I)-C, Formula (I)-D, Formula (I)-E, and Formula (I)-F or a pharmaceutically acceptable salt thereof for the manufacture of a medicament for the manufacture of a medicament for the treatment of renal cancer, renal cell carcinoma, colorectal cancer, uterine sarcoma, endometrial uterine cancer, endometrial cancer, breast cancer, ovarian cancer, cervical cancer, gastric cancer, fibro-sarcoma, pancreatic cancer, liver cancer, melanoma, leukemia, multiple myeloma, nasopharyngeal cancer, prostate cancer, lung cancer, glioblastoma, bladder cancer, mesothelioma, head cancer, rhabdomyosarcoma, sarcoma, lymphoma, or neck cancer.

Methods of Making a Compound of Formula (I)

In another aspect, the disclosure provides a method of making a compound of the disclosure according to Schemes 1, 2, and 3.

Scheme 1

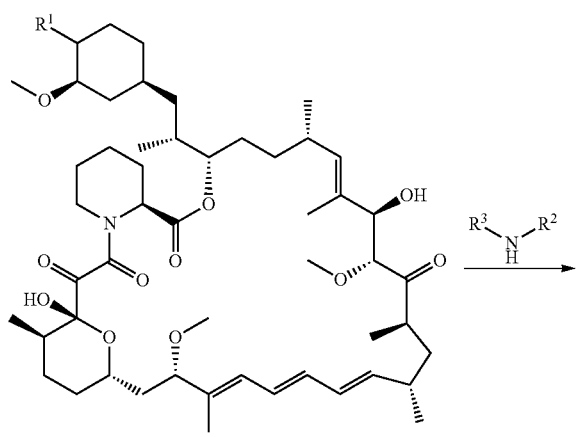

C32-deoxy repamycin (Intermediate 1) wherein R¹ is OH

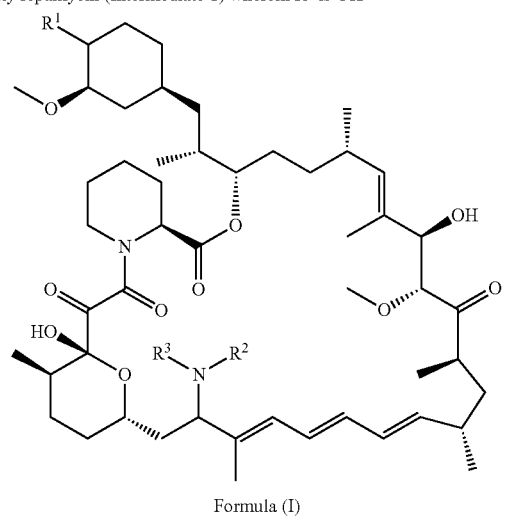

Formula (I)

A compound of Formula (I), in which $R^2$ and $R^3$ are as defined in Formula (I), may be obtained by reacting C32-deoxy rapamycin (Intermediate 1) with $(R^2)(R^3)NH$, wherein $R^2$ and $R^3$ are as defined in Formula (I), in the presence of a suitable reagent for a substitution reaction, e.g. zinc(II) chloride, in the presence of a suitable solvent, e.g. dichloromethane. Suitable conditions are as follows:

1) $(R^2)(R^3)NH$, p-toluenesulphonic acid-$H_2O$, dichloromethane, room temperature
2) $(R^2)(R^3)NH$, trifluoroacetic acid, −40° C., dichloromethane (see EP1212331B1)
3) $(R^2)(R^3)NH$, 5M $LiClO_4$, $Et_2O$ (0.1M), room temperature (see TL, 1995, 43, 7823)
4) $(R^2)(R^3)NH$, $Cp_2HfCl_2$—$AgClO_4$ (Suzuki's catalyst), 4 A MS, dichloromethane, room temperature (see TL, 1995, 43, 7823)
5) $(R^2)(R^3)NH$, $BF_3$—$OEt_2$ or $Zn(OTf)_2$, THF, 0° C. (see TL, 1994, 37, 6835)
6) $(R^2)(R^3)NH$, $ZnCl_2$, dichloromethane, 0° C. (see JOC, 1994, 59, 6512).
7) $(R^2)(R^3)NH$, Methanesulfonic acid, dichloromethane, room temperature
8) $(R^2)(R^3)NH$, Phosphoric acid, dichloroemethane, room temperature
9) $(R^2)(R^3)NH$, Polyphosphoric acid, dichloromethane, room temperature C32-deoxy rapamycin used as the starting material may be prepared by methods known in the art, e.g. as described in WO2007/085400.

Scheme 2

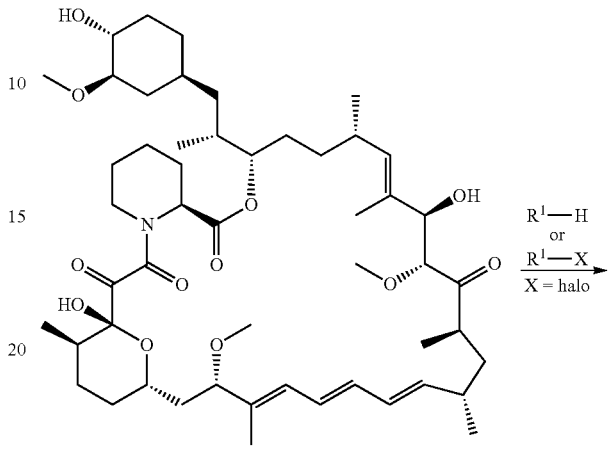

C32-deoxy rapamycin (Intermediate 1)

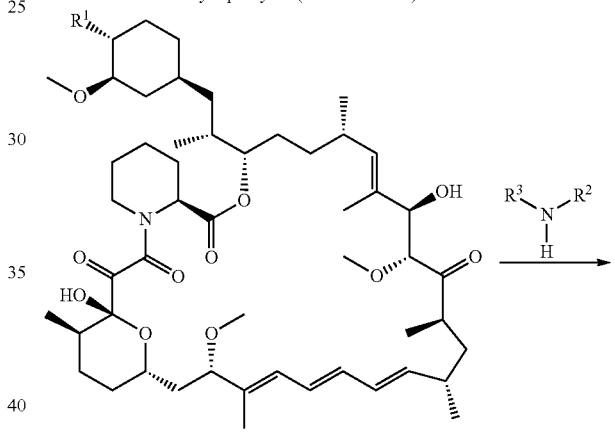

Intermediate 1-A

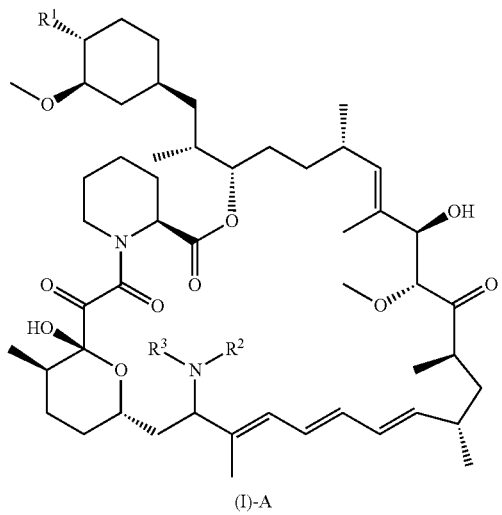

(I)-A

A compound of Formula (I)-A, wherein $R^1$ is —$OR^a$; $R^a$ is selected from the group consisting of H, $P(O)(R^b)_2$, $C_{1-6}$alkyl, and $C_{1-6}$hydroxyalkyl; and $R^2$ and $R^3$ are as defined in Formula (I), may be obtained by reacting Intermediate 1 with R¹—H or R¹—X followed by reaction with (R²)(R³)NH. In an embodiment, Intermediate 1 is reacted with R₁—H or R¹—X under alkylation, phosphination or esterification conditions to provide Intermediate 1-A. In an embodiment, Intermediate 1-A is reacted with (R²)(R³)NH under substitution reaction conditions, e.g., as provided herein, to afford a compound of Formula (I)-A. A compound of Formula (I)-C and Formula (I)-D can also be prepared in an analogous manner to the synthetic route shown in Scheme 2.

Scheme 3

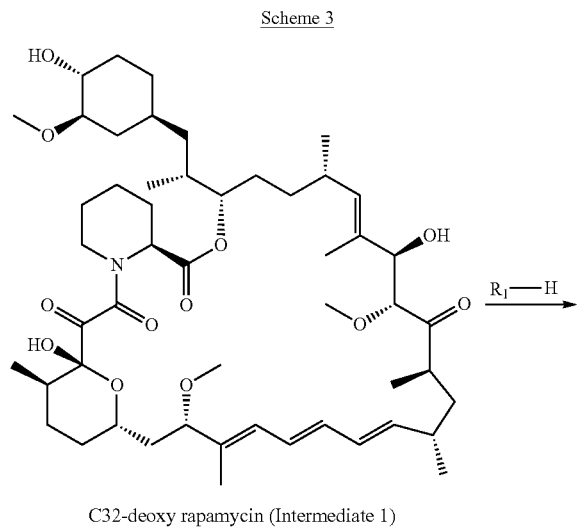

C32-deoxy rapamycin (Intermediate 1)

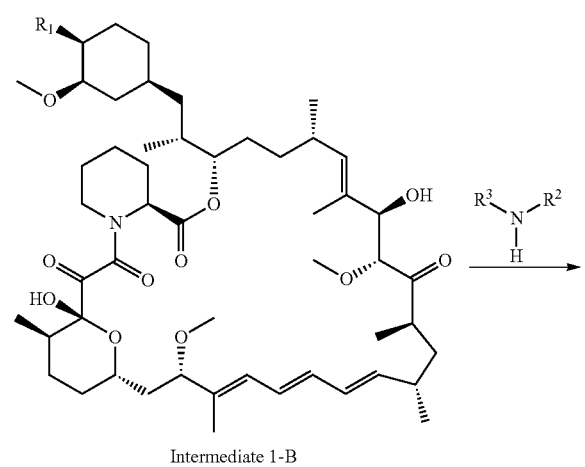

Intermediate 1-B

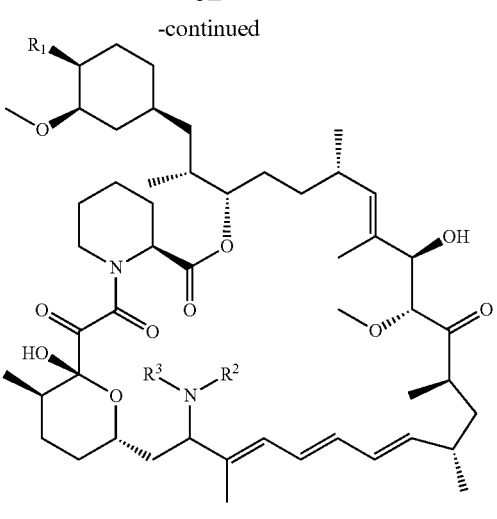

(I)-B

A compound of Formula (I)-B, wherein R¹ is

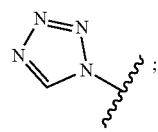 [SMILES: *n1cnnn1]

and R² and R³ are as defined in Formula (I), may be obtained by reacting Intermediate 1-B with R¹—H followed by reaction with (R²)(R³)NH. In an embodiment, Intermediate 1-B is activated and reacted under nucleophilic conditions to provide Intermediate 1-B. In an embodiment, Intermediate 1-B is reacted with (R²)(R³)NH under substitution reaction conditions, e.g., as provided herein, to afford the compound of Formula (I)-B. A compound of Formula (I)-E and Formula (I)-F can also be prepared in an analogous manner to the synthetic route shown in Scheme 3.

EXAMPLES

The disclosure sets for the following examples. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Rapamycin and its derivatives, for example, compounds of formula (I), exist as a solvent and pH dependent equilibrium of six-membered and seven-membered hemi-ketal forms shown below as E and F (Schemes 4 and 5). See *The Journal of Antibiotics* (Tokyo) (1991) 44(6):688-90; and *Tetrahedron Letters* (1992) 33(33):4139-4142. Rapamycin and its derivatives also exist as a mixture of cis- and trans-amides shown below as E, H, J and K (Schemes 4 and 5). [See Mierke, D. F., Schrieder, P., Karuso, P. and Kessler, H. (1991), Conformational Analysis of the cis- and trans-Isomers of FK506 by NMR and Molecular Dynamics. *Helvetica Chinica Acta*, 74: 1027-1047.] The NMR characterization data shown in the examples corresponds only to the major equilibrium form observed under the reported deutero solvent conditions.

Scheme 4

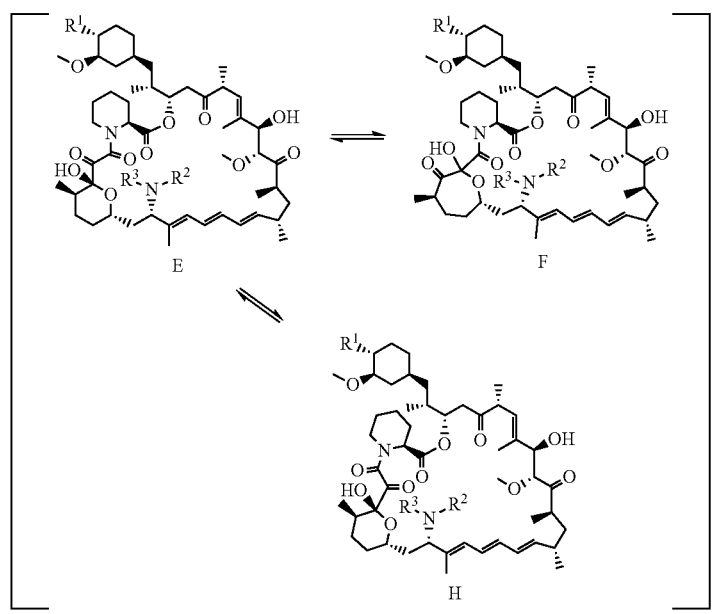

wherein:

$R^1$ is —$OR^a$;

$R^a$ is selected from the group consisting of H, $P(O)(R^b)_2$, $C_{1-6}$alkyl, and $C_{1-6}$hydroxyalkyl;

$R^2$ and $R^3$ are each independently selected from the group consisting of H, $C_{1-6}$alkyl, $OR^b$, —$C_{0-6}$alkylene-$SO_2R^4$, and —$C(O)OR^5$;

each $R^b$ is independently selected from the group consisting of H and $C_{1-6}$alkyl;

$R^4$ is —$OR^5$, $C_{1-6}$alkyl, $C_{1-6}$haloalkyl, heteroC$_{1-6}$alkyl, $C_{1-6}$hydroxyalkyl, $C_{3-8}$cycloalkylC$_{0-6}$alkyl; and $R^5$ is H or $C_{1-6}$alkyl.

Scheme 5

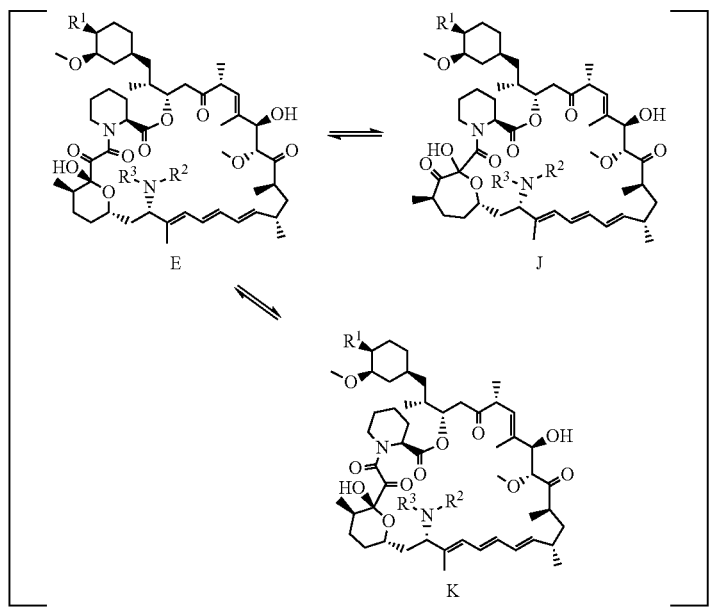

wherein:

R₁ is heteroaryl, e.g., a 5-membered heteroaryl, e.g.,

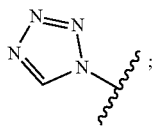

;

R² and R³ are each independently selected from the group consisting of H, $C_{1-6}$alkyl, $OR^b$, —$C_{0-6}$alkylene-SO₂R⁴, and —C(O)OR⁵;

each $R^b$ is independently selected from the group consisting of H and $C_{1-6}$alkyl;

R⁴ is —OR⁵, $C_{1-6}$alkyl, $C_{1-6}$haloalkyl, heteroC$_{1-6}$alkyl, $C_{1-6}$hydroxyalkyl, $C_{3-8}$cycloalkylC$_{0-6}$alkyl; and R⁵ is H or $C_{1-6}$alkyl.

In an embodiment, compounds of formula (I), formula (I)-A and formula (I)-B exist as a solvent and pH dependent equilibrium of six-membered and seven-membered hemiketal forms shown below as E-1 and F-1 (Scheme 6). In an embodiment, compounds of formula (I), formula (I)-A and formula (I)-B exist as a mixture of cis- and trans-amides E-1 and H-1.

Scheme 6

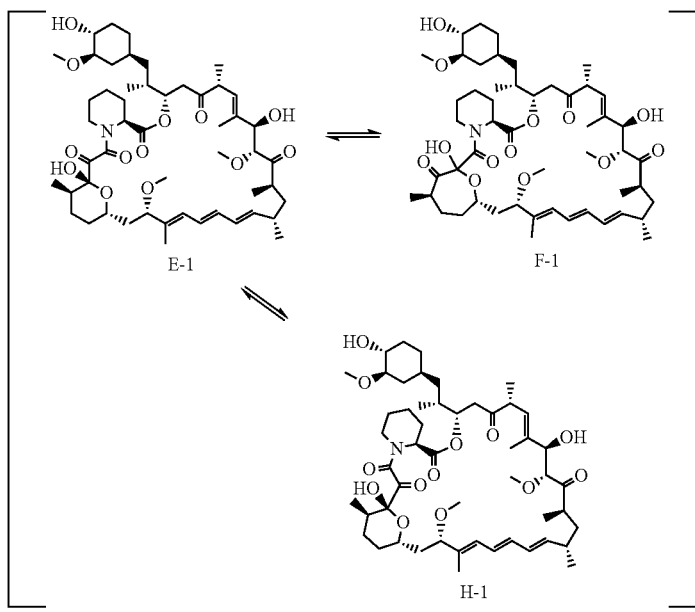

$R^1$ is —$OR^a$;

$R^a$ is selected from the group consisting of H, $P(O)(R^b)_2$, $C_{1-6}$alkyl, and $C_{1-6}$hydroxyalkyl;

$R^2$ and $R^3$ are each independently selected from the group consisting of H, $C_{1-6}$alkyl, $OR^b$, —$C_{0-6}$alkylene-$SO_2R^4$, and —$C(O)OR^5$;

each $R^b$ is independently selected from the group consisting of H and $C_{1-6}$alkyl;

$R^4$ is —$OR^5$, $C_{1-6}$alkyl, $C_{1-6}$haloalkyl, heteroC$_{1-6}$alkyl, $C_{1-6}$hydroxyalkyl, $C_{3-8}$cycloalkylC$_{0-6}$alkyl; and $R^5$ is H or $C_{1-6}$alkyl.

Preparation of Compounds

Compounds of the disclosure can be prepared as described in the following Examples.

LIST OF ABBREVIATIONS

The following abbreviations used herein below have the corresponding meanings:

A angstrom
d doublet
dd doublet of doublets
DCM dichloromethane
DMSO dimethylsulfoxide
ESIMS electrospray ionisation mass spectrometry
EtOAc ethyl acetate
eq equivalent
FA formic acid
HSQC NMR Heteronuclear Single Quantum Coherence nuclear magnetic resonance
HPLC high performance liquid chromatography
Hz hertz
MeCN acetonitrile
MeOH methanol
M molar
m multiplet
mg milligram
MHz megahertz
mL milliliter(s)
mmol millimole
NMR nuclear magnetic resonance
PEI Polyethylenimine
PPU Propyl-pyridyl-urea
q quartet
μL microliter(s)
μM micromolar
s singlet
SFC Supercritical Fluid Chromatography
t triplet Methods Employed in the Purification of the Examples Purification of intermediates and final products was carried out via either normal or reverse phase chromatography.

Flash Chromatography

Normal phase chromatography was carried out using prepacked SiO$_2$ cartridges (e.g., RediSep® Rf columns from Teledyne Isco, Inc.) eluting with gradients of appropriate solvent systems (e.g., hexanes and ethyl acetate; DCM and MeOH; or unless otherwise indicated).

Reverse phase chromatography was carried out using prepacked C18 cartridges (e.g., RediSep® Rf columns from Teledyne Isco, Inc.) eluting with gradients of appropriate solvent systems (e.g., acetonitrile and water; or unless otherwise indicated).

SFC was carried out using the methods described below:

Method 1: Reprospher PEI 5 μm (100 A) column (30×250 mm); CO$_2$/MeOH

Method 2: Princeton PPU 5 μm (100 A) column (30×250 mm); CO$_2$/MeOH

Method 3: Kinetex BiPhenyl 5 μm (100 A) column (30×250 mm); CO$_2$/MeOH Gradients were selected based on analytical separation.

Reverse phase preparative HPLC was carried out using the methods described below:

Method 1: Phenomenex Luna C18; 5 μm column (30×250 mm); 0.1% formic acid and 5% water in acetonitrile; 0.1% formic acid and 5% acetonitrile in water. Gradients were selected based on analytical separation.

Method 2: YMC Actus Triart C18; 5 μm column (20×150 mm); acetonitrile/water. Gradients were selected based on analytical separation.

Method 3: YMC Actus Triart C18ExRS; 5 μm column (20×150 mm); 0.1% formic acid and 5% water in acetonitrile; 0.1% formic acid and 5% acetonitrile in water. Gradients were selected based on analytical separation.

Method 4: YMC Actus Triart C8; 5 μm column (20×150 mm); 0.1% formic acid and 5% water in acetonitrile; 0.1% formic acid and 5% acetonitrile in water. Gradients were selected based on analytical separation.

Preparation of Intermediates

Preparation of Intermediates 1 Through 9

Intermediate 1: C32-deoxo-rapamycin

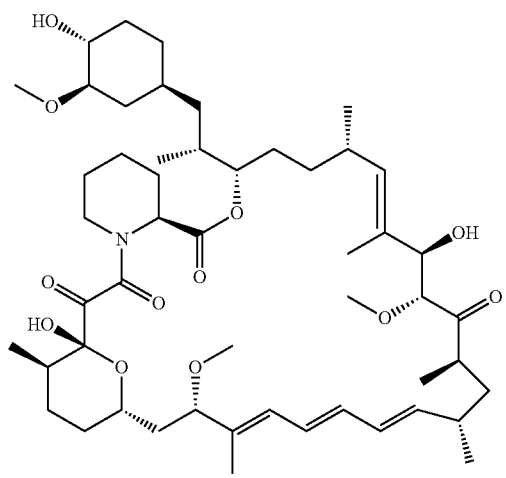

Intermediate 1

Intermediate 1 was prepared according to procedures known in the literature including those disclosed in WO2007/085400 A1, each of which is incorporated by reference herein in its entirety.

Intermediate 2

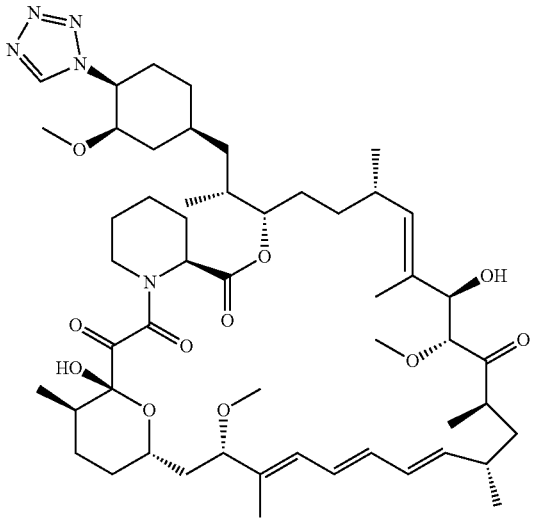

Intermediate 1 (4.37 g, 4.86 mmol) was dissolved in anhydrous dichloromethane (20 mL). Anhydrous toluene was added (20 mL). The reaction mixture was evaporated to dryness on a rotary evaporator. This azeotropic drying process was repeated twice more.

The dried starting material was combined with 2,6-lutidine (1.39 ml, 11.9 mmol) in anhydrous dichloromethane (58 mL). The flask was capped and the mixture was twice vacuum purged with nitrogen. The mixture was chilled to −30° C. in an acetonitrile/dry-ice bath.

Triflic anhydride (1.20 ml, 7.16 mmol) was added dropwise via syringe over a period of four minutes. The reaction mixture was stirred at −30° C. for 30 minutes. The reaction mixture was transferred to a 0° C. ice-water bath and was stirred for 20 minutes at 0° C.

The reaction mixture was placed on the rotary evaporator and was concentrated without heat. Isopropyl acetate (22 mL) was added. Tetrazole (1.17 g, 16.7 mmol) was added in one portion. The flask was quickly capped and was twice vacuum purged with nitrogen. N,N-diisopropylethylamine (4.18 ml, 23.9 mmol) was added via syringe over a period of one minute. The reaction mixture was stirred overnight at room temperature.

The reaction mixture was concentrated on a rotary evaporator. The concentrate was purified by normal-phase silica gel flash column chromatography (0 to 40% acetone-heptane gradient elution, 80 g silica column, TLC 40% acetone-heptane, visualize under UV).

The second eluting peak fractions (as determined by UV absorbance at 279 nm) were pooled and concentrated to give Intermediate 2 (2.19 g, 2.30 mmol, 47.4% yield) as a white solid.

Intermediate 2: ESIMS [M+NH4]$^+$ 969.8, ESIMS [M−H]$^−$ 950.8.

$^1$H NMR (400 MHz, DMSO-$d_6$) δ 9.33 (d, J=6.4 Hz, 1H), 6.58-6.41 (m, 2H), 6.35-6.14 (m, 2H), 6.09-5.98 (m, 1H), 5.55-5.43 (m, 1H), 5.19 (m, 1H), 5.05 (m, 1H), 5.00-4.93 (m, 1H), 4.87-4.79 (m, 1H), 4.67-4.56 (m, 1H), 3.98-3.87 (m, 1H), 3.87 (d, J=6.9 Hz, 1H), 3.61 (m, 2H), 3.55 (dd, J=11.8, 1.9 Hz, 1H), 3.49-3.38 (m, 1H), 3.31-3.17 (m, 4H), 3.10 (m, 4H), 3.04 (s, 3H), 2.88-2.75 (m, 1H), 2.29-2.09 (m, 3H), 2.07-1.86 (m, 3H), 1.88-1.60 (m, 9H), 1.59-1.44 (m, 7H), 1.43-1.01 (m, 11H), 0.96 (t, J=7.1 Hz, 5H), 0.95-0.77 (m, 7H), 0.72 (m, 4H).

Intermediate 3

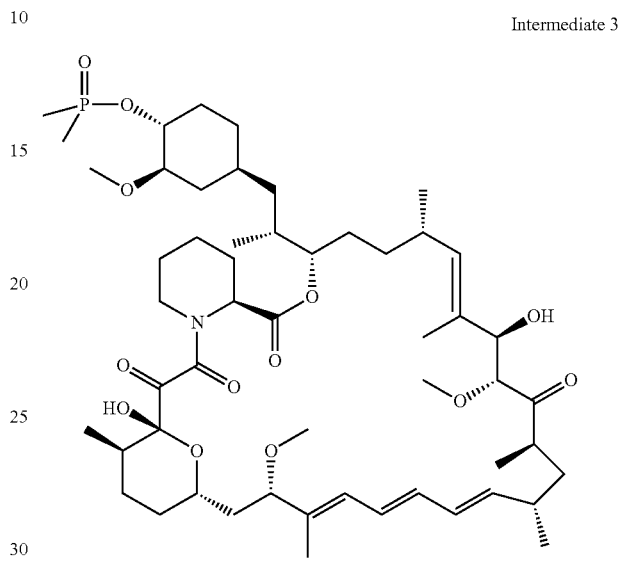

Intermediate 1 (0.233 g, 0.259 mmol) was combined with 2,6-di-tert-butyl-4-methylpyridine (0.424 g, 2.07 mmol) in anhydrous dichloromethane (2.6 mL). The reaction mixture was vacuum purged once with nitrogen. The reaction mixture was chilled to 0° C. in an ice-water bath. Solid dimethylphosphinic chloride (0.145 g, 1.29 mmol) was added in one portion. The reaction mixture was stirred at 0° C. for 80 minutes.

The reaction was diluted with saturated aqueous NaHCO$_3$ and was extracted several times with EtOAc. The organic extracts were combined, dried over Na$_2$SO$_4$, decanted and concentrated to give a colorless tar crude product (0.77 g).

The crude product was purified by silica gel flash column chromatography (0-80% Acetone-heptane gradient elution, 24 g silica column, TLC in 80% EtOAc-heptane, visualize under UV). Product containing fractions were pooled and concentrated to give Intermediate 3 (0.09 g, 0.09 mmol, 34.4% yield) as a white solid.

Intermediate 3: ESIMS [M+NH4]$^+$ 993.7, ESIMS [M−H]$^−$ 974.7.

HRMS: Calculated: 999.5812 (Na$^+$ adduct). Found: 999.5807.

$^1$H NMR (600 MHz, Chloroform-d) δ 6.47-6.26 (m, 2H), 6.22-6.08 (m, 1H), 6.02-5.83 (m, 1H), 5.54 (m, 1H), 5.35-5.26 (m, 1H), 5.21 (m, 1H), 4.85-4.76 (m, 1H), 4.12 (m, 2H), 3.93-3.81 (m, 1H), 3.67 (t, J=7.7 Hz, 1H), 3.62 (d, J=6.7 Hz, 1H), 3.60-3.53 (m, 1H), 3.53-3.44 (m, 1H), 3.42-3.36 (m, 3H), 3.32 (m, 3H), 3.28-3.18 (m, 1H), 3.13 (m, 3H), 3.05 (m, 1H), 2.82 (m, 1H), 2.42-2.21 (m, 3H), 2.16-2.08 (m, 3H), 1.99 (m, 1H), 1.95-1.83 (m, 1H), 1.83-1.72 (m, 4H), 1.71-1.57 (m, 9H), 1.57-1.43 (m, 12H), 1.39 (m, 1H), 1.34-1.20 (m, 4H), 1.20-1.10 (m, 1H), 1.05 (m, 4H), 1.00 (d, J=6.5 Hz, 3H), 0.95 (dd, J=6.6, 2.1 Hz, 3H), 0.92 (d, J=6.6 Hz, 3H), 0.91-0.84 (m, 4H), 0.77 (q, J=12.1 Hz, 1H).

Intermediate 4

Intermediate 4

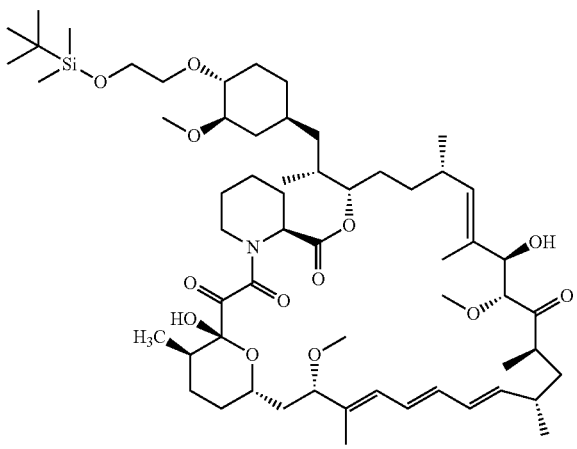

2-((tert-butyldimethylsilyl)oxy)ethanol (0.471 g, 2.67 mmol) was dissolved in anhydrous toluene (0.95 mL) in a reaction vial. The vial was capped and then was vacuum purged with nitrogen. N,N-diisopropylethylamine (DIPEA) (0.490 ml, 2.81 mmol) was added via syringe. The mixture was chilled to 0° C. in an ice-water bath. Triflic anhydride (Tf$_2$O) (0.438 ml, 2.59 mmol) was added dropwise at 0° C. over a period of about two minutes. The reaction mixture was stirred at 0° C. for 30 minutes.

The vial was lifted out of the cold bath. DIPEA (0.490 ml, 2.81 mmol) was added via syringe. The vial was opened and solid Intermediate 1 (0.600 g, 0.667 mmol) was quickly added in one portion. The vial was quickly recapped and the mixture was vacuum purged with nitrogen. Toluene (0.5 mL) was added.

The reaction was stirred at 40° C. under nitrogen overnight. The reaction was diluted with saturated aqueous NaHCO$_3$. The quenched mixture was extracted with EtOAc five times. The organic extracts were combined, dried over Na$_2$SO$_4$, vacuum filtered through celite and concentrated to afford a waxy white solid crude product.

The crude product was purified by silica gel flash column chromatography (0-35% acetone-heptane, gradient elution, 40 g silica column, TLC in 35% acetone-heptane, visualize under UV) to give the desired Intermediate 4 (0.245 g, 0.231 mmol, 34.7% yield) as a glass which was immediately used "as is" in the following step.

Intermediate 4: ESIMS [M+NH4]$^+$ 1076.1, ESIMS [M−H]$^−$ 1056.0.

Intermediate 5: C16-(1,1-dioxido-1,2-thiazetidin-2-yl)-C32-deoxo-rapamycin (Diastereomer 1)

Intermediate 6: C16-(1,1-dioxido-1,2-thiazetidin-2-yl)-C32-deoxo-rapamycin (Diastereomer 2)

Intermediates 5 and 6

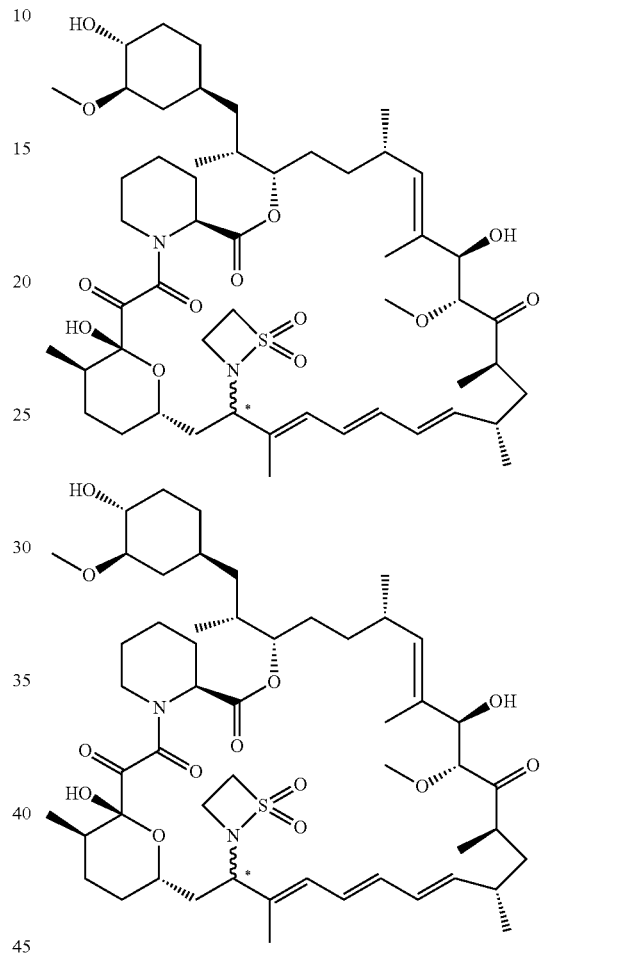

\* Absolute stereochemistry at C16 undetermined

To a solution of Intermediate 1 (150 mg, 0.167 mmol) and 1,2-thiazetidine 1,1-dioxide (891 mg, 0.833 mmol) in DCM (3 mL) was added zinc(II) chloride (1M solution in diethyl ether, 0.5 mL, 0.5 mmol) at 0° C. The reaction mixture was stirred at room temperature for two hours. The mixture was diluted with H$_2$O and was extracted with ethyl acetate. The organic extract was evaporated under reduced pressure. The crude product of the diastereomeric mixture was separated by flash chromatography (silica; MeCN/DCM 0:100 to 100:0).

Final purification of the first eluting diastereomer by preparative HPLC (method 2) yielded Intermediate 5 (18 mg, 10% yield) as a white solid.

Intermediate 5: ESIMS [M+NH$_4$]$^+$ 992.6, [M+FA−H]$^−$ 1019.6.

$^1$H NMR (400 MHz, Chloroform-d) δ 6.39 (dd, J=14.8, 9.8 Hz, 1H), 6.34 (dd, J=14.8, 10.3 Hz, 1H), 6.18-6.10 (m, 1H), 6.02 (d, J=10.3, 1.5 Hz, 1H), 5.66 (dd, J=15.1, 8.6 Hz, 1H), 5.38 (s, 1H), 5.32 (dd, J=6.4, 1.8 Hz, 1H), 5.23 (d, J=9.6 Hz, 1H), 4.87-4.76 (m, 1H), 4.12-4.06 (m, 1H), 3.99

(ddd, J=12.0, 8.2, 6.2 Hz, 1H), 3.92-3.86 (m, 1H), 3.84 (dd, J=10.7, 4.4 Hz, 1H), 3.81-3.74 (m, 1H), 3.63-3.59 (m, 2H), 3.59 (d, J=3.6 Hz, 1H), 3.46 (d, J=7.6 Hz, 1H), 3.43 (s, 3H), 3.40-3.37 (m, 1H), 3.32 (s, 3H), 3.04 (ddd, J=8.2, 5.8, 3.8 Hz, 1H), 3.00-2.94 (m, 1H), 2.94-2.89 (m, 1H), 2.88-2.84 (m, 1H), 2.64 (d, J=6.7 Hz, 1H), 2.47-2.38 (m, 1H), 2.36-2.27 (m, 2H), 2.21-2.12 (m, 1H), 2.03-1.97 (m, 1H), 1.95-1.77 (m, 7H), 1.76-1.67 (m, 5H), 1.65 (s, 3H), 1.60-1.50 (m, 6H), 1.47-1.39 (m, 2H), 1.38-1.27 (m, 4H), 1.25-1.10 (m, 3H), 1.08-1.04 (m, 1H), 1.03-1.01 (m, 3H), 1.00 (d, J=1.4 Hz, 3H), 0.99-0.97 (m, 3H), 0.97 (d, J=6.6 Hz, 3H), 0.93 (d, J=6.8 Hz, 3H), 0.75-0.66 (m, 1H).

Final purification of the second eluting diastereomer using SFC chromatography (method 2) yielded Intermediate 6 (16 mg, 9.2% yield) as a white solid.

Intermediate 6: ESIMS [M+NH$_4$]$^+$ 992.7, [M+FA−H]$^-$ 1019.6.

$^1$H NMR (400 MHz, Chloroform-d) δ 6.46 (dd, J=14.2, 10.9 Hz, 1H), 6.22 (dd, J=14.2, 10.6 Hz, 1H), 6.14 (dd, J=14.5, 10.6 Hz, 1H), 6.00 (d, J=10.9 Hz, 1H), 5.38 (dd, J=14.5, 9.6 Hz, 1H), 5.27-5.19 (m, 1H), 5.12-5.05 (m, 1H), 4.66-4.59 (m, 1H), 4.59-4.53 (m, 1H), 4.25 (d, J=1.8 Hz, 1H), 4.17-4.06 (m, 3H), 4.02 (ddd, J=11.8, 8.0, 3.5 Hz, 1H), 3.66 (d, J=7.0 Hz, 1H), 3.60-3.52 (m, 2H), 3.43-3.34 (m, 4H), 3.28 (s, 3H), 3.17-3.07 (m, 1H), 3.03-2.95 (m, 1H), 2.95-2.89 (m, 1H), 2.84-2.73 (m, 1H), 2.65-2.62 (m, 1H), 2.35-2.26 (m, 1H), 2.27-2.21 (m, 1H), 2.21-2.12 (m, 3H), 2.12-2.05 (m, 1H), 2.02-1.98 (m, 1H), 1.97-1.95 (m, 3H), 1.91-1.83 (m, 1H), 1.82-1.70 (m, 3H), 1.70-1.51 (m, 10H), 1.50-1.17 (m, 10H), 1.11-1.06 (m, 1H), 1.06-1.02 (m, 6H), 1.01-0.96 (m, 1H), 0.93 (d, J=6.8 Hz, 4H), 0.89 (d, J=6.6 Hz, 3H), 0.86 (d, J=6.8 Hz, 3H), 0.64 (q, J=11.9 Hz, 1H).

Intermediates 7 and 8

Intermediates 7 and 8

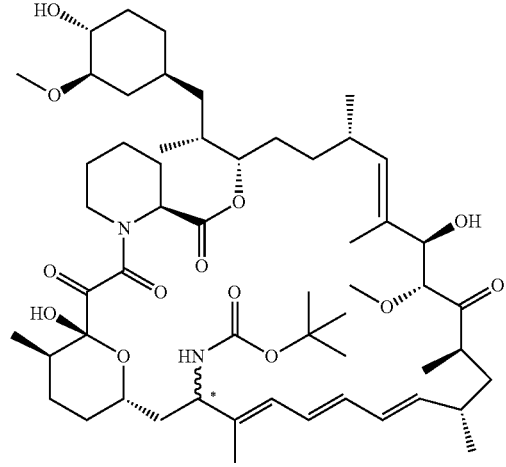

-continued

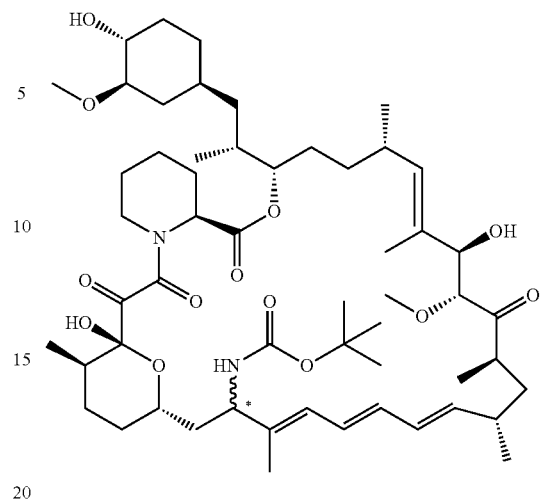

* Absolute stereochemistry at C16 undetermined

To a mixture of Intermediate 1 (500 mg, 0.555 mmol) and tert-butyl carbamate (976 mg, 8.33 mmol) in DCM (4 mL) was added 4-methylbenzenesulfonic acid hydrate (5.3 mg, 0.028 mmol). The reaction mixture was stirred at room temperature for 18 hours. The entire reaction mixture was directly separated by flash chromatography (silica; MeCN/DCM 0:100 to 25:75). The isolated first eluting diastereomer afforded Intermediate 7 (105 mg, 15.4% yield) as a yellow solid.

Intermediate 7: ESIMS [M+Na]$^+$ 1008.0, ESIMS [M−H]$^-$ 984.0.

The isolated second eluting diastereomer afforded Intermediate 8 (220 mg, 36.2% yield) as a yellow solid.

Intermediate 8: ESIMS [M+Na]$^+$ 1008.1, ESIMS [M−H]$^-$ 984.7.

HRMS: Calculated for C55H89N2O13—985.6365. Found—985.6379.

Intermediate 9 and Intermediate 10

Intermediate 9

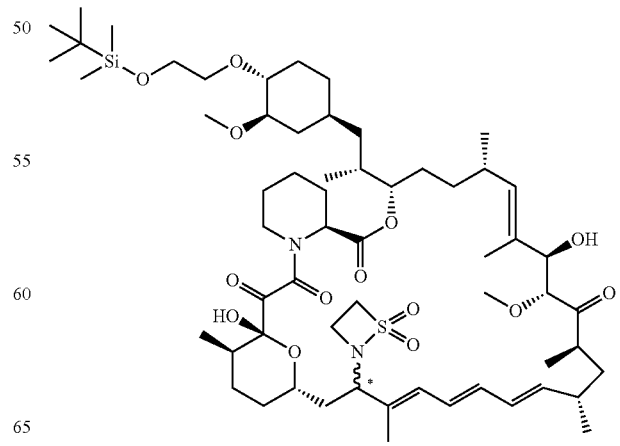

Intermediate 10

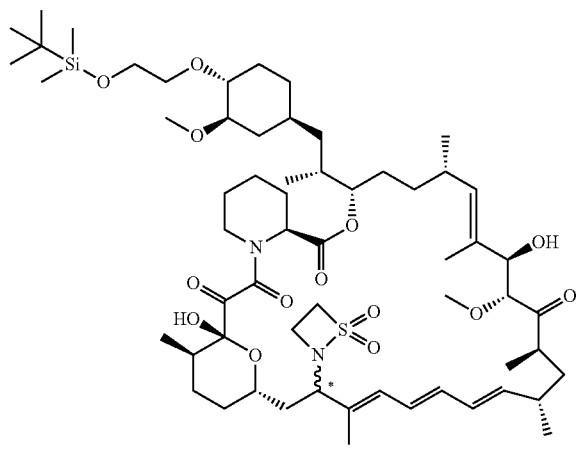

* Absolute C16 stereochemistry undetermined

To a solution of Intermediate 4 (120 mg, 0.113 mmol) and 1,2-thiazetidine 1,1-dioxide (121 mg, 1.13 mmol) in DCM (4 mL) was added zinc(II) chloride (1M solution in diethyl ether, 0.57 mL, 0.57 mmol). The reaction mixture was stirred at room temperature for three hours. The reaction was diluted with saturated aqueous $NaHCO_3$ and was extracted with ethylacetate. The organic extract was evaporated under reduced pressure to give a product mixture of both diastereomers. The diastereomeric mixture was separated by flash chromatography (silica; MeCN/DCM 0:100 to 40:60).

The first eluting diastereomer was purified using SFC chromatography (method 2) to afford Intermediate 9 (18.3 mg, 13.5% yield) as a white solid.

Intermediate 9: ESIMS $[M+NH_4]^+$ 1151.1, $[M+FA-H]^-$ 1178.2

$^1$H NMR (400 MHz, DMSO-$d_6$) δ: 6.57-6.37 (m, 2H), 6.32-6.12 (m, 2H), 6.04 (dd, J=22.7, 10.9 Hz, 1H), 5.60-5.48 (m, 1H), 5.06 (d, J=9.1 Hz, 1H), 4.98-4.91 (m, 1H), 4.90-4.83 (m, 1H), 4.68-4.59 (m, 1H), 4.17-3.99 (m, 3H), 3.92-3.86 (m, 1H), 3.69-3.61 (m, 3H), 3.59-3.49 (m, 3H), 3.49-3.41 (m, 1H), 3.34 (s, 3H), 3.28 (d, J=8.9 Hz, 1H), 3.17-3.09 (m, 4H), 3.09-3.03 (m, 1H), 3.01-2.93 (m, 2H), 2.91-2.80 (m, 1H), 2.29-2.12 (m, 2H), 2.12-2.00 (m, 1H), 1.99-1.88 (m, 3H), 1.82 (s, 3H), 1.78-1.62 (m, 6H), 1.58-1.54 (m, 1H), 1.53-1.32 (m, 10H), 1.34-1.20 (m, 3H), 1.18-1.09 (m, 3H), 1.06-0.94 (m, 7H), 0.92-0.83 (m, 13H), 0.80 (d, J=6.7 Hz, 3H), 0.77-0.68 (m, 4H), 0.68-0.59 (m, 1H), 0.03 (s, 6H).

The second eluting diastereomer was purified using SFC chromatography (method 2) to afford Intermediate 10 (7.3 mg, 5.5% yield) as a white solid.

Intermediate 10: ESIMS $[M+NH_4]^+$ 1151.3, $[M+FA-H]^-$ 1178.4

$^1$H NMR (400 MHz, DMSO-$d_6$) δ: 6.44 (dd, J=13.9, 11.0 Hz, 1H), 6.26-6.12 (m, 2H), 6.10-6.05 (m, 1H), 5.98 (s, 1H), 5.52 (dd, J=14.1, 9.4 Hz, 1H), 5.15-5.04 (m, 1H), 5.04-5.00 (m, 1H), 4.96 (d, J=9.7 Hz, 1H), 4.67-4.57 (m, 1H), 4.20-4.00 (m, 4H), 3.98-3.89 (m, 1H), 3.65 (t, J=5.2 Hz, 2H), 3.58-3.49 (m, 4H), 3.42-3.35 (m, 1H), 3.33 (s, 3H), 3.22-3.16 (m, 1H), 3.16-3.09 (m, 4H), 3.09-3.03 (m, 1H), 3.00-2.92 (m, 1H), 2.75-2.65 (m, 1H), 2.27-2.12 (m, 2H), 2.12-2.01 (m, 2H), 2.00-1.88 (m, 3H), 1.83 (s, 3H), 1.78-1.66 (m, 2H), 1.64-1.57 (m, 3H), 1.56-1.48 (m, 7H), 1.48-1.34 (m, 3H), 1.32-1.23 (m, 3H), 1.22-1.03 (m, 5H), 1.01-0.95 (m, 4H), 0.93-0.88 (m, 4H), 0.87-0.84 (m, 12H), 0.83-0.77 (m, 4H), 0.75 (d, J=6.7 Hz, 3H), 0.62 (q, J=11.9 Hz, 1H), 0.03 (s, 6H).

Example 1. Synthesis of Compound 1 and Compound 2

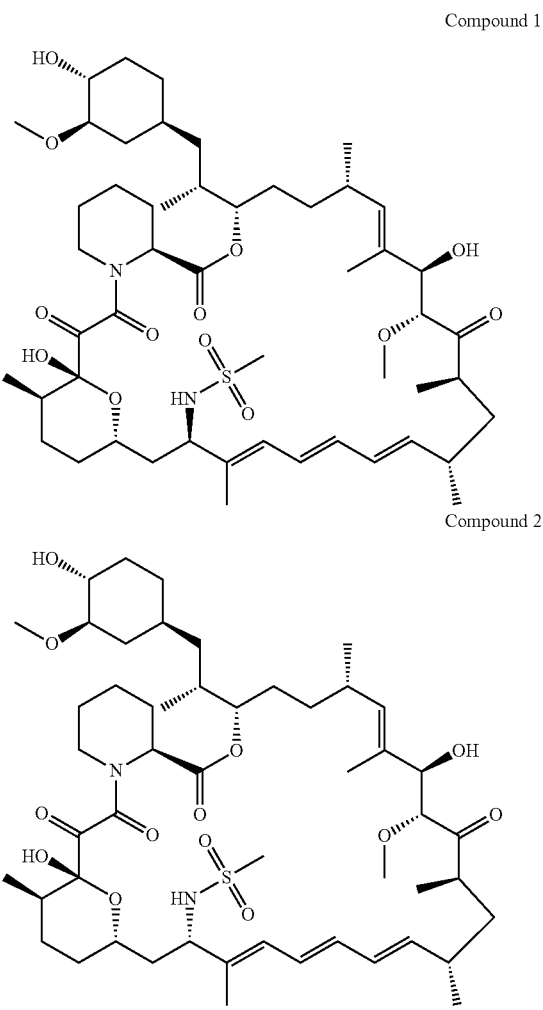

To a solution of Intermediate 1 (125 mg, 0.139 mmol) and methanesulfonamide (264 mg, 2.78 mmol) in DCM (8 mL) was added zinc(II) chloride (1M solution in diethyl ether, 0.69 mL, 0.69 mmol). The reaction mixture was stirred at room temperature for 30 minutes. The reaction was diluted with $H_2O$ and was extracted with ethyl acetate. The organic extract was evaporated under reduced pressure to give a product mixture of both diastereomers. The diastereomeric mixture was separated by reversed phase preparative HPLC chromatography (Method 1).

The first eluting diastereomer was isolated to afford Compound 1 (6.5 mg, 4.6% yield) as a white solid.

Compound 1: ESIMS $[M-H]^-$ 961.6

$^1$H NMR (400 MHz, DMSO-$d_6$) δ: 7.30 (d, J=7.9 Hz, 1H), 6.47 (s, 1H), 6.39 (dd, J=13.7, 11.2 Hz, 1H), 6.22-6.08 (m, 2H), 6.05 (d, J=11.0 Hz, 1H), 5.54 (dd, J=14.2, 8.8 Hz, 1H), 5.07-4.98 (m, 3H), 4.69-4.62 (m, 1H), 4.59 (d, J=4.6 Hz, 1H), 4.00-3.96 (m, 1H), 3.96-3.87 (m, 1H), 3.80-3.69 (m,

2H), 3.62 (d, J=14.5 Hz, 1H), 3.31 (d, J=1.7 Hz, 3H), 3.23-3.10 (m, 5H), 2.89 (s, 3H), 2.86-2.76 (m, 1H), 2.58-2.52 (m, 1H), 2.28-2.19 (m, 1H), 2.19-1.98 (m, 3H), 1.94-1.86 (m, 1H), 1.82-1.70 (m, 5H), 1.70-1.34 (m, 17H), 1.34-1.11 (m, 6H), 1.10-0.88 (m, 6H), 0.87-0.81 (m, 6H), 0.79 (d, J=6.7 Hz, 3H), 0.75 (d, J=6.6 Hz, 3H), 0.54 (q, J=11.8 Hz, 1H).

The second eluting diastereomer was purified using SFC chromatography (method 1) to afford Compound 2 (7.5 mg, 5.3% yield) as a white solid.

Compound 2: ESIMS [M−H]⁻ 961.7

$^1$H NMR (400 MHz, DMSO-d$_6$) δ: 7.49 (d, J=9.3 Hz, 1H), 6.60 (s, 1H), 6.44 (dd, J=14.3, 11.0 Hz, 1H), 6.31-6.11 (m, 2H), 5.98 (d, J=11.0 Hz, 1H), 5.51 (dd, J=14.5, 9.5 Hz, 1H), 5.05 (s, 1H), 4.99-4.92 (m, 1H), 4.87-4.77 (m, 1H), 4.66-4.53 (m, 2H), 3.95-3.85 (m, 2H), 3.77-3.68 (m, 1H), 3.68-3.57 (m, 1H), 3.49-3.39 (m, 1H), 3.39-3.28 (m, 3H), 3.26-3.14 (m, 2H), 3.12 (s, 3H), 2.91-2.78 (m, 2H), 2.71 (s, 3H), 2.22 (s, 1H), 2.17-1.83 (m, 6H), 1.81 (s, 3H), 1.79-1.57 (m, 5H), 1.56-1.08 (m, 17H), 1.06-0.89 (m, 8H), 0.86 (d, J=6.6 Hz, 4H), 0.79 (d, J=6.7 Hz, 3H), 0.74 (d, J=6.7 Hz, 3H), 0.65-0.54 (m, 2H).

The absolute configuration of the C16 substituent in Compound 2 was determined by X-ray crystallographic co-crystallization with FKBP12. [See Stuart L. Schrieber and Jon Clardy, et al., Atomic Structure of the Rapamycin Humano Immunophilin FKBP-12 Complex, *J. Am. Chem. Soc.*, 1991, 113, 7433-7434.] The crystal structure is depicted in FIG. 1.

Pure FKBP12(1-108) protein was concentrated to 9 mg/mL in 50 mM Tris pH 8.0, 150 mM NaCl, 1 mM EDTA, 1 mM TCEP. The complex for co-crystallization was prepared by mixing the protein with 3 mM of compound (from a 50 mM stock prepared in 90% dDMSO, 10% D20). The complex was incubated for two hours at 4° C. then was centrifuged at 10000 rpm for 2 minutes to remove any potential pellet before crystallization. Co-crystals were obtained at 20° C. and by sitting drop vapor diffusion using microseed matrix screening [Allan D'Arcy et al., An automated microseed matrix-screening method for protein crystallization, *Acta Cryst.*, (2007) D63, 550-554.] The drops were made up of 200 nL of protein solution, 160 nL of well solution and 40 nL seed-stock. Crystals appeared within a few days in the A1 condition of the commercially available "Ammonium sulfate" screen from Qiagen. The reservoir solution consisted of 2.2M Ammonium sulfate. Crystals were cryoprotected in reservoir solution supplemented with 20% Ethylene Glycol and flash-frozen into liquid nitrogen. Data was collected at the Swiss Light Source Facility (SLS, Villigen, Switzerland) on beamline X10SA.

The data were processed with XDS (Kabsch, W. (2010), XDS. Acta Cryst. D, 66: 125-132). The structures were determined by molecular replacement (Collaborative Computational Project, Number 4 (1994). Acta Cryst. D50, 760-763) using previous FKBP12 X-ray structures as search model. Programs REFMAC (Murshudov G N, Skubák P, Lebedev A A, et al., REFMAC5 for the refinement of macromolecular crystal structures. *Acta Crystallographica Section D: Biological Crystallography.* 2011; 67(Pt 4):355-367) and COOT (Emsley P, Lohkamp B, Scott W G, Cowtan K. Features and development of *Coot, Acta Crystallographica Section D: Biological Crystallography.* 2010; 66(Pt 4):486-501) were used for refinement and model (re)building.

Based on the X-ray co-crystal structure, the C16 substituent in Compound 2 is in the (S)-configuration. The crystal structure is depicted in FIG. 1.

Example 2. Compound 3 and Compound 4

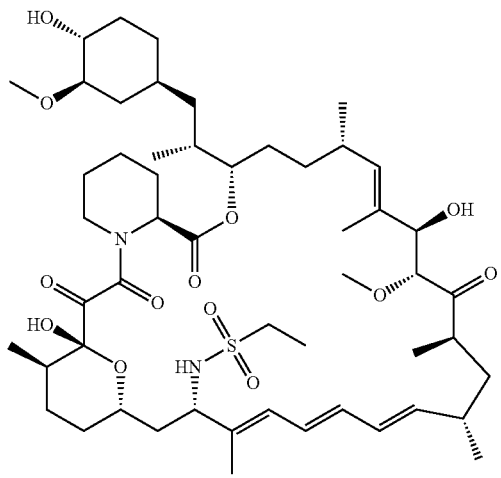

Compound 3

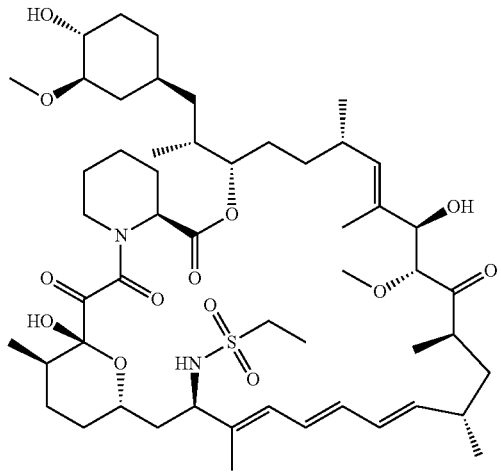

Compound 4

To a solution of Intermediate 1 (120 mg, 0.133 mmol) and ethanesulfonamide (218 mg, 2.00 mmol) in DCM (7 mL) was added zinc(II) chloride (1M solution in diethyl ether, 0.67 mL, 0.67 mmol). The reaction mixture was stirred at room temperature for 14 minutes. The reaction was diluted with H$_2$O and was extracted with ethylacetate. The organic extract was evaporated under reduced pressure to give a product mixture of both diastereomers. The diastereomeric mixture was separated by flash chromatography (silica; MeCN/DCM 0:100 to 50:50).

The first eluting diastereomer was purified using SFC chromatography (method 1) to afford Compound 3 (13.4 mg, 10.1% yield) as a white solid.

Compound 3: ESIMS [M+NH$_4$]⁺ 994.7, [M+FA−H]⁻ 1021.7

$^1$H NMR (400 MHz, DMSO-d$_6$) δ: 7.52 (d, J=9.3 Hz, 1H), 6.59 (s, 1H), 6.43 (dd, J=14.2, 11.0 Hz, 1H), 6.24 (dd, J=14.2, 10.6 Hz, 1H), 6.17 (dd, J=14.2, 10.7 Hz, 1H), 5.96 (d, J=10.9, 1.6 Hz, 1H), 5.50 (dd, J=14.4, 9.6 Hz, 1H), 5.04 (d, J=4.7 Hz, 1H), 4.96-4.89 (m, 1H), 4.87-4.78 (m, 1H), 4.69-4.54 (m, 2H), 4.00-3.91 (m, 1H), 3.88 (dd, J=9.3, 4.7 Hz, 1H), 3.76-3.67 (m, 1H), 3.67-3.58 (m, 1H), 3.50-3.40 (m, 1H), 3.31 (s, 3H), 3.25-3.15 (m, 2H), 3.12 (s, 3H), 2.92-2.79 (m, 3H), 2.77-2.65 (m, 1H), 2.29-2.17 (m, 1H), 2.17-2.10 (m, 1H), 2.10-1.98 (m, 2H), 1.97-1.86 (m, 3H), 1.82 (s, 3H), 1.80-1.76 (m, 1H), 1.74-1.68 (m, 2H), 1.67-1.60 (m, 2H), 1.55-1.49 (m, 3H), 1.48 (s, 3H), 1.46-1.33 (m, 4H), 1.32-1.24 (m, 1H), 1.22-1.11 (m, 6H), 1.09 (t, J=7.3 Hz, 3H), 1.07-1.01 (m, 1H), 1.01-0.94 (m, 7H), 0.89-0.82 (m, 4H), 0.79 (d, J=6.7 Hz, 3H), 0.74 (d, J=6.7 Hz, 3H), 0.70-0.63 (m, 1H), 0.63-0.54 (m, 1H).

The second eluting diastereomer was purified using SFC chromatography (method 1) to afford Compound 4 (28.6 mg, 21.5% yield) as a white solid.

Compound 4: ESIMS [M+NH$_4$]$^+$ 994.8, [M−H]$^-$ 976.0

$^1$H NMR (400 MHz, DMSO-d$_6$) δ: 7.30 (d, J=7.9 Hz, 1H), 6.42 (s, 1H), 6.41-6.34 (m, 1H), 6.19-6.10 (m, 2H), 6.10-6.04 (m, 1H), 5.54 (dd, J=14.2, 8.9 Hz, 1H), 5.06-5.00 (m, 3H), 4.66 (ddd, J=9.4, 6.0, 2.5 Hz, 1H), 4.59 (d, J=4.5 Hz, 1H), 4.03-3.96 (m, 1H), 3.96-3.85 (m, 1H), 3.75 (d, J=5.3 Hz, 1H), 3.74-3.68 (m, 1H), 3.62 (dd, J=9.9, 6.3 Hz, 1H), 3.31 (s, 3H), 3.23-3.10 (m, 5H), 3.03-2.90 (m, 2H), 2.82 (ddd, J=11.0, 8.7, 4.3 Hz, 1H), 2.52-2.48 (m, 1H), 2.29-2.19 (m, 1H), 2.19-2.12 (m, 1H), 2.12-2.07 (m, 1H), 2.06-1.98 (m, 1H), 1.97-1.86 (m, 1H), 1.80-1.70 (m, 5H), 1.69-1.64 (m, 1H), 1.64-1.56 (m, 4H), 1.56-1.50 (m, 6H), 1.50-1.43 (m, 2H), 1.43-1.33 (m, 3H), 1.30-1.23 (m, 2H), 1.21-1.12 (m, 7H), 1.11-1.01 (m, 1H), 0.98 (d, J=6.4 Hz, 3H), 0.96-0.87 (m, 2H), 0.87-0.81 (m, 7H), 0.79 (d, J=6.7 Hz, 3H), 0.75 (d, J=6.6 Hz, 3H), 0.54 (q, J=11.8 Hz, 1H).

Example 3. Synthesis of Compound 5 and Compound 6

Compound 5

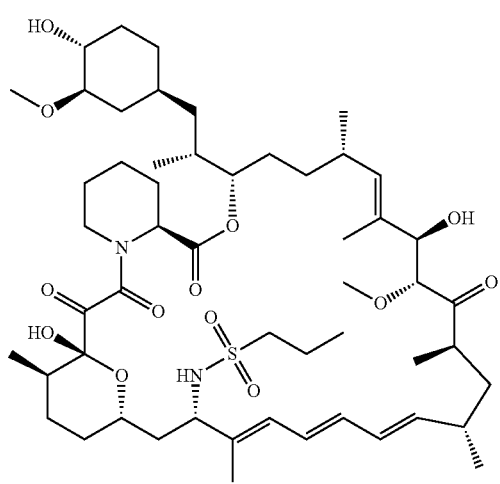

Compound 6

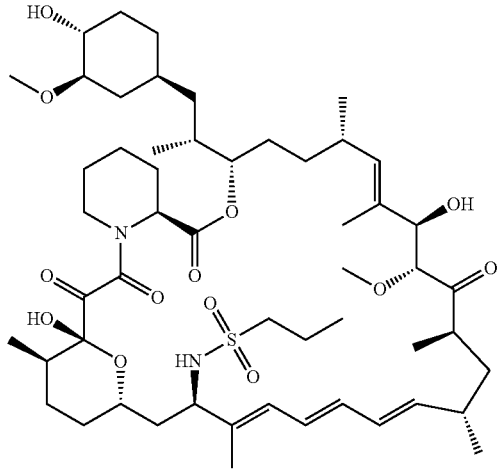

To a solution of Intermediate 1 (120 mg, 0.133 mmol) and propane-1-sulfonamide (328 mg, 2.67 mmol) in DCM (7 mL) was added zinc(II) chloride (1M solution in diethyl ether, 0.67 mL, 0.67 mmol). The reaction mixture was stirred at room temperature for 10 minutes. The reaction was diluted with H$_2$O and was extracted with ethylacetate. The organic extract was evaporated under reduced pressure to give a product mixture of both diastereomers. The diastereomeric mixture was separated by flash chromatography (silica; MeCN/DCM 100:0 to 50:50.

The first eluting diastereomer was purified using flash chromatography (silica; MeCN/DCM 0:100 to 40:60) followed by reversed phase preparative HPLC (method 2) to afford Compound 5 (2.5 mg, 1.8% yield) as a white solid.

Compound 5: ESIMS [M+NH$_4$]$^+$ 1008.8, [M+FA−H]$^-$ 1035.8

$^1$H NMR (400 MHz, DMSO-d$_6$) δ: 7.53 (d, J=9.4 Hz, 1H), 6.59 (s, 1H), 6.43 (dd, J=14.2, 11.0 Hz, 1H), 6.25 (dd, J=14.2, 10.5 Hz, 1H), 6.18 (dd, J=14.4, 10.6 Hz, 1H), 6.01-5.92 (m, 1H), 5.50 (dd, J=14.5, 9.6 Hz, 1H), 5.05 (d, J=4.7 Hz, 1H), 4.97-4.91 (m, 1H), 4.86-4.78 (m, 1H), 4.66-4.53 (m, 2H), 3.99-3.90 (m, 1H), 3.87 (dd, J=9.3, 4.6 Hz, 1H), 3.75-3.67 (m, 1H), 3.67-3.59 (m, 1H), 3.49-3.40 (m, 1H), 3.31 (s, 3H), 3.22 (d, J=9.2 Hz, 1H), 3.20-3.14 (m, 1H), 3.12 (s, 3H), 2.89-2.78 (m, 3H), 2.73-2.63 (m, 1H), 2.28-2.17 (m, 1H), 2.17-2.09 (m, 1H), 2.09-2.01 (m, 2H), 1.96-1.86 (m, 3H), 1.81 (s, 3H), 1.78-1.69 (m, 3H), 1.69-1.60 (m, 2H), 1.60-1.53 (m, 2H), 1.53-1.49 (m, 3H), 1.48 (s, 3H), 1.45-1.35 (m, 3H), 1.35-1.25 (m, 2H), 1.23-1.09 (m, 6H), 1.07-1.01 (m, 2H), 0.98 (d, J=3.3 Hz, 3H), 0.97 (d, J=3.4 Hz, 3H), 0.89-0.84 (m, 7H), 0.79 (d, J=6.7 Hz, 3H), 0.74 (d, J=6.7 Hz, 3H), 0.70-0.65 (m, 1H), 0.64-0.54 (m, 1H).

The second eluting diastereomer was purified using reversed phase flash chromatography (C18; MeCN/water 10:90 to 100:0) to afford Compound 6 (3 mg, 2.2% yield) as a white solid.

Compound 6: ESIMS [M+NH$_4$]$^+$ 1008.8, [M+FA−H]$^-$ 1035.8

$^1$H NMR (400 MHz, DMSO-d$_6$) δ: 7.53-7.06 (m, 1H), 6.51-6.30 (m, 2H), 6.19-6.09 (m, 2H), 6.06 (d, J=11.4 Hz, 1H), 5.53 (dd, J=14.3, 8.7 Hz, 1H), 5.15-4.95 (m, 3H), 4.66 (td, J=7.5, 6.0, 2.4 Hz, 1H), 4.62-4.52 (m, 1H), 4.05-3.95 (m, 1H), 3.95-3.84 (m, 1H), 3.77 (d, J=5.1 Hz, 1H), 3.75-3.68 (m, 1H), 3.68-3.58 (m, 1H), 3.31 (s, 3H), 3.24-3.09 (m, 5H), 3.03-2.95 (m, 1H), 2.95-2.87 (m, 1H), 2.84-2.78 (m, 1H), 2.57-2.43 (m, 1H), 2.35-2.21 (m, 1H), 2.20-2.11 (m, 1H), 2.11-1.96 (m, 2H), 1.96-1.85 (m, 1H), 1.82-1.70 (m, 5H), 1.70-1.56 (m, 8H), 1.56-1.48 (m, 6H), 1.48-1.32 (m, 4H), 1.32-1.09 (m, 6H), 1.08-1.00 (m, 1H), 1.00-0.92 (m, 6H), 0.92-0.86 (m, 3H), 0.86-0.80 (m, 6H), 0.78 (d, J=6.7 Hz, 3H), 0.75 (d, J=6.6 Hz, 3H), 0.53 (q, J=11.8 Hz, 1H).

Example 4. Synthesis of Compound 7 and Compound 8

Compound 7

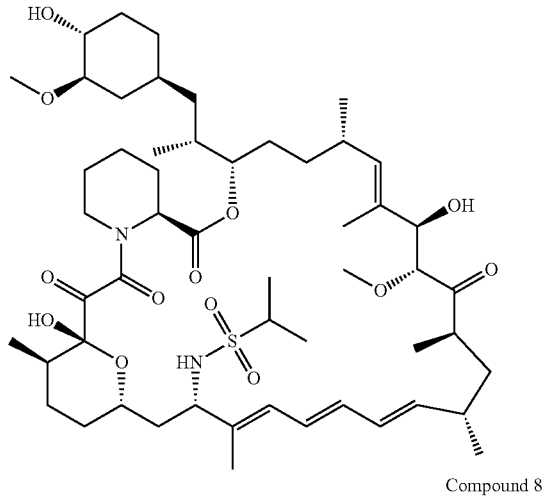

Compound 8

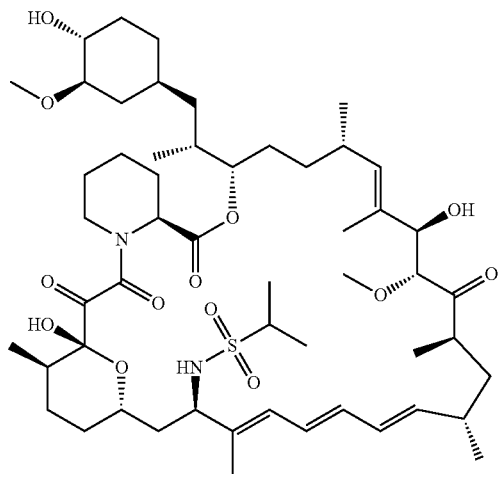

To a solution of Intermediate 1 (120 mg, 0.133 mmol) and propane-2-sulfonamide (164 mg, 1.33 mmol) in DCM (6 mL) was added zinc(II) chloride (1M solution in diethyl ether, 0.67 mL, 0.67 mmol). The reaction mixture was stirred at room temperature for 18 hours. The reaction was diluted with $H_2O$ and was extracted with ethylacetate. The organic extract was evaporated under reduced pressure to give a product mixture of both diastereomers. The diastereomeric mixture was separated by flash chromatography (silica; MeCN/DCM 0:100 to 40:60).

The first eluting diastereomer was purified using SFC chromatography (method 1) to afford Compound 7 (9.1 mg, 6.7% yield) as a white solid.

Compound 7: ESIMS $[M+NH_4]^+$ 1008.8, $[M+FA-H]^+$ 1035.9

$^1$H NMR (400 MHz, DMSO-$d_6$) δ: 7.47 (d, J=9.3 Hz, 1H), 6.59 (s, 1H), 6.42 (dd, J=14.0, 11.0 Hz, 1H), 6.29-6.19 (m, 1H), 6.16 (dd, J=13.7, 10.1 Hz, 1H), 5.97-5.89 (m, 1H), 5.49 (dd, J=14.2, 9.6 Hz, 1H), 5.04 (d, J=4.7 Hz, 1H), 4.98-4.88 (m, 1H), 4.87-4.77 (m, 1H), 4.66-4.55 (m, 2H), 4.03-3.90 (m, 1H), 3.87 (dd, J=9.2, 4.6 Hz, 1H), 3.75-3.68 (m, 1H), 3.68-3.58 (m, 1H), 3.50-3.39 (m, 1H), 3.32 (s, 3H), 3.25-3.15 (m, 2H), 3.12 (s, 3H), 2.94-2.76 (m, 3H), 2.29-2.17 (m, 1H), 2.17-2.00 (m, 3H), 2.00-1.87 (m, 3H), 1.82 (s, 3H), 1.81-1.70 (m, 2H), 1.70-1.59 (m, 3H), 1.59-1.45 (m, 6H), 1.45-1.34 (m, 3H), 1.34-1.22 (m, 2H), 1.22-1.14 (m, 7H), 1.15-1.12 (m, 2H), 1.10 (d, J=6.7 Hz, 3H), 1.07-0.99 (m, 2H), 1.00-0.93 (m, 6H), 0.89-0.82 (m, 4H), 0.79 (d, J=6.7 Hz, 3H), 0.74 (d, J=6.7 Hz, 3H), 0.72-0.64 (m, 1H), 0.64-0.52 (m, 1H).

The second eluting diastereomer was purified using SFC chromatography (method 1) to afford Compound 8 (19.8 mg, 14.5% yield) as a white solid.

Compound 8: ESIMS $[M+NH_4]^+$ 1008.7, $[M-H]^-$ 989.7

$^1$H NMR (400 MHz, DMSO-$d_6$) δ: 7.26 (d, J=8.1 Hz, 1H), 6.43-6.37 (m, 1H), 6.36 (s, 1H), 6.18-6.04 (m, 3H), 5.54 (dd, J=14.0, 8.9 Hz, 1H), 5.08-4.98 (m, 3H), 4.71-4.62 (m, 1H), 4.59 (d, J=4.4 Hz, 1H), 4.08-3.97 (m, 1H), 3.96-3.89 (m, 1H), 3.77 (d, J=5.0 Hz, 1H), 3.74-3.67 (m, 1H), 3.66-3.58 (m, 1H), 3.31 (s, 3H), 3.21-3.09 (m, 6H), 2.86-2.77 (m, 1H), 2.54-2.45 (m, 1H), 2.28-2.20 (m, 1H), 2.19-2.13 (m, 1H), 2.12-2.06 (m, 1H), 2.06-1.99 (m, 1H), 1.95-1.86 (m, 1H), 1.81-1.68 (m, 5H), 1.68-1.56 (m, 4H), 1.56-1.49 (m, 6H), 1.49-1.32 (m, 6H), 1.32-1.25 (m, 1H), 1.25-1.10 (m, 11H), 1.09-1.01 (m, 1H), 0.98 (d, J=6.6 Hz, 3H), 0.94-0.88 (m, 2H), 0.88-0.81 (m, 7H), 0.79 (d, J=6.7 Hz, 3H), 0.75 (d, J=6.7 Hz, 3H), 0.53 (q, J=11.8 Hz, 1H).

Example 5. Synthesis of Compound 9 and Compound 10

Compound 9

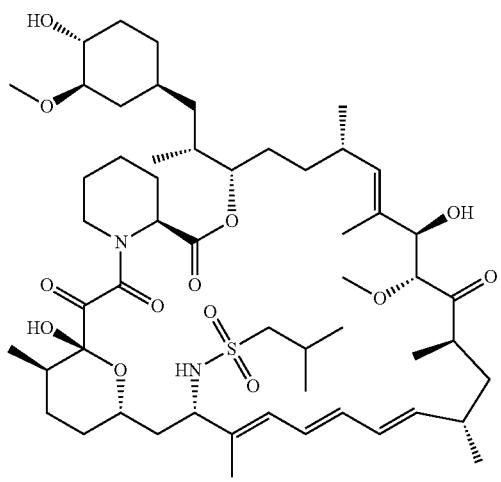

-continued

Compound 10

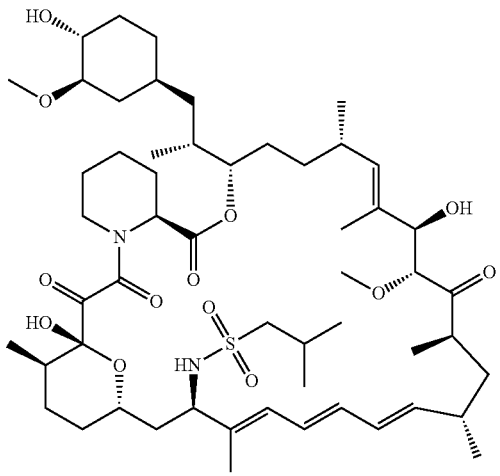

To a solution of Intermediate 1 (120 mg, 0.133 mmol) and 2-methylpropane-1-sulfonamide (274 mg, 2.00 mmol) in DCM (7 mL) was added zinc(II) chloride (1M solution in diethyl ether, 0.67 mL, 0.67 mmol). The reaction mixture was stirred at room temperature for 1 hour. The mixture was diluted with $H_2O$ and was extracted with ethylacetate. The organic extract was evaporated under reduced pressure to give a product mixture of both diastereomers. The diastereomeric mixture was separated by flash chromatography (silica; MeCN/DCM 0:100 to 50:50).

The first eluting diastereomer was purified using SFC chromatography (method 1) to afford Compound 9 (13.9 mg, 10.2% yield) as a white solid.

Compound 9: ESIMS $[M+NH_4]^+$ 1022.8, $[M-H]^-$ 1003.8

$^1$H NMR (400 MHz, DMSO-$d_6$) δ: 7.54 (d, J=9.3 Hz, 1H), 6.58 (s, 1H), 6.43 (dd, J=14.2, 11.0 Hz, 1H), 6.25 (dd, J=14.3, 10.6 Hz, 1H), 6.18 (dd, J=14.4, 10.5 Hz, 1H), 6.01-5.91 (m, 1H), 5.50 (dd, J=14.4, 9.6 Hz, 1H), 5.05 (d, J=4.5 Hz, 1H), 4.97-4.90 (m, 1H), 4.86-4.78 (m, 1H), 4.67-4.54 (m, 2H), 3.98-3.89 (m, 1H), 3.89-3.79 (m, 1H), 3.76-3.68 (m, 1H), 3.67-3.58 (m, 1H), 3.50-3.41 (m, 1H), 3.31 (s, 3H), 3.25-3.15 (m, 2H), 3.12 (s, 3H), 2.89-2.77 (m, 2H), 2.74-2.61 (m, 2H), 2.28-2.17 (m, 1H), 2.17-2.09 (m, 1H), 2.09-2.00 (m, 2H), 2.00-1.95 (m, 1H), 1.95-1.86 (m, 3H), 1.81 (s, 3H), 1.78-1.59 (m, 5H), 1.58-1.50 (m, 3H), 1.48 (s, 3H), 1.45-1.35 (m, 3H), 1.35-1.24 (m, 2H), 1.23-1.08 (m, 6H), 1.05-1.00 (m, 2H), 1.00-0.96 (m, 9H), 0.91-0.87 (m, 4H), 0.85 (d, J=6.4 Hz, 3H), 0.79 (d, J=6.7 Hz, 3H), 0.76 (d, J=6.7 Hz, 3H), 0.70-0.63 (m, 1H), 0.63-0.54 (m, 1H).

The second eluting diastereomer was purified using SFC chromatography (method 1) to afford Compound 10 (24.6 mg, 18.0% yield) as a white solid.

Compound 10: ESIMS $[M+NH_4]^+$ 1022.9, $[M-H]^-$ 1004.0

$^1$H NMR (400 MHz, DMSO-$d_6$) δ: 7.32 (d, J=8.2 Hz, 1H), 6.47-6.33 (m, 2H), 6.20-6.10 (m, 2H), 6.09-6.03 (m, 1H), 5.53 (dd, J=14.2, 8.8 Hz, 1H), 5.10-4.97 (m, 3H), 4.73-4.62 (m, 1H), 4.59 (d, J=4.5 Hz, 1H), 4.04-3.96 (m, 1H), 3.95-3.87 (m, 1H), 3.78 (d, J=4.8 Hz, 1H), 3.76-3.69 (m, 1H), 3.68-3.58 (m, 1H), 3.31 (s, 3H), 3.22-3.09 (m, 5H), 2.94-2.84 (m, 2H), 2.83-2.76 (m, 1H), 2.56-2.42 (m, 1H), 2.29-2.20 (m, 1H), 2.20-2.13 (m, 1H), 2.11-2.00 (m, 3H), 1.95-1.87 (m, 1H), 1.81-1.70 (m, 5H), 1.68-1.56 (m, 5H), 1.56-1.50 (m, 5H), 1.50-1.43 (m, 3H), 1.43-1.33 (m, 3H), 1.31-1.11 (m, 6H), 1.09-0.95 (m, 10H), 0.95-0.87 (m, 2H), 0.87-0.81 (m, 7H), 0.79 (d, J=6.7 Hz, 3H), 0.75 (d, J=6.6 Hz, 3H), 0.53 (q, J=11.8 Hz, 1H).

Example 6. Synthesis of Compound 11 and Compound 12

Compound 11

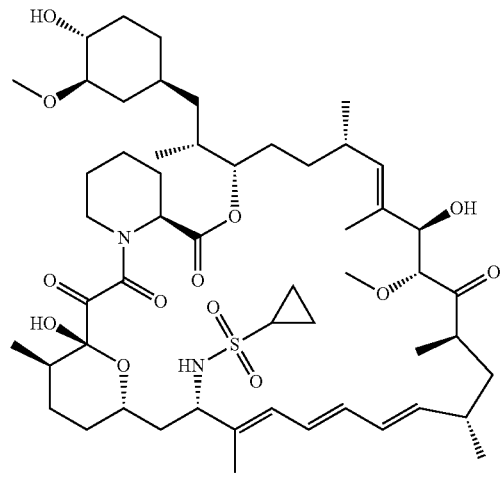

Compound 12

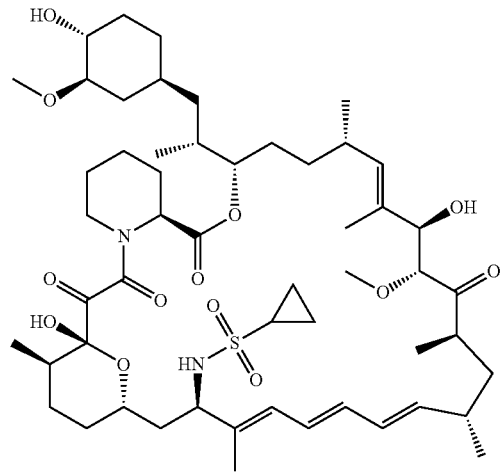

To a solution of Intermediate 1 (120 mg, 0.133 mmol) and cyclopropanesulfonamide (323 mg, 2.67 mmol) in DCM (7 mL) was added zinc(II) chloride (1M solution in diethyl ether, 0.67 mL, 0.67 mmol). The reaction mixture was stirred at room temperature for 10 minutes. The reaction mixture was diluted with $H_2O$ and was extracted with ethylacetate. The organic extract was evaporated under reduced pressure to give a product mixture of both diastereomers. The diastereomeric mixture was separated by flash chromatography (silica; MeCN/DCM 0:100 to 100:0).

The first eluting diastereomer was purified using SFC chromatography (method 1) to afford Compound 11 (4.4 mg, 3.2% yield) as a white solid.

Compound 11: ESIMS $[M+NH_4]^+$ 1006.7, $[M+FA-H]^-$ 1033.7

$^1$H NMR (400 MHz, DMSO-$d_6$) δ: 7.51 (d, J=8.5 Hz, 1H), 6.59 (s, 1H), 6.43 (dd, J=14.1, 11.0 Hz, 1H), 6.22 (dd, J=14.2, 10.5 Hz, 1H), 6.17 (dd, J=14.4, 10.8 Hz, 1H), 6.00-5.91 (m, 1H), 5.50 (dd, J=14.3, 9.6 Hz, 1H), 5.05 (d, J=4.5 Hz, 1H), 4.99-4.90 (m, 1H), 4.87-4.79 (m, 1H), 4.69-4.54 (m, 2H), 4.00-3.90 (m, 1H), 3.90-3.80 (m, 1H), 3.78-3.68 (m, 1H), 3.68-3.56 (m, 1H), 3.50-3.40 (m, 1H), 3.31 (s, 3H), 3.23 (d, J=9.2 Hz, 1H), 3.19-3.15 (m, 1H), 3.12 (s, 3H), 2.91-2.78 (m, 2H), 2.29-2.17 (m, 2H), 2.17-2.09 (m, 1H), 2.06-1.98 (m, 2H), 1.98-1.86 (m, 3H), 1.83 (s, 3H), 1.79-1.74 (m, 1H), 1.73-1.67 (m, 2H), 1.67-1.58 (m, 2H), 1.58-1.49 (m, 3H), 1.48 (s, 3H), 1.46-1.27 (m, 5H), 1.24-1.09 (m, 6H), 1.09-1.00 (m, 2H), 1.00-0.94 (m, 6H), 0.89-0.85 (m, 4H), 0.85-0.81 (m, 4H), 0.79 (d, J=6.8 Hz, 3H), 0.74 (d, J=6.7 Hz, 3H), 0.73-0.66 (m, 1H), 0.60 (q, J=11.8 Hz, 1H).

The second eluting diastereomer was purified using SFC chromatography (method 1) to afford Compound 12 (16.7 mg, 12.4% yield) as a white solid.

Compound 12: ESIMS [M+NH$_4$]$^+$ 1006.4, [M−H]$^−$ 987.5

$^1$H NMR (400 MHz, DMSO-d$_6$) δ: 7.28 (d, J=7.6 Hz, 1H), 6.47-6.37 (m, 1H), 6.36 (s, 1H), 6.20-6.09 (m, 2H), 6.05 (d, J=11.1 Hz, 1H), 5.54 (dd, J=14.3, 8.7 Hz, 1H), 5.10-4.96 (m, 3H), 4.70-4.63 (m, 1H), 4.59 (d, J=4.4 Hz, 1H), 4.05-3.94 (m, 2H), 3.84-3.76 (m, 1H), 3.71 (d, J=5.4 Hz, 1H), 3.66-3.57 (m, 1H), 3.31 (s, 3H), 3.23-3.17 (m, 1H), 3.17-3.10 (m, 4H), 2.82 (ddd, J=11.0, 8.7, 4.3 Hz, 1H), 2.63-2.53 (m, 2H), 2.31-2.19 (m, 1H), 2.19-2.09 (m, 2H), 2.06-1.99 (m, 1H), 1.96-1.87 (m, 1H), 1.80-1.72 (m, 5H), 1.69-1.57 (m, 5H), 1.57-1.50 (m, 7H), 1.50-1.44 (m, 2H), 1.44-1.33 (m, 2H), 1.32-1.12 (m, 6H), 1.12-1.01 (m, 1H), 0.98 (d, J=6.4 Hz, 3H), 0.94-0.88 (m, 6H), 0.88-0.82 (m, 7H), 0.79 (d, J=6.7 Hz, 3H), 0.75 (d, J=6.7 Hz, 3H), 0.54 (q, J=11.8 Hz, 1H).

Example 7. Synthesis of Compound 13 and Compound 14

Compound 13

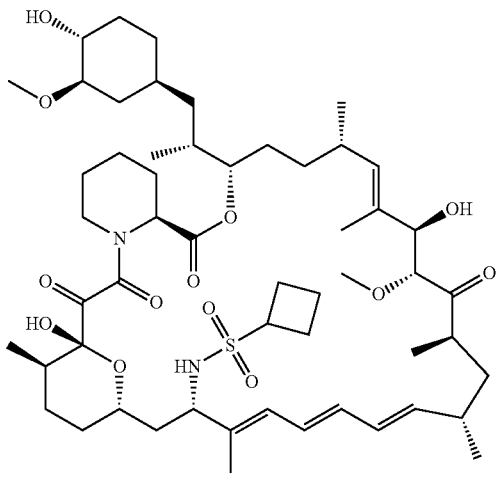

Compound 14

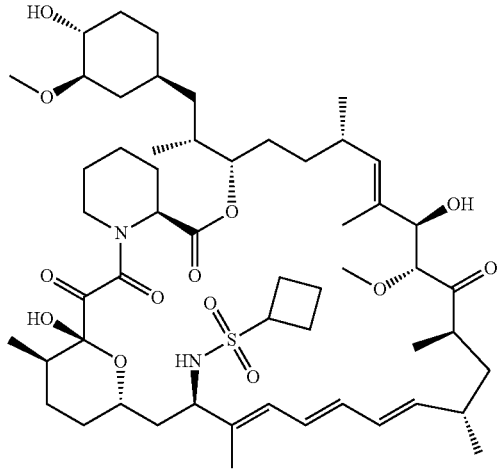

To a solution of Intermediate 1 (120 mg, 0.133 mmol) and cyclobutanesulfonamide (270 mg, 2.00 mmol) in DCM (7 mL) was added zinc(II) chloride (1M solution in diethyl ether, 0.67 mL, 0.67 mmol). The reaction mixture was stirred at room temperature for eleven minutes. The reaction was diluted with H$_2$O and was extracted with ethylacetate. The organic extract was evaporated under reduced pressure to give a product mixture of both diastereomers. The diastereomeric mixture was separated by flash chromatography (silica; MeCN/DCM 0:100 to 80:20).

The first eluting diastereomer was purified using SFC chromatography (method 1) to afford Compound 13 (12.3 mg, 9.19% yield) as a white solid.

Compound 13: ESIMS [M+NH$_4$]$^+$ 1020.8, [M+FA−H]$^−$ 1047.9

$^1$H NMR (400 MHz, DMSO-d$_6$) δ: 7.46 (d, J=9.3 Hz, 1H), 6.59 (s, 1H), 6.43 (dd, J=13.9, 11.0 Hz, 1H), 6.29-6.21 (m, 1H), 6.21-6.13 (m, 1H), 5.92 (dd, J=11.0, 1.5 Hz, 1H), 5.50 (dd, J=14.2, 9.6 Hz, 1H), 5.05 (d, J=4.7 Hz, 1H), 4.97-4.90 (m, 1H), 4.86-4.78 (m, 1H), 4.65-4.56 (m, 2H), 3.97-3.90 (m, 1H), 3.89-3.84 (m, 1H), 3.71-3.65 (m, 1H), 3.65-3.58 (m, 1H), 3.55-3.49 (m, 1H), 3.47-3.40 (m, 1H), 3.31 (s, 3H), 3.22 (d, J=9.2 Hz, 1H), 3.20-3.14 (m, 1H), 3.12 (s, 3H), 2.91-2.79 (m, 2H), 2.26-2.17 (m, 3H), 2.17-2.09 (m, 2H), 2.09-1.99 (m, 3H), 1.96-1.87 (m, 3H), 1.86-1.80 (m, 2H), 1.80-1.71 (m, 5H), 1.69-1.59 (m, 3H), 1.57-1.50 (m, 3H), 1.48 (s, 3H), 1.45-1.35 (m, 3H), 1.35-1.25 (m, 2H), 1.22-1.08 (m, 6H), 1.07-1.00 (m, 1H), 1.00-0.93 (m, 7H), 0.89-0.82 (m, 4H), 0.78 (d, J=6.7 Hz, 3H), 0.74 (d, J=6.7 Hz, 3H), 0.71-0.63 (m, 1H), 0.63-0.54 (m, 1H).

The second eluting diastereomer was purified using SFC chromatography (method 1) to afford Compound 14 (26.6 mg, 19.5% yield) as a white solid.

Compound 14: ESIMS [M+NH$_4$]$^+$ 1020.9, [M−H]$^−$ 1002.0

$^1$H NMR (400 MHz, DMSO-d$_6$) δ: 7.27 (d, J=8.2 Hz, 1H), 6.47 (s, 1H), 6.44-6.34 (m, 1H), 6.17-6.09 (m, 2H), 6.04 (dd, J=11.1, 1.6 Hz, 1H), 5.58-5.47 (m, 1H), 5.07-4.98 (m, 3H), 4.70-4.62 (m, 1H), 4.59 (s, 1H), 4.03-3.96 (m, 1H), 3.93-3.86 (m, 1H), 3.85-3.81 (m, 1H), 3.77 (d, J=4.9 Hz, 1H), 3.68-3.63 (m, 2H), 3.31 (s, 3H), 3.20-3.09 (m, 5H), 2.81 (ddd, J=11.2, 8.6, 4.3 Hz, 1H), 2.54-2.45 (m, 1H), 2.27-2.14 (m, 6H), 2.10-2.00 (m, 2H), 1.95-1.82 (m, 3H), 1.77-1.70 (m, 5H), 1.64-1.58 (m, 5H), 1.58-1.53 (m, 3H), 1.53 (s, 3H), 1.49-1.43 (m, 2H), 1.43-1.33 (m, 3H), 1.33-1.23 (m, 1H), 1.23-1.11 (m, 5H), 1.09-1.01 (m, 1H), 0.98 (d, J=6.5 Hz, 3H), 0.94-0.88 (m, 2H), 0.87-0.81 (m, 7H), 0.80-0.74 (m, 6H), 0.53 (q, J=11.8 Hz, 1H).

Example 8. Synthesis of Compound 15 and Compound 16

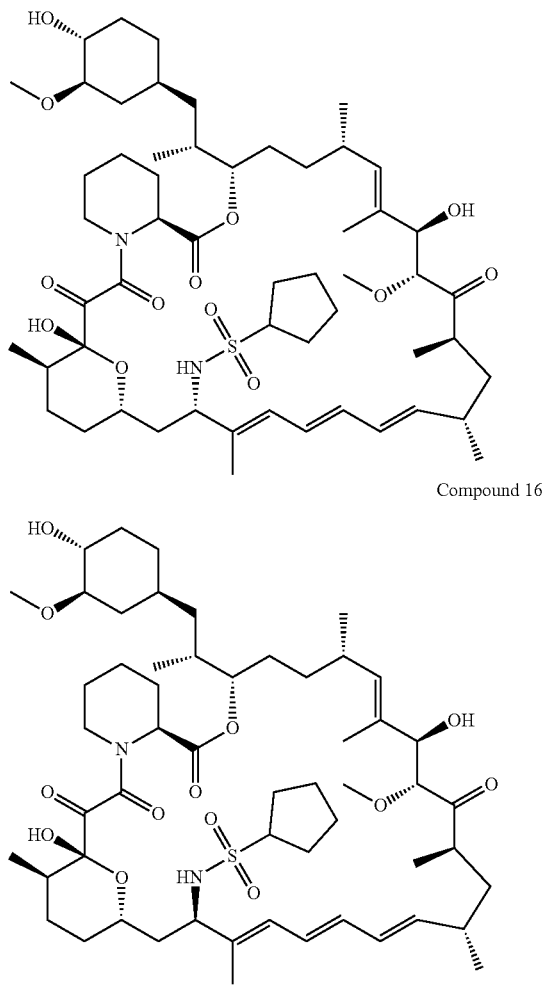

Compound 15

Compound 16

To a solution of Intermediate 1 (120 mg, 0.133 mmol) and cyclopentanesulfonamide (298 mg, 2.00 mmol) in DCM (7 mL) was added zinc(II) chloride (1M solution in diethyl ether, 0.67 mL, 0.67 mmol). The reaction mixture was stirred at room temperature for eleven minutes. The reaction was diluted with $H_2O$ and was extracted with ethylacetate. The organic extract was evaporated under reduced pressure to give a product mixture of both diastereomers. The diastereomeric mixture was separated by flash chromatography (silica; MeCN/DCM 0:100 to 50:50).

The first eluting diastereomer was purified using SFC chromatography (method 1) followed by preparative HPLC (method 2) to afford Compound 15 (4.8 mg, 3.4% yield) as a white solid.

Compound 15: ESIMS $[M+NH_4]^+$ 1034.9, $[M-H]^-$ 1015.9

$^1$H NMR (400 MHz, DMSO-$d_6$) δ: 7.48 (d, J=9.2 Hz, 1H), 6.54 (s, 1H), 6.43 (dd, J=14.1, 11.0 Hz, 1H), 6.23 (dd, J=14.3, 10.7 Hz, 1H), 6.20-6.11 (m, 1H), 5.95 (dd, J=10.9, 1.6 Hz, 1H), 5.49 (dd, J=14.2, 9.6 Hz, 1H), 5.05 (s, 1H), 4.97-4.89 (m, 1H), 4.86-4.77 (m, 1H), 4.71-4.51 (m, 2H), 4.00-3.90 (m, 1H), 3.90-3.83 (m, 1H), 3.78-3.68 (m, 1H), 3.68-3.59 (m, 1H), 3.50-3.40 (m, 1H), 3.32 (s, 3H), 3.24-3.20 (m, 1H), 3.20-3.14 (m, 2H), 3.12 (s, 3H), 2.92-2.80 (m, 2H), 2.28-2.17 (m, 1H), 2.16-2.08 (m, 1H), 2.08-1.99 (m, 2H), 1.96-1.87 (m, 3H), 1.85-1.78 (m, 7H), 1.76-1.72 (m, 1H), 1.69-1.59 (m, 6H), 1.53-1.46 (m, 8H), 1.44-1.36 (m, 3H), 1.34-1.26 (m, 2H), 1.22-1.09 (m, 6H), 1.02-0.93 (m, 8H), 0.88-0.83 (m, 4H), 0.79 (d, J=6.7 Hz, 3H), 0.74 (d, J=6.7 Hz, 3H), 0.70-0.63 (m, 1H), 0.63-0.53 (m, 1H).

The second eluting diastereomer was purified using SFC chromatography (method 1) to afford Compound 16 (22.8 mg, 16.3% yield) as a white solid.

Compound 16: ESIMS $[M+NH_4]^+$ 1034.5, $[M-H]^-$ 1015.5

$^1$H NMR (400 MHz, DMSO-$d_6$) δ: 7.53-7.11 (m, 1H), 6.47-6.30 (m, 2H), 6.19-6.09 (m, 2H), 6.09-6.02 (m, 1H), 5.53 (dd, J=14.1, 8.9 Hz, 1H), 5.18-4.90 (m, 3H), 4.66 (ddd, J=9.5, 6.2, 2.5 Hz, 1H), 4.63-4.52 (m, 1H), 4.04-3.96 (m, 1H), 3.96-3.87 (m, 1H), 3.79 (d, J=4.8 Hz, 1H), 3.72-3.65 (m, 1H), 3.65-3.60 (m, 1H), 3.60-3.51 (m, 1H), 3.31 (s, 3H), 3.20-3.10 (m, 5H), 2.87-2.76 (m, 1H), 2.57-2.45 (m, 1H), 2.28-2.20 (m, 1H), 2.20-2.14 (m, 1H), 2.11-2.00 (m, 2H), 1.92-1.80 (m, 5H), 1.79-1.69 (m, 5H), 1.69-1.61 (m, 5H), 1.60-1.53 (m, 7H), 1.51 (s, 3H), 1.50-1.43 (m, 2H), 1.43-1.33 (m, 3H), 1.31-1.27 (m, 1H), 1.24-1.13 (m, 5H), 1.09-1.01 (m, 1H), 0.98 (d, J=6.5 Hz, 3H), 0.94-0.87 (m, 3H), 0.86-0.80 (m, 6H), 0.78 (d, J=6.7 Hz, 3H), 0.75 (d, J=6.6 Hz, 3H), 0.53 (q, J=11.9 Hz, 1H).

Example 9. Synthesis of Compound 17 and Compound 18

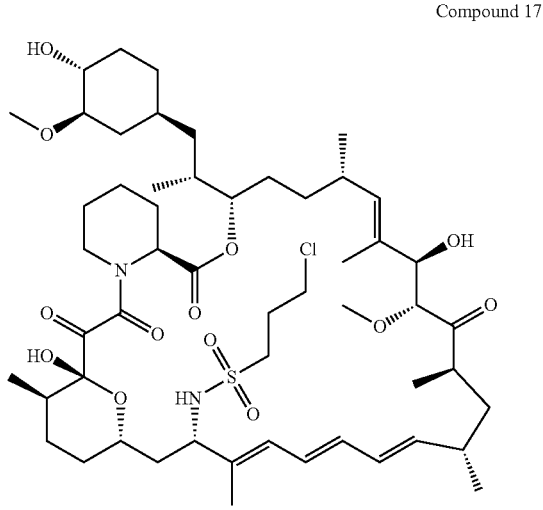

Compound 17

Compound 18

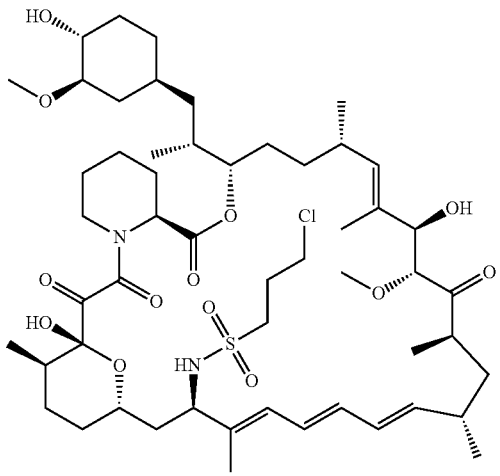

To a solution of Intermediate 1 (100 mg, 0.111 mmol) and 3-chloropropane-1-sulfonamide (263 mg, 1.67 mmol) in DCM (3 mL) was added zinc(II) chloride (1M solution in diethyl ether, 0.56 mL, 0.56 mmol). The reaction mixture was stirred at room temperature for ten minutes The reaction was diluted with $H_2O$ and was extracted with ethylacetate. The organic extract was evaporated under reduced pressure to give a product mixture of both diastereomers. The diastereomeric mixture was separated by flash chromatography (silica; MeCN/DCM 0:100 to 40:60).

The first eluting diastereomer was purified using SFC chromatography (Method 1) to afford Compound 17 (8.0 mg, 6.8% yield) as a white solid.

Compound 17: ESIMS $[M+NH_4]^+$ 1042.4, $[M–H]^-$ 1023.3

$^1$H NMR (400 MHz, DMSO-$d_6$) δ: 7.69 (d, J=9.0 Hz, 1H), 6.60 (s, 1H), 6.41 (dd, J=14.1, 11.0 Hz, 1H), 6.23 (dd, J=14.1, 10.5 Hz, 1H), 6.17 (dd, J=14.4, 10.5 Hz, 1H), 6.03-5.91 (m, 1H), 5.49 (dd, J=14.4, 9.6 Hz, 1H), 5.05 (d, J=4.6 Hz, 1H), 4.98-4.90 (m, 1H), 4.86-4.77 (m, 1H), 4.68-4.55 (m, 2H), 3.99-3.90 (m, 1H), 3.88 (dd, J=9.2, 3.8 Hz, 1H), 3.77-3.56 (m, 4H), 3.51-3.40 (m, 1H), 3.31 (s, 3H), 3.25-3.16 (m, 2H), 3.12 (s, 3H), 3.05-2.94 (m, 1H), 2.92-2.80 (m, 3H), 2.29-2.17 (m, 1H), 2.17-2.08 (m, 1H), 2.08-1.98 (m, 4H), 1.96-1.87 (m, 3H), 1.82 (s, 3H), 1.78-1.60 (m, 5H), 1.55-1.45 (m, 6H), 1.44-1.34 (m, 4H), 1.32-1.25 (m, 1H), 1.23-1.08 (m, 6H), 1.04-0.94 (m, 8H), 0.88-0.82 (m, 4H), 0.79 (d, J=6.7 Hz, 3H), 0.74 (d, J=6.7 Hz, 3H), 0.65 (d, J=9.5 Hz, 1H), 0.63-0.51 (m, 1H).

The second eluting diastereomer was purified using SFC chromatography (Method 1) to afford Compound 18 (15.0 mg, 12.9% yield) as a white solid.

Compound 18: ESIMS $[M+NH_4]^+$ 1042.4, $[M–H]^-$ 1023.4

$^1$H NMR (400 MHz, DMSO-$d_6$) δ: 7.48 (d, J=7.9 Hz, 1H), 6.45 (s, 1H), 6.43-6.35 (m, 1H), 6.20-6.10 (m, 2H), 6.09-6.03 (m, 1H), 5.53 (dd, J=14.2, 8.9 Hz, 1H), 5.09-4.97 (m, 3H), 4.71-4.62 (m, 1H), 4.59 (d, J=4.4 Hz, 1H), 4.03-3.96 (m, 1H), 3.93-3.83 (m, 1H), 3.80-3.69 (m, 4H), 3.68-3.58 (m, 1H), 3.31 (s, 3H), 3.20-3.11 (m, 6H), 3.08-3.02 (m, 1H), 2.81 (ddd, J=11.1, 8.6, 4.3 Hz, 1H), 2.55-2.50 (m, 1H), 2.29-2.19 (m, 1H), 2.16-2.02 (m, 5H), 1.96-1.85 (m, 1H), 1.80-1.70 (m, 5H), 1.69-1.34 (m, 16H), 1.33-1.10 (m, 6H), 1.09-1.02 (m, 1H), 1.00-0.97 (m, 3H), 0.94-0.89 (m, 2H), 0.88-0.81 (m, 7H), 0.79 (d, J=6.6 Hz, 3H), 0.75 (d, J=6.6 Hz, 3H), 0.54 (q, J=11.9 Hz, 1H).

Example 10. Synthesis of Compound 19 and Compound 20

Compound 19

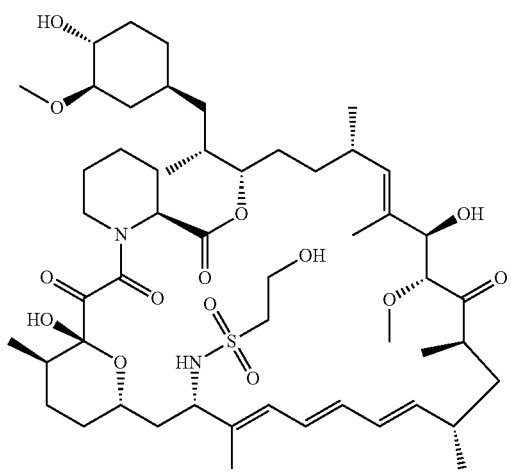

Compound 20

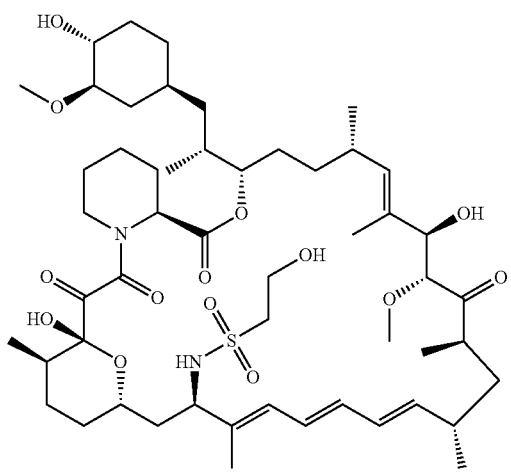

To a solution of Intermediate 1 (100 mg, 0.111 mmol) and 2-hydroxyethanesulfonamide (139 mg, 1.11 mmol) in DCM (7 mL) was added zinc(II) chloride (1M solution in diethyl ether, 0.55 mL, 0.55 mmol). The reaction mixture was stirred at room temperature for 30 minutes. The reaction was diluted with $H_2O$ and was extracted with ethyl acetate. The organic extract was evaporated under reduced pressure to give a product mixture of both diastereomers. The diastereomeric mixture was separated by flash chromatography (silica; MeCN/DCM 0:100 to 70:30).

The first eluting diastereomer was purified using SFC chromatography (method 1) to afford Compound 19 (2.2 mg, 1.8% yield) as a white solid.

Compound 19: ESIMS $[M–H]^-$ 991.9

$^1$H NMR (400 MHz, DMSO-$d_6$) δ: 6.44 (dd, J=14.0, 10.9 Hz, 1H), 6.29-6.13 (m, 2H), 5.96 (d, J=10.6 Hz, 1H), 5.50 (dd, J=14.2, 9.6 Hz, 1H), 4.96-4.90 (m, 1H), 4.82 (d, J=9.9 Hz, 1H), 4.68-4.56 (m, 1H), 3.97-3.84 (m, 2H), 3.78-3.68 (m, 1H), 3.68-3.58 (m, 3H), 3.48-3.40 (m, 1H), 3.39-3.26

(m, 3H), 3.24-3.13 (m, 2H), 3.12 (s, 3H), 3.05-2.79 (m, 4H), 2.28-2.18 (m, 1H), 2.18-1.99 (m, 3H), 1.99-1.83 (m, 3H), 1.81 (s, 3H), 1.79-1.58 (m, 5H), 1.57-1.08 (m, 17H), 1.06-0.89 (m, 8H), 0.89-0.82 (m, 4H), 0.79 (d, J=6.7 Hz, 3H), 0.74 (d, J=6.7 Hz, 3H), 0.70-0.53 (m, 2H).

The second eluting diastereomer was purified using SFC chromatography (method 1) to afford Compound 20 (9.0 mg, 7.8% yield) as a white solid.

Compound 20: ESIMS [M–H]⁻ 991.9

$^1$H NMR (400 MHz, DMSO-d$_6$) δ: 7.32 (d, J=7.8 Hz, 1H), 6.50-6.32 (m, 2H), 6.21-6.08 (m, 2H), 6.08-6.03 (m, 1H), 5.56 (dd, J=14.1, 8.7 Hz, 1H), 5.06-4.99 (m, 3H), 4.85 (s, 1H), 4.71-4.62 (m, 1H), 4.61-4.54 (m, 1H), 4.02-3.88 (m, 2H), 3.81-3.67 (m, 4H), 3.65-3.58 (m, 1H), 3.37-3.25 (m, 3H), 3.20-3.09 (m, 7H), 2.85-2.77 (m, 1H), 2.60-2.53 (m, 1H), 2.28-2.19 (m, 1H), 2.19-1.96 (m, 3H), 1.95-1.87 (m, 1H), 1.82-1.70 (m, 5H), 1.69-1.35 (m, 16H), 1.33-1.11 (m, 6H), 1.11-0.96 (m, 4H), 0.95-0.81 (m, 9H), 0.79 (d, J=6.6 Hz, 3H), 0.75 (d, J=6.6 Hz, 3H), 0.54 (q, J=11.8 Hz, 1H).

Example 11. Synthesis of Compound 21 and Compound 22

Compound 21

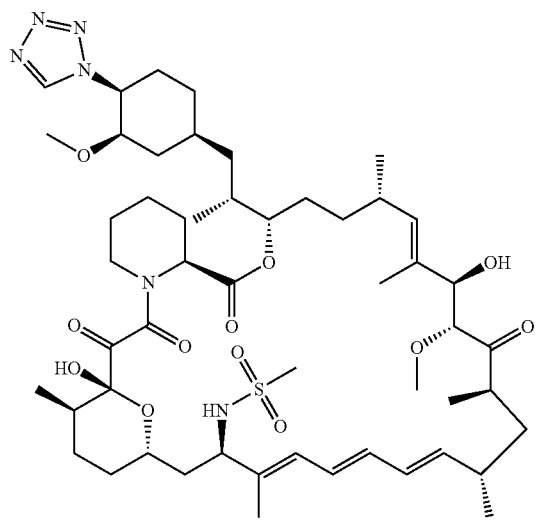

To a solution of Intermediate 2 (100 mg, 0.105 mmol) and methanesulfonamide (100 mg, 1.05 mmol) in DCM (25 mL) was added zinc(II) chloride (1M solution in diethyl ether, 0.53 mL, 0.53 mmol). The reaction mixture was stirred at room temperature for 1 hour. The reaction was diluted with H$_2$O and was extracted with ethyl acetate. The organic extract was evaporated under reduced pressure to give a product mixture of both diastereomers. The diastereomeric mixture was separated by reversed phase preparative HPLC chromatography (method 1) The first eluting diastereomer was purified using SFC chromatography (method 1) to afford Compound 21 (4.5 mg, 4.0% yield) as a white solid.

Compound 21: ESIMS [M–H]⁻ 1014.0

$^1$H NMR (400 MHz, DMSO-d$_6$) δ: 9.28 (s, 1H), 7.27 (s, 1H), 6.58-6.34 (m, 2H), 6.26-6.08 (m, 2H), 6.09-6.00 (m, 1H), 5.53 (dd, J=14.1, 8.8 Hz, 1H), 5.24-5.12 (m, 1H), 5.09-4.97 (m, 3H), 4.76-4.64 (m, 1H), 3.99-3.96 (m, 1H), 3.95-3.85 (m, 1H), 3.84-3.75 (m, 1H), 3.67 (d, J=5.7 Hz, 1H), 3.64-3.56 (m, 2H), 3.45-3.17 (m, 4H), 3.14 (s, 3H), 2.88 (s, 3H), 2.62-2.54 (m, 1H), 2.30-2.08 (m, 4H), 2.08-1.99 (m, 1H), 1.98-1.87 (m, 1H), 1.83-1.34 (m, 22H), 1.33-1.14 (m, 5H), 1.12-0.79 (m, 16H), 0.69 (d, J=6.7 Hz, 3H).

The second eluting diastereomer was purified using SFC chromatography (method 1) to afford Compound 22 (5.5 mg, 4.8% yield) as a white solid.

Compound 22: ESIMS [M–H]⁻ 1014.1

$^1$H NMR (400 MHz, DMSO-d$_6$) δ: 9.32 (s, 1H), 7.48 (s, 1H), 6.72-6.38 (m, 2H), 6.33-6.12 (m, 2H), 5.98 (d, J=10.9 Hz, 1H), 5.50 (dd, J=14.2, 9.6 Hz, 1H), 5.26-5.15 (m, 1H), 5.05 (s, 1H), 4.99-4.92 (m, 1H), 4.83 (d, J=9.8 Hz, 1H), 4.64-4.54 (m, 1H), 3.97-3.80 (m, 2H), 3.79-3.70 (m, 1H), 3.68-3.57 (m, 2H), 3.48-3.41 (m, 1H), 3.26 (s, 3H), 3.21 (d, J=9.2 Hz, 1H), 3.09 (s, 3H), 2.91-2.78 (m, 1H), 2.71 (s, 3H), 2.30-1.85 (m, 7H), 1.80 (s, 3H), 1.77-1.61 (m, 5H), 1.61-1.35 (m, 13H), 1.33-0.89 (m, 14H), 0.86 (d, J=6.5 Hz, 3H), 0.81 (d, J=6.7 Hz, 3H), 0.77-0.55 (m, 4H).

Example 12. Synthesis of Compound 23 and Compound 24

Compound 22

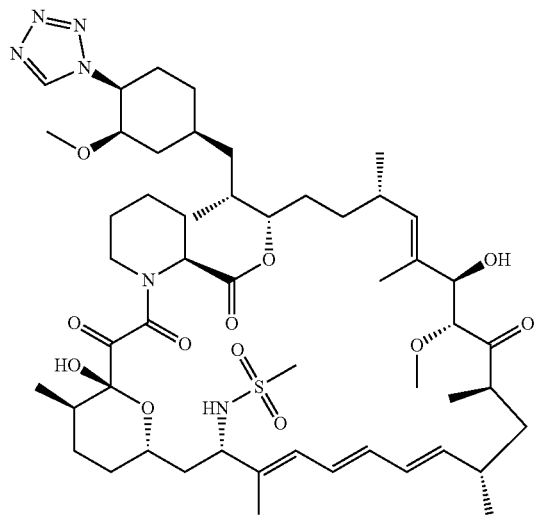

Compound 23

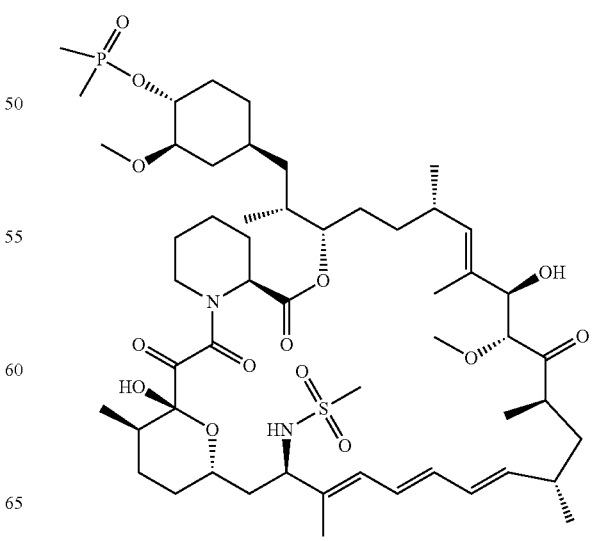

Compound 24

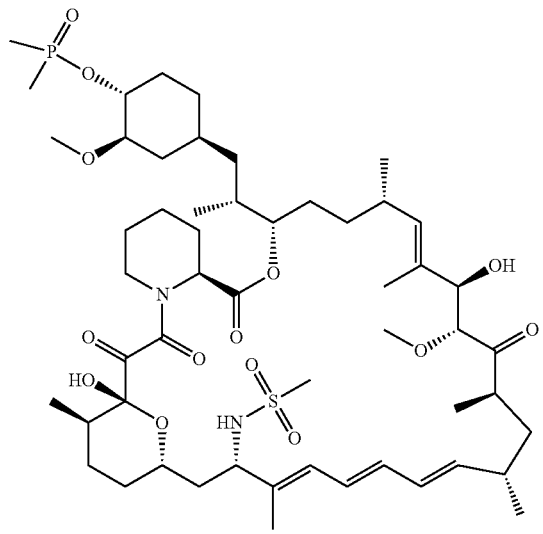

To a solution of Intermediate 3 (100 mg, 0.102 mmol) and methanesulfonamide (97 mg, 1.0 mmol) in DCM (7 mL) was added zinc(II) chloride (1M solution in diethyl ether, 0.51 mL, 0.51 mmol). The reaction mixture was stirred at room temperature for 30 minutes. The reaction was diluted with H$_2$O and was extracted with ethyl acetate. The organic extract was evaporated under reduced pressure to give a product mixture of both diastereomers. The diastereomeric mixture was separated by reversed phase preparative HPLC chromatography (Method 1).

The first eluting diastereomer was isolated to afford Compound 23 (5.6 mg, 4.6% yield) as a white solid.

Compound 23: ESIMS [M–H]$^-$ 1037.4

$^1$H NMR (400 MHz, DMSO-d$_6$) δ: 7.30 (d, J=7.7 Hz, 1H), 6.48 (s, 1H), 6.46-6.33 (m, 1H), 6.23-6.08 (m, 2H), 6.05 (d, J=11.0 Hz, 1H), 5.54 (dd, J=14.2, 8.8 Hz, 1H), 5.11-4.97 (m, 3H), 4.73-4.62 (m, 1H), 4.06-3.84 (m, 3H), 3.81-3.70 (m, 2H), 3.68-3.59 (m, 1H), 3.37-3.26 (m, 3H), 3.21-3.11 (m, 4H), 3.11-2.99 (m, 1H), 2.89 (s, 3H), 2.59-2.51 (m, 1H), 2.30-1.86 (m, 6H), 1.80-1.68 (m, 4H), 1.66-1.46 (m, 14H), 1.46-1.11 (m, 14H), 1.10-0.87 (m, 7H), 0.88-0.82 (m, 6H), 0.79 (d, J=6.6 Hz, 3H), 0.75 (d, J=6.6 Hz, 3H), 0.69-0.52 (m, 1H).

The second eluting diastereomer was purified using SFC chromatography (method 1), followed by reversed phase preparative HPLC chromatography (method 3) to afford Compound 24 (5.3 mg, 4.7% yield) as a white solid.

Compound 24: ESIMS [M–H]$^-$ 1037.9

$^1$H NMR (400 MHz, DMSO-d$_6$) δ: 7.49 (d, J=9.3 Hz, 1H), 6.60 (s, 1H), 6.45 (dd, J=14.1, 11.1 Hz, 1H), 6.31-6.11 (m, 2H), 5.98 (d, J=10.9 Hz, 1H), 5.50 (dd, J=14.3, 9.6 Hz, 1H), 5.06 (d, J=4.6 Hz, 1H), 5.01-4.91 (m, 1H), 4.82 (d, J=9.8 Hz, 1H), 4.62-4.52 (m, 1H), 4.06-3.80 (m, 3H), 3.78-3.68 (m, 1H), 3.68-3.56 (m, 1H), 3.50-3.40 (m, 1H), 3.29 (s, 3H), 3.23 (d, J=9.1 Hz, 1H), 3.12 (s, 3H), 3.08-2.98 (m, 1H), 2.91-2.77 (m, 1H), 2.71 (s, 3H), 2.30-1.84 (m, 8H), 1.81 (s, 3H), 1.78-1.59 (m, 4H), 1.58-1.27 (m, 19H), 1.26-1.09 (m, 4H), 1.08-0.90 (m, 10H), 0.86 (d, J=6.4 Hz, 3H), 0.80 (d, J=6.7 Hz, 3H), 0.76-0.60 (m, 4H).

Example 13. Synthesis of Intermediate 4-A, Intermediate 4-B, and Compound 25

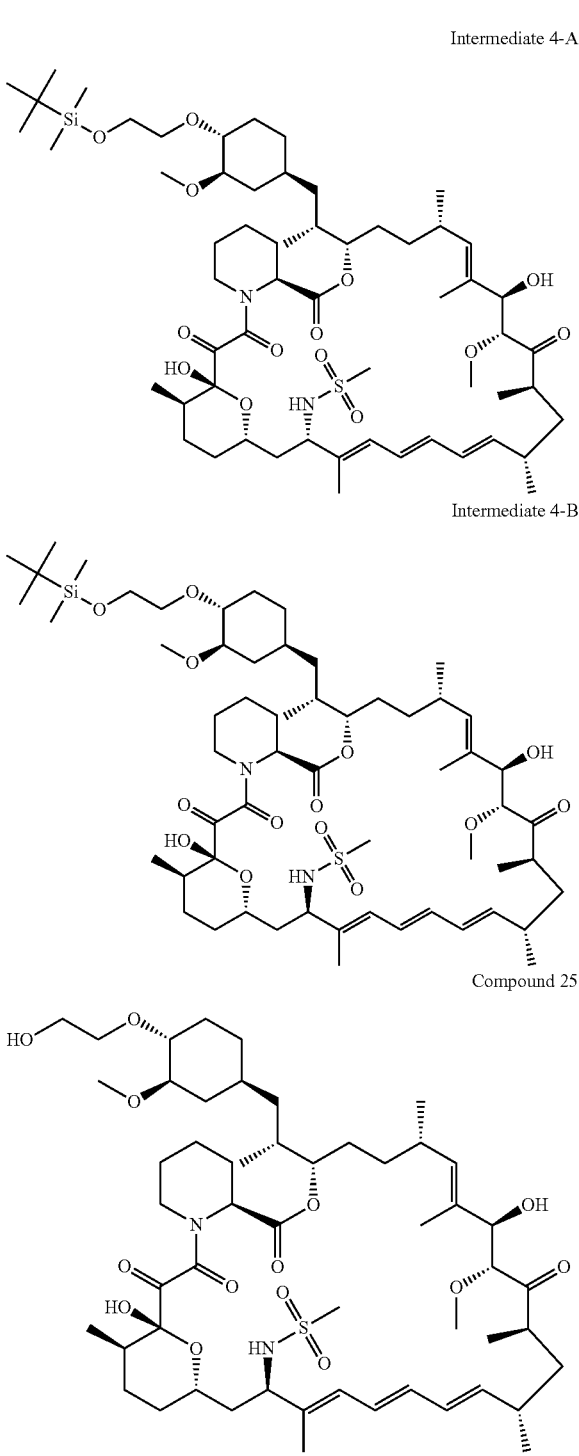

Intermediate 4-A

Intermediate 4-B

Compound 25

To a solution of Intermediate 4 (100 mg, 0.094 mmol) and methanesulfonamide (180 mg, 1.88 mmol) in DCM (10 mL) was added zinc(II) chloride (1M solution in diethyl ether, 0.47 mL, 0.47 mmol). The reaction mixture was stirred at room temperature for 30 minutes. The reaction was diluted with H$_2$O and was extracted with dichloromethane. The organic extract was evaporated under reduced pressure. The crude product was separated by flash chromatography (silica; cyclohexane/EtOAc 100:0 to 0:100).

The first eluting peak, containing a mixture of diastereomers, was separated using SFC chromatography (method 1) to afford Intermediate 4-A (6.0 mg, 5.4% yield) as a white solid.

Intermediate 4-A: ESIMS [M−H]⁻ 1119.9

$^1$H NMR (400 MHz, DMSO-$d_6$) δ: 7.49 (d, J=9.4 Hz, 1H), 6.59 (s, 1H), 6.43 (dd, J=14.4, 11.1 Hz, 1H), 6.30-6.11 (m, 2H), 5.98 (d, J=11.2, 1.5 Hz, 1H), 5.51 (dd, J=14.6, 9.5 Hz, 1H), 5.05 (d, J=4.7 Hz, 1H), 4.97-4.90 (m, 1H), 4.86-4.77 (m, 1H), 4.65-4.56 (m, 1H), 3.99-3.80 (m, 2H), 3.78-3.69 (m, 1H), 3.68-3.58 (m, 3H), 3.57-3.50 (m, 2H), 3.48-3.40 (m, 1H), 3.31 (s, 3H), 3.22 (d, J=9.2 Hz, 1H), 3.16-3.05 (m, 4H), 3.04-2.93 (m, 1H), 2.90-2.76 (m, 1H), 2.70 (s, 3H), 2.27-2.18 (m, 1H), 2.17-1.84 (m, 7H), 1.81 (s, 3H), 1.77-1.59 (m, 3H), 1.59-1.45 (m, 6H), 1.44-1.08 (m, 12H), 1.07-0.91 (m, 8H), 0.90-0.81 (m, 14H), 0.79 (d, J=6.7 Hz, 3H), 0.74 (d, J=6.7 Hz, 3H), 0.70-0.57 (m, 1H), 0.03 (s, 6H).

The fraction of the SFC purification, containing the second diastereomer, was purified by reversed phase preparative HPLC chromatography (method 4) to afford Intermediate 4-B (5.0 mg, 4.2% yield) as a white solid.

Intermediate 4-B: ESIMS [M−H]⁻ 1119.6

$^1$H NMR (400 MHz, DMSO-$d_6$) δ: 7.29 (d, J=7.6 Hz, 1H), 6.46 (s, 1H), 6.44-6.33 (m, 1H), 6.23-6.08 (m, 2H), 6.05 (d, J=11.1 Hz, 1H), 5.54 (dd, J=14.2, 9.0 Hz, 1H), 5.07-4.96 (m, 3H), 4.74-4.62 (m, 1H), 4.01-3.96 (m, 1H), 3.95-3.87 (m, 1H), 3.81-3.69 (m, 2H), 3.68-3.58 (m, 3H), 3.56-3.50 (m, 2H), 3.38-3.25 (m, 3H), 3.23-3.11 (m, 4H), 3.10-3.00 (m, 1H), 3.00-2.91 (m, 1H), 2.89 (s, 3H), 2.60-2.52 (m, 1H), 2.28-2.18 (m, 1H), 2.18-2.01 (m, 3H), 2.00-1.84 (m, 2H), 1.80-1.70 (m, 4H), 1.70-1.46 (m, 17H), 1.46-1.00 (m, 6H), 1.00-0.91 (m, 4H), 0.91-0.81 (m, 16H), 0.80-0.69 (m, 7H), 0.65-0.51 (m, 1H), 0.03 (s, 6H).

The second eluting peak was purified using SFC chromatography (method 1) to afford Compound 25 (5.5 mg, 5.5% yield) as a white solid.

Compound 25: ESIMS [M−H]⁻ 1005.4

$^1$H NMR (400 MHz, DMSO-$d_6$) δ: 7.30 (d, J=7.8 Hz, 1H), 6.47 (s, 1H), 6.40 (dd, J=13.7, 11.2 Hz, 1H), 6.20-6.08 (m, 2H), 6.05 (d, J=11.0 Hz, 1H), 5.54 (dd, J=14.3, 8.8 Hz, 1H), 5.08-4.97 (m, 3H), 4.70-4.62 (m, 1H), 4.49-4.38 (m, 1H), 4.02-3.96 (m, 1H), 3.95-3.87 (m, 1H), 3.80-3.70 (m, 2H), 3.67-3.58 (m, 1H), 3.55-3.41 (m, 4H), 3.37-3.24 (m, 3H), 3.22-3.10 (m, 4H), 3.04-2.92 (m, 2H), 2.89 (s, 3H), 2.60-2.49 (m, 1H), 2.27-2.19 (m, 1H), 2.18-1.99 (m, 3H), 1.98-1.87 (m, 2H), 1.83-1.71 (m, 4H), 1.70-1.34 (m, 15H), 1.32-1.00 (m, 7H), 1.00-0.88 (m, 5H), 0.88-0.81 (m, 8H), 0.81-0.69 (m, 6H), 0.59 (q, J=11.7 Hz, 1H).

Example 14. Synthesis of Compound 26

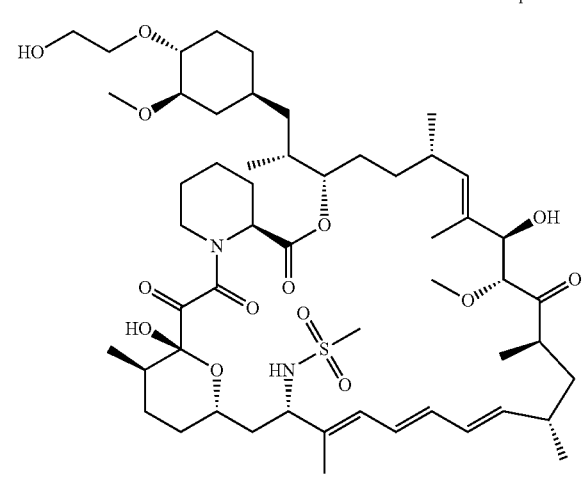

Compound 26

To a mixture of Intermediate 4-B (30 mg, 0.027 mmol) in hexane (1 mL), EtOAc (1 mL) and H$_2$O (1 mL) was added acetic acid (0.1 mL). The reaction mixture was stirred at room temperature for 4 hours. The reaction was diluted with H$_2$O and was extracted with ethyl acetate. The organic extract was evaporated under reduced pressure. The crude product was purified by SFC chromatography (method 1) to afford Compound 26 (4.5 mg, 16% yield) as a white solid.

Compound 26: ESIMS [M−H]⁻ 1005.9

$^1$H NMR (400 MHz, DMSO-$d_6$) δ: 7.49 (d, J=9.3 Hz, 1H), 6.59 (s, 1H), 6.44 (dd, J=14.3, 11.0 Hz, 1H), 6.30-6.11 (m, 2H), 6.02-5.94 (m, 1H), 5.50 (dd, J=14.5, 9.5 Hz, 1H), 5.05 (d, J=4.6 Hz, 1H), 4.98-4.89 (m, 1H), 4.82 (d, J=9.8 Hz, 1H), 4.64-4.54 (m, 1H), 4.46 (s, 1H), 3.99-3.78 (m, 2H), 3.77-3.68 (m, 1H), 3.68-3.58 (m, 1H), 3.57-3.41 (m, 5H), 3.40-3.26 (m, 3H), 3.22 (d, J=9.2 Hz, 1H), 3.12 (s, 3H), 3.10-2.93 (m, 2H), 2.91-2.77 (m, 1H), 2.70 (s, 3H), 2.28-1.83 (m, 8H), 1.81 (s, 3H), 1.77-1.46 (m, 10H), 1.45-1.07 (m, 12H), 1.07-0.89 (m, 8H), 0.89-0.82 (m, 4H), 0.79 (d, J=6.7 Hz, 3H), 0.74 (d, J=6.7 Hz, 3H), 0.71-0.55 (m, 1H).

Example 15. Synthesis of Compound 27

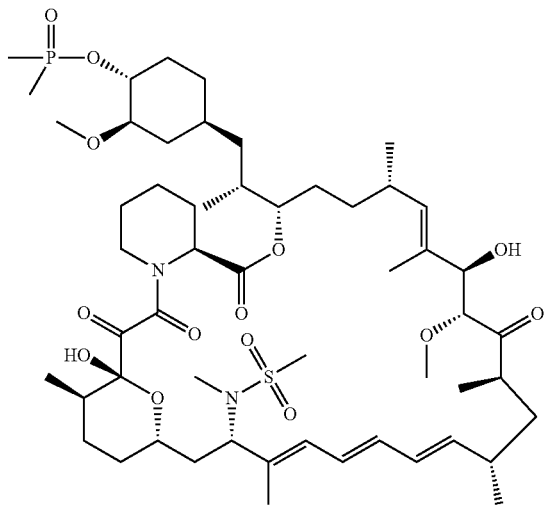 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(C)S(C)(=O)=O)C[C@@H]3CC[C@@H](C)[C@@](O)(O3)C(=O)C(=O)N3CCCC[C@H]3C(=O)O2)CC[C@H]1OP(C)(C)=O]

To a solution of Intermediate 3 (100 mg, 0.102 mmol) and N-methylmethanesulfonamide (112 mg, 1.02 mmol) in DCM (7 mL) was added zinc(II) chloride (1M solution in diethyl ether, 0.51 mL, 0.51 mmol). The reaction mixture was stirred at room temperature for 30 minutes. The reaction was diluted with $H_2O$ and was extracted with ethyl acetate. The organic extract was evaporated under reduced pressure. The crude product was purified using SFC chromatography (method 1) to afford Compound 27 (25 mg, 22% yield) as a white solid.

Compound 27: ESIMS [M−H]⁻ 1051.4

$^1$H NMR (400 MHz, DMSO-$d_6$) δ: 6.49 (dd, J=14.1, 10.9 Hz, 1H), 6.35 (s, 1H), 6.30-6.12 (m, 2H), 5.99 (d, J=10.9 Hz, 1H), 5.46 (dd, J=14.4, 9.7 Hz, 1H), 5.07 (d, J=4.9 Hz, 1H), 4.98-4.87 (m, 2H), 4.75-4.63 (m, 1H), 4.60-4.48 (m, 1H), 4.02-3.90 (m, 2H), 3.80-3.69 (m, 1H), 3.68-3.55 (m, 1H), 3.53-3.26 (m, 5H), 3.22-2.97 (m, 7H), 2.84-2.72 (m, 1H), 2.51 (s, 3H), 2.29-2.13 (m, 2H), 2.13-1.89 (m, 4H), 1.80 (s, 3H), 1.76-1.06 (m, 30H), 1.04-0.90 (m, 8H), 0.88 (d, J=6.3 Hz, 3H), 0.83-0.59 (m, 8H).

Example 16. Synthesis of Compound 28 and Compound 29

Compound 28

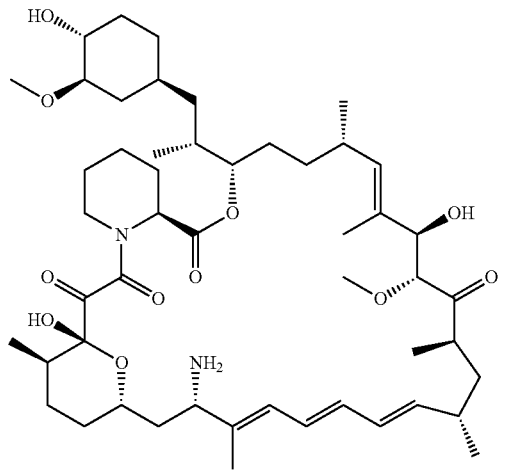 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)C(N(C)S(C)(=O)=O)C[C@@H]3CC[C@@H](C)[C@@](O)(O3)C(=O)C(=O)N3CCCC[C@H]3C(=O)O2)CC[C@H]1O]

Compound 29

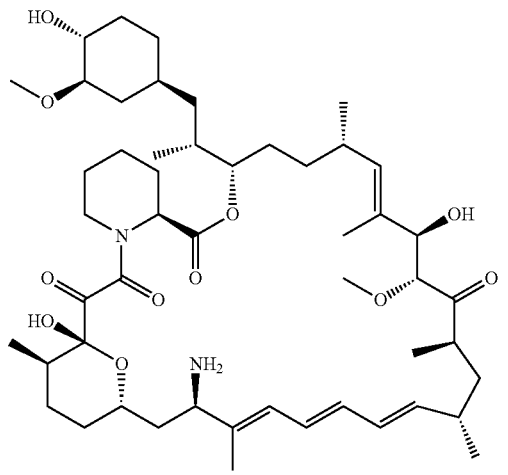

Diastereomer 1: A solution of Intermediate 7 (68 mg, 0.069 mmol) in HCl (4M solution in dioxane, 1.35 mL, 5.52 mmol was stirred at room temperature for one hour. The reaction was directly freeze dried to give the crude product. The crude diastereomer was purified by preparative HPLC (method 1) to afford Compound 28 (4.4 mg, 6.7% yield) as a white solid.

Compound 28: ESIMS [M+H]⁺ 885.6, [M+FA−H]⁻ 929.6

$^1$H NMR (400 MHz, DMSO-$d_6$) δ: 6.47-6.40 (m, 1H), 6.21-6.12 (m, 2H), 5.96-5.87 (m, 1H), 5.46 (dd, J=14.0, 9.2 Hz, 1H), 4.98-4.93 (m, 1H), 4.89-4.81 (m, 1H), 4.66-4.59 (m, 1H), 4.02-3.94 (m, 1H), 3.91-3.86 (m, 1H), 3.64-3.55 (m, 1H), 3.48-3.40 (m, 1H), 3.31 (s, 3H), 3.29-3.24 (m, 2H), 3.21-3.16 (m, 1H), 3.12 (s, 3H), 2.88-2.80 (m, 2H), 2.24-2.17 (m, 1H), 2.17-2.10 (m, 1H), 2.09-2.01 (m, 1H), 1.97-1.90 (m, 2H), 1.88-1.82 (m, 1H), 1.81-1.74 (m, 5H), 1.74-1.70 (m, 2H), 1.68-1.61 (m, 2H), 1.54-1.47 (m, 6H), 1.44-1.37 (m, 3H), 1.34-1.27 (m, 2H), 1.25-1.09 (m, 6H), 1.07-1.00 (m, 2H), 0.98-0.95 (m, 6H), 0.88-0.83 (m, 4H), 0.79 (d, J=6.7 Hz, 3H), 0.75-0.69 (m, 4H), 0.59 (q, J=11.9 Hz, 1H).

Diastereomer 2: A solution of Intermediate 8 (75 mg, 0.076 mmol) in HCl (4M solution in dioxane, 0.95 mL, 3.8 mmol) was stirred at room temperature for one hour. The reaction was directly freeze dried to give the crude product. The crude diastereomer was purified by preparative HPLC (method 1) to afford Compound 29 (10.9 mg, 15.8% yield) as a white solid.

Compound 29: ESIMS [M+H]⁺ 885.9, [M+FA−H]⁻ 930.2

$^1$H NMR (400 MHz, DMSO-d6) δ: 6.50-6.40 (m, 1H), 6.24-6.11 (m, 3H), 5.60 (dd, J=14.1, 8.7 Hz, 1H), 5.06-5.01 (m, 1H), 4.95 (d, J=9.7 Hz, 1H), 4.70-4.63 (m, 1H), 4.04-3.98 (m, 1H), 3.98-3.92 (m, 1H), 3.69-3.61 (m, 2H), 3.57 (d, J=6.8 Hz, 1H), 3.31 (s, 3H), 3.27-3.21 (m, 1H), 3.20-3.16 (m, 1H), 3.15 (s, 3H), 2.82 (ddd, J=11.2, 8.7, 4.4 Hz, 1H), 2.76-2.67 (m, 1H), 2.29-2.20 (m, 1H), 2.19-2.13 (m, 1H), 2.12-2.01 (m, 2H), 1.95-1.89 (m, 1H), 1.85-1.80 (m, 3H), 1.78-1.71 (m, 3H), 1.68-1.55 (m, 5H), 1.55-1.49 (m, 6H), 1.49-1.46 (m, 2H), 1.45-1.38 (m, 2H), 1.33-1.10 (m, 7H), 1.02-0.97 (m, 4H), 0.92-0.85 (m, 5H), 0.84-0.79 (m, 6H), 0.74 (d, J=6.7 Hz, 3H), 0.57 (q, J=11.8 Hz, 1H).

Figure 2:
FIG. 2 depicts the x-ray co-crystal structure of Compound 29 with FKBP12. The C16 substituent is in (R)-configuration.

The absolute configuration of the C16 substituent in Compound 29 was determined by X-ray crystallographic co-crystallization with FKBP12. Based on the x-ray co-crystal structure, the C16 substituent in Compound 29 is in the (R)-configuration. The crystal structure is depicted in FIG. 2.

Example 17. Synthesis of Compound 30 and Compound 31

Compound 30

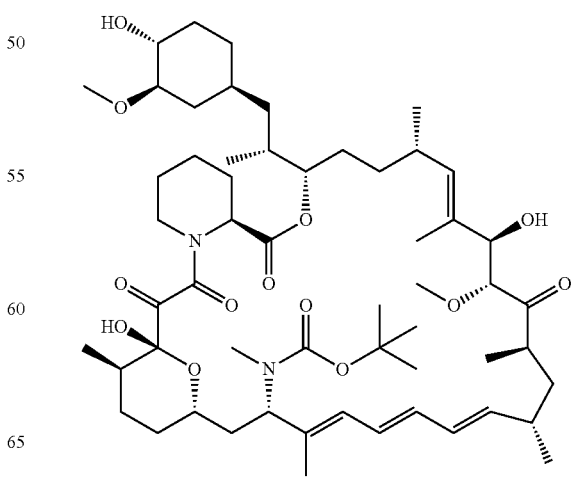

Compound 31

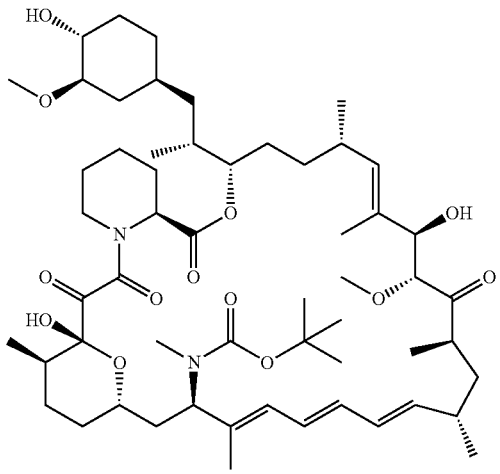

To a mixture of Intermediate 1 (350 mg, 0.389 mmol) and tert-butyl methylcarbamate (765 mg, 5.83 mmol) in DCM (3 mL) was added 4-methylbenzenesulfonic acid hydrate (74 mg, 0.389 mmol). The reaction mixture was stirred at room temperature for 23 hours. The entire reaction mixture containing a product mixture of both diastereomers was separated by reversed phase flash chromatography (C18; MeCN/H$_2$O 40:60 to 90:10).

The first eluting diastereomer was purified using SFC chromatography (method 3) followed by preparative HPLC (method 2) to afford Compound 30 (22 mg, 5.4% yield) as a white solid.

Compound 30: ESIMS [M+NH$_4$]$^+$ 1017.2, [M+FA−H]$^-$ 1044.2

$^1$H NMR (400 MHz, DMSO-d$_6$) δ: 6.61-6.51 (m, 1H), 6.50-6.45 (m, 1H), 6.24-6.15 (m, 2H), 5.99 (d, J=11.0 Hz, 1H), 5.66 (dd, J=14.2, 8.4 Hz, 1H), 5.07 (d, J=4.7 Hz, 1H), 5.04-5.00 (m, 1H), 4.89 (d, J=9.6 Hz, 1H), 4.72-4.65 (m, 1H), 4.59 (d, J=4.4 Hz, 1H), 4.48-4.29 (m, 1H), 3.91 (dd, J=8.6, 4.6 Hz, 1H), 3.73-3.61 (m, 1H), 3.54-3.42 (m, 2H), 3.34 (d, J=8.1 Hz, 1H), 3.30 (s, 3H), 3.20-3.16 (m, 1H), 3.14 (s, 3H), 2.96-2.88 (m, 1H), 2.86-2.79 (m, 1H), 2.59 (s, 3H), 2.28-2.19 (m, 2H), 2.17-2.10 (m, 1H), 2.08-2.00 (m, 2H), 1.96-1.90 (m, 1H), 1.86-1.80 (m, 1H), 1.77-1.62 (m, 8H), 1.56-1.46 (m, 6H), 1.43-1.26 (m, 17H), 1.23-1.09 (m, 4H), 1.07-1.02 (m, 1H), 1.01-0.94 (m, 6H), 0.89-0.81 (m, 8H), 0.73 (d, J=6.7 Hz, 3H), 0.58 (q, J=11.9 Hz, 1H).

The second eluting diastereomer was purified using SFC chromatography (method 3) followed by preparative HPLC (method 2) to afford Compound 31 (45 mg, 11.2% yield) as a white solid.

Compound 31: ESIMS [M+NH$_4$]$^+$ 1017.2, [M+FA−H]$^-$ 1044.3

$^1$H NMR (400 MHz, DMSO-d$_6$) δ: 6.49-6.40 (m, 1H), 6.27-6.11 (m, 2H), 5.98-5.84 (m, 1H), 5.53-5.36 (m, 1H), 5.10-5.05 (m, 1H), 5.02-4.91 (m, 2H), 4.64-4.54 (m, 2H), 4.44-4.19 (m, 1H), 4.06-3.92 (m, 1H), 3.77-3.64 (m, 1H), 3.65-3.50 (m, 2H), 3.51-3.39 (m, 1H), 3.33 (s, 3H), 3.21-3.16 (m, 1H), 3.13 (s, 3H), 2.90-2.79 (m, 1H), 2.69-2.61 (m, 1H), 2.51 (s, 3H), 2.26-2.13 (m, 2H), 2.09-2.00 (m, 2H), 1.94-1.88 (m, 1H), 1.78-1.67 (m, 5H), 1.67-1.65 (m, 1H), 1.63-1.48 (m, 10H), 1.47-1.44 (m, 1H), 1.42-1.30 (m, 12H), 1.29-1.22 (m, 3H), 1.22-1.12 (m, 4H), 1.12-1.01 (m, 1H), 1.01-0.95 (m, 4H), 0.92-0.81 (m, 8H), 0.80-0.73 (m, 6H), 0.60 (q, J=11.9 Hz, 1H).

Example 18. Synthesis of Compound 32 and Compound 33

Compound 32

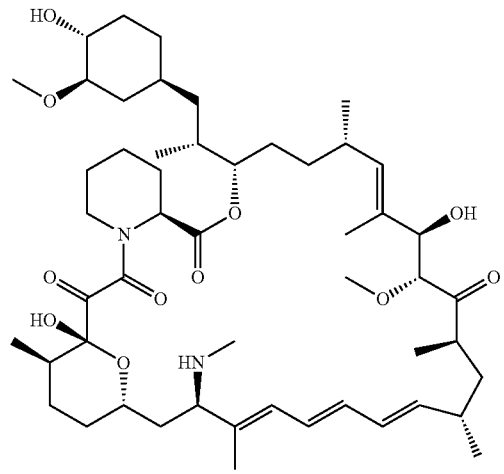

Compound 33

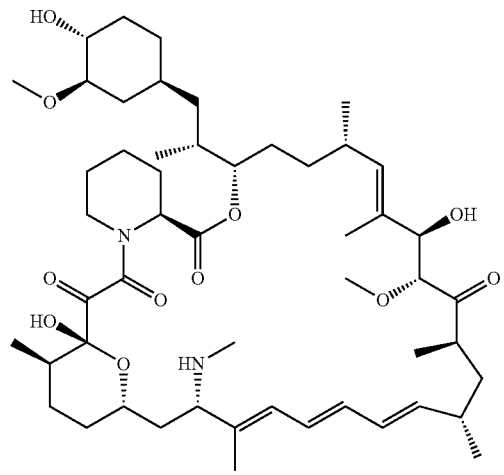

Diastereomer 1: A solution of Compound 31 (44 mg, 0.044 mmol) in HCl (4M solution in dioxane, 550 µL, 2.20 mmol) was stirred at room temperature for six minutes. The reaction was directly freeze dried to give the crude product. The crude diastereomer was purified by preparative HPLC (method 2) to afford Compound 32 (11.5 mg, 27.4% yield) as a white solid.

Compound 32: ESIMS [M+H]$^+$ 899.9, [M+FA−H]$^-$ 945.2

$^1$H NMR (400 MHz, DMSO-d$_6$) δ: 9.08-8.59 (m, 2H), 6.86 (s, 1H), 6.51-6.41 (m, 1H), 6.34-6.17 (m, 3H), 5.71-5.60 (m, 1H), 5.12-5.07 (m, 2H), 4.96 (d, J=9.5 Hz, 1H), 4.70-4.63 (m, 1H), 4.60 (d, J=4.4 Hz, 1H), 4.14-4.03 (m, 1H), 4.02-3.90 (m, 2H), 3.76-3.65 (m, 1H), 3.54 (d, J=7.3 Hz, 1H), 3.31 (s, 3H), 3.25-3.17 (m, 1H), 3.17-3.15 (m, 1H), 3.14 (s, 3H), 2.85-2.75 (m, 2H), 2.43-2.37 (m, 3H), 2.34-2.24 (m, 1H), 2.21-2.12 (m, 2H), 2.11-1.97 (m, 2H), 1.93-1.87 (m, 1H), 1.81 (s, 3H), 1.78-1.68 (m, 4H), 1.65-1.44 (m, 11H), 1.41-1.36 (m, 1H), 1.35-1.24 (m, 5H), 1.18-1.09 (m, 3H), 1.01-0.97 (m, 4H), 0.96-0.92 (m, 1H), 0.90 (d, J=6.4 Hz, 3H), 0.87-0.79 (m, 7H), 0.73 (d, J=6.7 Hz, 3H), 0.56 (q, J=11.8 Hz, 1H).

Diastereomer 2: A solution of Compound 30 (60 mg, 0.060 mmol) in HCl (1.25M solution in methanol, 2.9 mL, 3.60 mmol) was stirred at room temperature for eight hours. The reaction was evaporated under reduced pressure to afford the crude product. The crude diastereomer was purified by preparative HPLC (method 2) to afford Compound 33 (3.6 mg, 6.3% yield) as a white solid.

Compound 33: ESIMS [M+H]+ 900.0, [M+FA−H]− 944.0

$^1$H NMR (400 MHz, DMSO-$d_6$) δ: 9.19 (d, J=150.7 Hz, 2H), 6.72 (s, 1H), 6.48 (dd, J=14.3, 11.1 Hz, 1H), 6.31-6.16 (m, 3H), 5.56 (dd, J=14.6, 9.5 Hz, 1H), 5.04 (d, J=5.0 Hz, 1H), 4.94 (dd, J=6.4, 1.9 Hz, 1H), 4.81 (d, J=9.8 Hz, 1H), 4.67-4.59 (m, 2H), 4.17-4.05 (m, 1H), 3.87 (dd, J=9.2, 4.9 Hz, 1H), 3.65-3.52 (m, 2H), 3.50-3.43 (m, 1H), 3.32 (s, 3H), 3.23 (d, J=9.2 Hz, 1H), 3.20-3.16 (m, 1H), 3.12 (s, 3H), 2.91-2.82 (m, 2H), 2.29 (s, 3H), 2.23-2.10 (m, 3H), 2.09-2.03 (m, 1H), 2.00-1.90 (m, 3H), 1.86 (s, 3H), 1.80-1.63 (m, 5H), 1.56-1.50 (m, 3H), 1.47 (s, 3H), 1.44-1.35 (m, 4H), 1.33-1.25 (m, 1H), 1.24-1.09 (m, 6H), 1.04-0.94 (m, 8H), 0.90-0.87 (m, 1H), 0.84 (d, J=6.5 Hz, 3H), 0.80 (d, J=6.7 Hz, 3H), 0.74 (d, J=6.7 Hz, 3H), 0.72-0.66 (m, 1H), 0.65-0.54 (m, 1H).

Example 19. Synthesis of Compound 34 and Compound 35

To a mixture of Intermediate 1 (150 mg, 0.167 mmol) and tert-butyl hydroxycarbamate (333 mg, 2.50 mmol) in DCM (5 mL) was added 4-methylbenzenesulfonic acid hydrate (9.51 mg, 0.0501 mmol). The reaction mixture was stirred at room temperature for three hours. The entire reaction mixture was directly purified by flash chromatography (silica; MeCN/DCM 0:100 to 100:0). The second eluting peak afforded a product mixture of both diastereomers.

The diastereomeric mixture was separated by SFC chromatography (method 1).

The first eluting diastereomer afforded Compound 34 (32.4 mg, 19.0% yield) as a white solid.

Compound 34: ESIMS [M+NH$_4$]+ 1019.1, [M+FA−H]− 1046.1

$^1$H NMR (400 MHz, DMSO-$d_6$) δ: 8.78 (s, 1H), 6.47-6.37 (m, 1H), 6.22-6.10 (m, 2H), 5.97 (s, 1H), 5.97-5.90 (m, 1H), 5.50-5.39 (m, 1H), 5.06 (d, J=4.7 Hz, 1H), 5.02-4.94 (m, 2H), 4.65-4.53 (m, 3H), 4.05-3.94 (m, 1H), 3.87-3.76 (m, 1H), 3.60 (d, J=6.5 Hz, 1H), 3.58-3.51 (m, 1H), 3.39-3.34 (m, 1H), 3.32 (s, 3H), 3.23-3.16 (m, 1H), 3.14 (s, 3H), 2.84 (ddd, J=11.2, 8.6, 4.3 Hz, 1H), 2.71-2.59 (m, 1H), 2.24-2.11 (m, 2H), 2.08-2.01 (m, 2H), 1.95-1.88 (m, 1H), 1.78-1.71 (m, 5H), 1.64-1.46 (m, 10H), 1.44-1.35 (m, 13H), 1.30-1.13 (m, 8H), 1.11-1.03 (m, 1H), 1.00-0.95 (m, 4H), 0.92-0.82 (m, 8H), 0.79 (d, J=6.8 Hz, 3H), 0.76 (d, J=6.7 Hz, 3H), 0.58 (q, J=11.9 Hz, 1H).

The second eluting diastereomer afforded Compound 35 (17 mg, 10.3% yield) as a white solid.

Compound 35: ESIMS [M+NH$_4$]+ 1019.1, [M+FA−H]− 1046.1

$^1$H NMR (400 MHz, DMSO-$d_6$) δ: 9.02 (s, 1H), 6.55 (s, 1H), 6.51-6.41 (m, 1H), 6.24-6.13 (m, 2H), 5.96-5.90 (m, 1H), 5.59-5.46 (m, 1H), 5.02 (d, J=4.7 Hz, 1H), 4.99-4.93 (m, 1H), 4.87-4.80 (m, 1H), 4.69-4.61 (m, 1H), 4.60 (d, J=4.5 Hz, 1H), 4.45-4.36 (m, 1H), 3.87 (dd, J=9.1, 4.4 Hz, 1H), 3.85-3.76 (m, 1H), 3.71-3.60 (m, 1H), 3.54-3.44 (m, 1H), 3.31 (s, 3H), 3.23 (d, J=9.2 Hz, 1H), 3.21-3.15 (m, 1H), 3.12 (s, 3H), 2.91-2.79 (m, 2H), 2.46-2.35 (m, 1H), 2.29-2.18 (m, 1H), 2.17-2.10 (m, 1H), 2.09-2.01 (m, 1H), 1.98-1.89 (m, 2H), 1.86 (s, 3H), 1.79-1.62 (m, 6H), 1.55-1.46 (m, 6H), 1.44-1.27 (m, 14H), 1.25-1.09 (m, 6H), 1.06-0.95 (m, 8H), 0.89-0.83 (m, 4H), 0.80 (d, J=6.8 Hz, 3H), 0.72 (d, J=6.7 Hz, 4H), 0.59 (q, J=11.8 Hz, 1H).

Example 20. Synthesis of Compound 36 and Compound 37

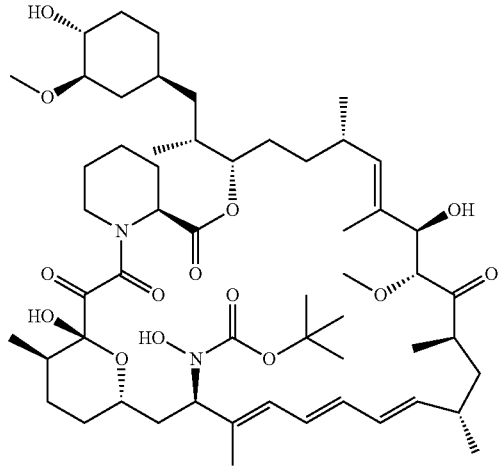

Compound 34

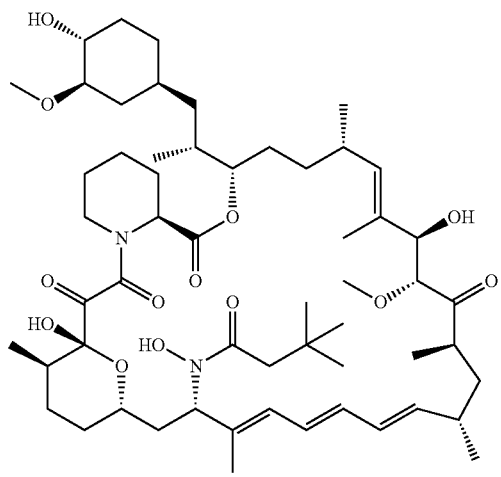

Compound 35

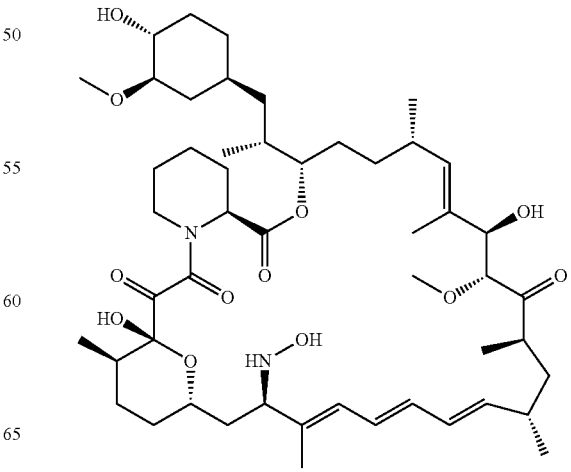

Compound 36

103
-continued

Compound 37

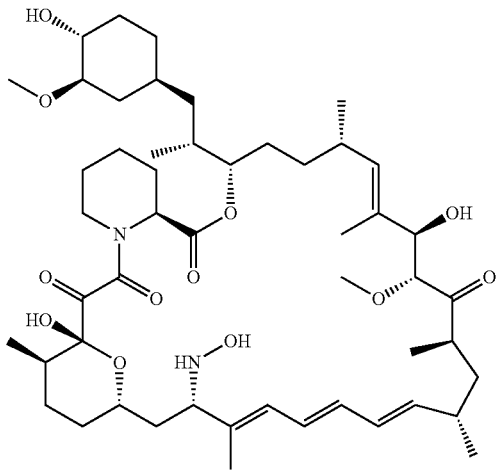

Diastereomer 1: A solution of Compound 34 (29.7 mg, 0.030 mmol) in HCl (4M solution in dioxane, 445 μL, 1.78 mmol) was stirred at room temperature for 13 minutes. The reaction was directly freeze dried to give the crude product. The crude diastereomer was purified by preparative HPLC (method 2) to afford Compound 36 (10.5 mg, 38.1% yield) as a white solid.

Compound 36: ESIMS [M+H]$^+$ 902.0, [M+FA−H]$^−$ 946.0

$^1$H NMR (400 MHz, DMSO-d6) δ: 6.81-6.74 (m, 1H), 6.54 (s, 1H), 6.48-6.39 (m, 1H), 6.17-6.08 (m, 2H), 5.96 (d, J=10.7 Hz, 1H), 5.49 (dd, J=14.1, 8.9 Hz, 1H), 5.05 (d, J=4.6 Hz, 1H), 5.03-4.98 (m, 2H), 4.71-4.63 (m, 1H), 4.60 (d, J=4.4 Hz, 1H), 4.02-3.93 (m, 2H), 3.66 (d, J=6.0 Hz, 1H), 3.63-3.53 (m, 1H), 3.40-3.35 (m, 1H), 3.31 (s, 3H), 3.25-3.19 (m, 1H), 3.16-3.12 (m, 4H), 2.86-2.80 (m, 1H), 2.66-2.56 (m, 1H), 2.27-2.15 (m, 2H), 2.12-2.07 (m, 1H), 2.06-1.98 (m, 1H), 1.95-1.88 (m, 1H), 1.84-1.78 (m, 4H), 1.74-1.69 (m, 2H), 1.64-1.60 (m, 2H), 1.59-1.56 (m, 2H), 1.55-1.51 (m, 5H), 1.48-1.45 (m, 2H), 1.41-1.37 (m, 1H), 1.37-1.27 (m, 4H), 1.25-1.22 (m, 1H), 1.21-1.14 (m, 4H), 1.07-1.02 (m, 1H), 1.00-0.96 (m, 4H), 0.89-0.85 (m, 5H), 0.83 (d, J=6.4 Hz, 3H), 0.79 (d, J=6.7 Hz, 3H), 0.75 (d, J=6.8 Hz, 3H), 0.56 (q, J=11.8 Hz, 1H).

Diastereomer 2: A solution of Compound 35 (15.7 mg, 0.0157 mmol) in HCl (4M solution in dioxane, 392 μL, 1.57 mmol) was stirred at room temperature for 13 minutes. The reaction was directly freeze dried to give the crude product. The crude diastereomer was purified by preparative HPLC (method 2) to afford Compound 37 (4.0 mg, 27.5% yield) as a white solid.

Compound 37: ESIMS [M+H]$^+$ 901.6, [M+FA−H]$^−$ 945.6

$^1$H NMR (400 MHz, DMSO-d6) δ: 7.05-6.89 (m, 1H), 6.48 (s, 1H), 6.46-6.39 (m, 1H), 6.18-6.10 (m, 2H), 5.89 (dd, J=11.1, 1.6 Hz, 1H), 5.45 (dd, J=14.0, 9.4 Hz, 1H), 5.04 (d, J=4.7 Hz, 1H), 4.97-4.90 (m, 1H), 4.90-4.83 (m, 1H), 4.66-4.58 (m, 2H), 4.00-3.93 (m, 1H), 3.91 (dd, J=8.9, 3.8 Hz, 1H), 3.63-3.54 (m, 1H), 3.48-3.39 (m, 1H), 3.36-3.26 (m, 5H), 3.20-3.16 (m, 1H), 3.12 (s, 3H), 2.88-2.80 (m, 2H), 2.26-2.19 (m, 1H), 2.17-2.10 (m, 1H), 2.07-2.00 (m, 1H), 1.97-1.85 (m, 3H), 1.80-1.72 (m, 5H), 1.70-1.61 (m, 4H), 1.54-1.47 (m, 6H), 1.43-1.27 (m, 5H), 1.23-1.11 (m, 6H), 1.03-0.94 (m, 8H), 0.88-0.83 (m, 4H), 0.79 (d, J=6.7 Hz, 4H), 0.72 (d, J=6.8 Hz, 3H), 0.60 (q, J=11.9 Hz, 1H).

104
Example 21. Synthesis of Compound 38 and Compound 39

Compound 38

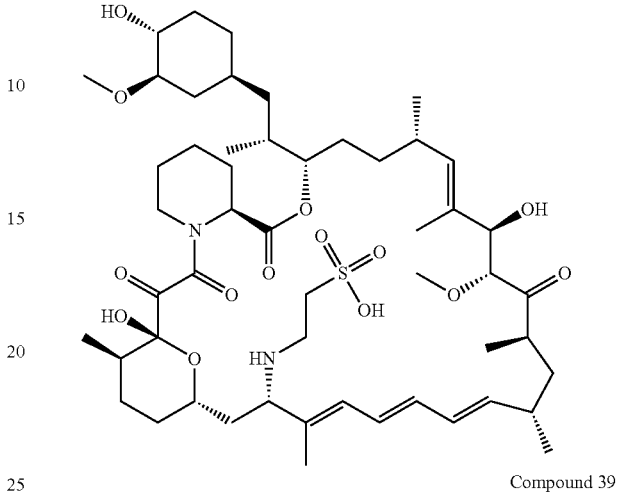

Compound 39

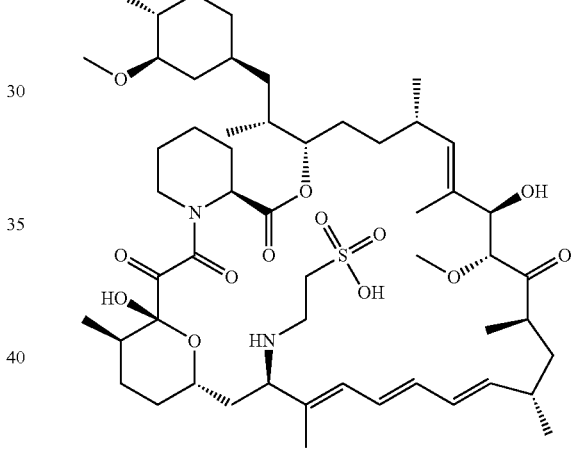

Diastereomer 1: To a solution of Intermediate 5 (15.4 mg, 0.0160 mmol) in DCM (1 mL) was added 4-methylbenzenesulfonic acid hydrate (3.0 mg, 0.016 mmol). The reaction mixture was stirred at room temperature for one hour. The entire reaction mixture was directly purified by preparative HPLC (method 2) to afford Compound 38 (11.3 mg, 70.6% yield) as a white solid.

Compound 38: ESIMS [M+H]$^+$ 994.0, [M−H]$^−$ 992.1

$^1$H NMR (400 MHz, DMSO-d6) δ: 8.88-8.30 (m, 2H), 6.71 (s, 1H), 6.49 (dd, J=14.6, 11.0 Hz, 1H), 6.35-6.24 (m, 2H), 6.20 (dd, J=14.8, 10.7 Hz, 1H), 5.57 (dd, J=14.8, 9.6 Hz, 1H), 5.04 (d, J=4.8 Hz, 1H), 4.96-4.91 (m, 1H), 4.81 (d, J=9.8 Hz, 1H), 4.66-4.61 (m, 1H), 4.60 (d, J=4.7 Hz, 1H), 4.08-3.98 (m, 1H), 3.91-3.85 (m, 1H), 3.85-3.75 (m, 1H), 3.68-3.57 (m, 1H), 3.50-3.42 (m, 1H), 3.32 (s, 3H), 3.23 (d, J=9.2 Hz, 1H), 3.21-3.15 (m, 1H), 3.12 (s, 3H), 3.06-2.91 (m, 2H), 2.89-2.74 (m, 4H), 2.25-2.08 (m, 3H), 2.08-1.98 (m, 2H), 1.98-1.89 (m, 2H), 1.84 (s, 3H), 1.78-1.62 (m, 5H), 1.55-1.45 (m, 6H), 1.44-1.28 (m, 5H), 1.24-1.08 (m, 6H), 1.04-0.93 (m, 8H), 0.89-0.82 (m, 4H), 0.80 (d, J=6.8 Hz, 3H), 0.75 (d, J=6.7 Hz, 3H), 0.69-0.54 (m, 2H).

Diastereomer 2: To a solution of Intermediate 6 (13.7 mg, 0.0141 mmol) in DCM (1 mL) was added 4-methylbenzenesulfonic acid hydrate (2.67 mg, 0.0141 mmol). The reaction mixture was stirred at room temperature for one hour. The entire reaction mixture was directly purified by preparative HPLC (method 2) to afford Compound 39 (9.1 mg, 63.9% yield) as a white solid.

Compound 39: ESIMS [M+H]$^+$ 993.9, [M–H]$^-$ 991.9

$^1$H NMR (400 MHz, DMSO-d$_6$) δ: 8.85-8.07 (m, 2H), 6.53-6.45 (m, 1H), 6.36 (d, J=10.9 Hz, 1H), 6.30-6.20 (m, 2H), 6.17 (s, 1H), 5.74 (dd, J=14.3, 8.1 Hz, 1H), 5.12-5.08 (m, 1H), 5.08-5.05 (m, 1H), 4.93 (d, J=9.5 Hz, 1H), 4.76-4.67 (m, 1H), 4.59 (d, J=4.4 Hz, 1H), 4.10-3.98 (m, 2H), 3.94 (dd, J=7.7, 5.0 Hz, 1H), 3.71-3.61 (m, 1H), 3.50 (d, J=7.7 Hz, 1H), 3.31 (s, 3H), 3.25-3.18 (m, 1H), 3.17-3.09 (m, 5H), 3.08-3.02 (m, 1H), 2.89-2.78 (m, 4H), 2.35-2.26 (m, 1H), 2.24-2.18 (m, 1H), 2.18-2.10 (m, 2H), 2.10-1.99 (m, 1H), 1.95-1.88 (m, 1H), 1.81 (s, 3H), 1.77-1.68 (m, 4H), 1.65-1.59 (m, 2H), 1.59-1.46 (m, 8H), 1.46-1.38 (m, 1H), 1.37-1.22 (m, 6H), 1.21-1.12 (m, 3H), 1.04-0.97 (m, 4H), 0.94-0.88 (m, 4H), 0.87-0.78 (m, 7H), 0.74 (d, J=6.7 Hz, 3H), 0.56 (q, J=11.9 Hz, 1H).

Example 22. Synthesis of Compound 40 and Compound 41

Compound 40

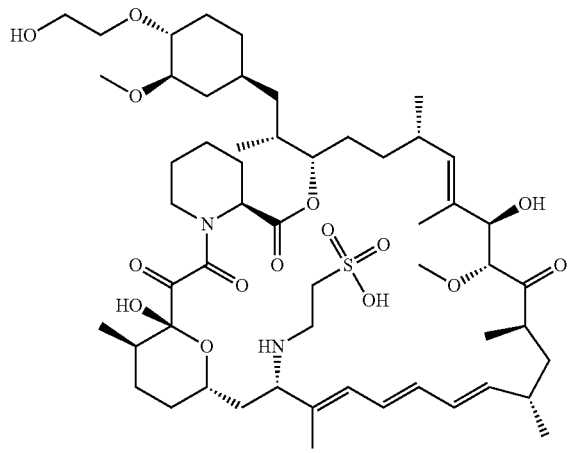

Compound 41

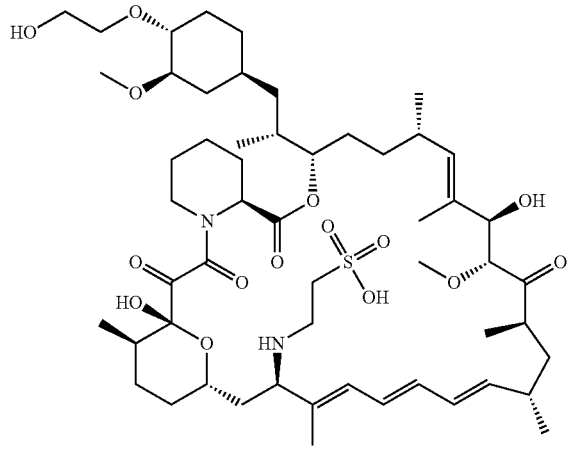

Diastereomer 1: To a solution of Intermediate 9 (20 mg, 0.018 mmol) in DCM (1 mL) was added 4-methylbenzenesulfonic acid hydrate (5.0 mg, 0.026 mmol). The reaction mixture was stirred at room temperature for one hour. The entire reaction mixture was directly purified by preparative HPLC (method 2) to afford Compound 40 (9.6 mg, 50.9% yield) as a white solid.

Compound 40: ESIMS [M+H]$^+$ 1038.1, [M–H]$^-$ 1036.1

$^1$H NMR (400 MHz, DMSO-d$_6$) δ: 8.85-8.39 (m, 2H), 6.71 (s, 1H), 6.53-6.43 (m, 1H), 6.37-6.24 (m, 2H), 6.23-6.14 (m, 1H), 5.57 (dd, J=15.0, 9.6 Hz, 1H), 5.03 (d, J=4.9 Hz, 1H), 4.97-4.90 (m, 1H), 4.81 (d, J=9.8 Hz, 1H), 4.67-4.54 (m, 1H), 4.45 (t, J=5.4 Hz, 1H), 4.10-3.97 (m, 1H), 3.92-3.78 (m, 2H), 3.68-3.57 (m, 1H), 3.54-3.42 (m, 5H), 3.32 (s, 3H), 3.23 (d, J=9.1 Hz, 1H), 3.12 (s, 3H), 3.10-3.01 (m, 2H), 3.01-2.93 (m, 2H), 2.90-2.83 (m, 1H), 2.83-2.71 (m, 2H), 2.25-2.07 (m, 3H), 2.06-2.01 (m, 1H), 1.99-1.90 (m, 3H), 1.83 (s, 3H), 1.74-1.62 (m, 4H), 1.58-1.50 (m, 3H), 1.47 (s, 3H), 1.45-1.26 (m, 6H), 1.26-1.06 (m, 6H), 1.07-0.95 (m, 8H), 0.94-0.90 (m, 1H), 0.84 (d, J=6.5 Hz, 3H), 0.80 (d, J=6.7 Hz, 3H), 0.75 (d, J=6.7 Hz, 3H), 0.70-0.56 (m, 2H).

Diastereomer 2: To a solution of Intermediate 10 (9 mg, 0.008 mmol) in DCM (0.5 mL) was added 4-methylbenzenesulfonic acid hydrate (2.3 mg, 0.012 mmol). The reaction mixture was stirred at room temperature for one hour. The entire reaction mixture was directly purified by preparative HPLC (method 2) to afford Compound 41 (3.0 mg, 35.3% yield) as a white solid.

Compound 41: ESIMS [M+H]$^+$ 1037.9, [M–H]$^-$ 1036.1

$^1$H NMR (400 MHz, DMSO-d$_6$) δ: 8.90-8.13 (m, 2H), 6.52-6.44 (m, 1H), 6.34 (d, J=11.0 Hz, 1H), 6.28-6.20 (m, 2H), 6.19 (s, 1H), 5.74 (dd, J=14.2, 7.9 Hz, 1H), 5.11-5.06 (m, 2H), 4.96-4.90 (m, 1H), 4.76-4.68 (m, 1H), 4.44 (t, J=5.4 Hz, 1H), 4.11-3.97 (m, 2H), 3.94 (dd, J=7.6, 4.9 Hz, 1H), 3.70-3.62 (m, 1H), 3.52-3.45 (m, 5H), 3.32 (s, 3H), 3.28-3.19 (m, 1H), 3.14 (s, 3H), 3.08-2.92 (m, 4H), 2.89-2.78 (m, 3H), 2.35-2.26 (m, 1H), 2.24-2.17 (m, 1H), 2.16-2.08 (m, 2H), 1.96-1.89 (m, 2H), 1.80 (s, 3H), 1.75-1.59 (m, 6H), 1.56-1.50 (m, 7H), 1.46-1.40 (m, 1H), 1.38-1.23 (m, 7H), 1.21-1.14 (m, 2H), 1.09-1.05 (m, 1H), 1.03-0.98 (m, 4H), 0.93-0.89 (m, 4H), 0.86-0.81 (m, 7H), 0.74 (d, J=6.7 Hz, 3H), 0.62 (q, J=11.7 Hz, 1H).

Example 23: Synthesis of Compound 42

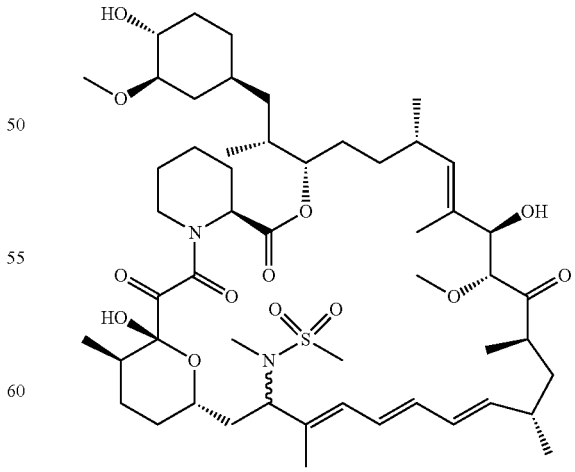

* Absolute C16 stereochemistry undetermined

Intermediate 1 (0.185 g, 0.206 mmol) was combined with N-methyl methanesulfonamide (0.188 ml, 2.06 mmol) in anhydrous dichloromethane (1.0 mL) in a reaction vial. The vial was capped and the mixture was twice vacuum purged with nitrogen. Trifluoroacetic acid (0.047 ml, 0.62 mmol) was added dropwise over a period of twenty seconds. The reaction was stirred at room temperature for 30 minutes.

The reaction was quenched with saturated aqueous NaHCO$_3$. The quenched mixture was extracted three times with EtOAc. The organic extracts were combined, dried over Na2SO4, decanted and concentrated.

The crude product was purified by silica gel flash column chromatography (0-50% acetone-heptane) to give Compound 42 (0.063 g, 0.061 mmol, 29.8% yield) as a light yellow solid.

Compound 42: ESIMS [M+NH$_4$]$^+$ 995.8, [M−H]$^−$ 976.0

HRMS: Calculated for C52H84N2O13SNa (sodium adduct) 999.5592. Found 999.5591

$^1$H NMR (600 MHz, Chloroform-d) δ 6.43 (dd, J=14.7, 10.9 Hz, 1H), 6.23 (dd, J=14.7, 10.6 Hz, 1H), 6.12 (dd, J=14.9, 10.7 Hz, 1H), 5.97 (d, J=10.9 Hz, 1H), 5.35 (dd, J=14.9, 9.8 Hz, 1H), 5.19 (d, J=5.9 Hz, 1H), 5.14 (d, J=9.9 Hz, 1H), 4.83 (d, J=12.2 Hz, 1H), 4.70-4.65 (m, 1H), 4.18 (d, J=5.7 Hz, 1H), 3.91 (t, J=11.2 Hz, 1H), 3.85 (t, J=8.1 Hz, 1H), 3.63 (d, J=13.9 Hz, 1H), 3.47-3.32 (m, 8H), 3.30 (s, 3H), 3.00 (s, 3H), 2.95-2.89 (m, 2H), 2.69-2.62 (m, 1H), 2.55 (s, 3H), 2.25 (m, 4H), 2.18-2.04 (m, 4H), 1.99 (dd, J=12.9, 4.3 Hz, 2H), 1.88-1.83 (m, 4H), 1.80-1.68 (m, 3H), 1.68-1.60 (m, 4H), 1.60-1.48 (m, 2H), 1.44-1.40 (m, 2H), 1.40-1.17 (m, 4H), 1.09-1.03 (m, 4H), 1.02-0.96 (m, 4H), 0.96-0.88 (m, 4H), 0.87-0.84 (m, 6H), 0.65 (q, J=12.0 Hz, 1H).

Determination of Absolute Configuration

The absolute configuration of the compounds at position C16 was assigned using the chemical shifts of hydrogen atoms H25 and H27, as well as the relative shifts Δf2 of hydrogen atom H6 from the respective HSQC NMR spectra. The spectra were recorded on a Bruker Spectrospin (400 MHz). DMSO-d6 was generally used as solvent. The relative chemical shifts of H25 and H27 were characteristic for the stereoisomers (R)-C16 and (S)-C16.

TABLE 2

| | |
|---|---|
| Chemical shift of (R)-C16 epimer at H16: | 2.5-2.9 ppm |
| Chemical shift of (S)-C16 epimer at H16: | 2.8-2.9 ppm |
| Chemical shift of (R)-C16 epimer at H27: | 3.5-3.8 ppm |
| Chemical shift of (S)-C16 epimer at H27: | 3.2-3.4 ppm |

The relative chemical shifts (Δf2) of the two C6 hydrogens are indicative for the absolute configuration of the C16 epimers.

TABLE 3

| | |
|---|---|
| Relative chemical shift Δf2 of H6 for (R)-C16 epimer: | 150.6-202.3 Hz |
| Relative chemical shift Δf2 of H6 for (S)-C16 epimer: | 54.5-80.9 Hz |

The X-ray structures of Compound 2 (absolute configuration (S)-C16) and Compound 29 (absolute configuration (R)-C16) served as references for the stereochemical assignments.

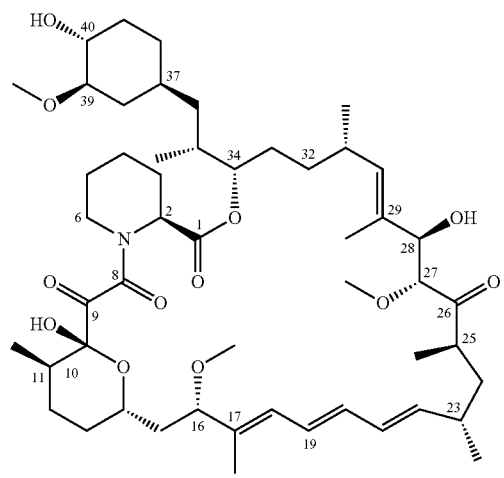 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C]

TABLE 4

| Compound | Absolute configuration at C16 | H25 [ppm] | H27 [ppm] | Δf2 H6 [Hz] |
|---|---|---|---|---|
| 1 | R | 2.5 | 3.7 | 180.3 |
| 2 | S | 2.9 | 3.2 | 75.3 |
| 3 | S | 2.9 | 3.2 | 77.8 |
| 4 | R | 2.5 | 3.8 | 187.6 |
| 5 | S | 2.9 | 3.2 | 76.9 |
| 6 | R | 2.5 | 3.8 | 202.3 |
| 7 | S | 2.9 | 3.2 | 80.1 |
| 8 | R | 2.5 | 3.8 | 199.3 |
| 9 | S | 2.8 | 3.2 | 77.7 |
| 10 | R | 2.5 | 3.8 | 200.8 |
| 11 | S | 2.9 | 3.2 | 73.2 |
| 12 | R | 2.6 | 3.7 | 177.3 |
| 13 | S | 2.9 | 3.2 | 74.4 |
| 14 | R | 2.5 | 3.8 | 199.7 |
| 15 | S | 2.9 | 3.2 | 80.9 |
| 16 | R | 2.5 | 3.8 | 208.5 |
| 17 | S | 2.8 | 3.2 | 67.5 |
| 18 | R | 2.5 | 3.8 | 187.2 |
| 19 | S | 2.9 | 3.2 | 75.4 |
| 20 | R | 2.5 | 3.7 | 189.4 |
| 21 | R | 2.6 | 3.7 | 157.9 |
| 22 | S | 2.8 | 3.2 | 72.1 |
| 23 | R | 2.6 | 3.7 | 186.8 |
| 24 | S | 2.8 | 3.2 | 72.5 |
| 25 | R | 2.5 | 3.7 | 180.2 |
| 26 | S | 2.9 | 3.2 | 72.6 |
| 27 | S | 2.8 | 3.4 | 55.4 |
| 4-A | S | 2.9 | 3.2 | 42.8 |
| 4-B | R | 2.6 | 3.7 | 178.2 |
| 28 | S | 2.8 | 3.3 | 51.4 |
| 29 | R | 2.7 | 3.6 | 158.5 |
| 30 | S | 2.9 | 3.3 | 0.0 |
| 31 | R | 2.7 | 3.6 | 62.6 |
| 32 | R | 2.8 | 3.5 | 201.2 |
| 33 | S | 2.9 | 3.2 | 54.5 |
| 34 | R | 2.6 | 3.6 | 78.5 |
| 35 | S | 2.9 | 3.2 | 67.9 |
| 36 | R | 2.6 | 3.7 | 150.6 |
| 37 | S | 2.8 | 3.3 | 59.6 |
| 38 | S | 2.9 | 3.2 | 64.5 |
| 39 | R | 2.9 | 3.5 | 173.8 |
| 40 | S | 2.9 | 3.2 | 61.2 |
| 41 | R | 2.9 | 3.5 | 172.7 |

Example 24: Biological Assays and Data

The activity of a compound according to the disclosure was assessed by the following in vitro & in vivo methods.

Pharmacological Characterization
Materials and Methods
Cell-Based Assay for Rapalog Potency Determination.

Rapalog potency was determined using MEF TSC1-/- cell based assay. MEF TSC1-/- cells are Mouse Embryonic Fibroblasts deficient in Tuberous sclerosis protein—TSC1, which negatively regulates mTORc1 signaling and thus display constitutive mTORc1 activation, resulting in phosphorylation (activation) of downstream molecules. This cell-based assay is used to measure inhibition (de-phosphorylation) of S6 and 4EBP1 by rapalogs or other mTOR inhibitors.

MEF TSC1-/- cells were plated on Poly-D-lysine coated 384 well Griener clear bottom plates and incubated overnight at 37° C., 5% $CO_2$. On the following day, cells were washed 8 times with "Hard starve" solution (1 L DPBS+1 g D-(+) glucose+10 ml of 7.5% Sodium Bicarbonate+20 ml of 1M HEPES) and incubated for further 2 hours in the same solution. Cells were next treated with compounds with decreasing concentrations (8 points at 3.16 fold dilutions) and incubated for 2 hours at 37° C., 5% $CO_2$. Cells were fixed with 4% paraformaldehyde for 30 min and washed 5 times with TBS-EDTA followed by immuno-staining with fluorescent tag labeled antibodies for pS6 (Ser240/244) (Cell Signaling #9468) and p4EBP1 (Thr 37/46) (Cell Signaling #5123). Nuclei were visualized with Hoechst (ThermoFisher Scientific #H3570) staining. Cells were imaged (InCell 600) using respective fluorescence channels and the potency of mTOR inhibitors was defined by pS6 $IC_{50}$ (nM).

Animal Maintenance, Treatment with Compounds and Tissue Collection.

All procedures involving animals were approved by the Institutional Animal Care and Use Committee of the Novartis Institutes for Biomedical Research, Cambridge, Mass., USA. Adult Sprague Dawley (SD) male rats were purchased from Envigo (Indianapolis, USA). Once imported, rats were maintained at the specific pathogen free facilities with controlled temperature and light (22° C., 12-h light/12-h dark cycle: lights on at 0600 h/lights off at 1800 h) and with ad libitum access to food and water. Rats were acclimated for at least 3 days before experiments commenced.

Compound 2 and RAD001 were formulated for oral (per os, p.o.) dosing. Blank formulations (without Compound 2 or RAD001) served as vehicle controls. Rats received a single dose of Compound 2, RAD001 or a respective vehicle p.o. At pre-determined times following treatment, rats were anesthetized with 3.5% isoflurane and euthanized. Various organs were collected and frozen in liquid nitrogen. Blood was collected via a tail vein or a cardiac puncture (terminal) and frozen for further pharmacokinetics analyses. All tissues were stored at −80° C. until analyzed.

Determination of Compound 2 and RAD001 Concentrations in Blood.

Concentrations were determined using HPLC/Mass spectrometry.

Protein Extraction and Immunoblotting.

For protein extraction, snap frozen tissues were lysed in MSD Lysis Buffer (MSD, Rockville, Md.), supplemented with complete EDTA free protease inhibitor and PhosSTOP phosphatase inhibitor tablets (Roche, Manheim, Germany), and centrifuged at 13,000 g for 20 min at 4° C. The resultant supernatant was used for immunoblotting. Protein was quantified with BCA protein assay (Thermo Scientific, MA). Samples were resolved on 4-20% Criterion™ TGX™ Pre-cast Midi Protein gels (Bio-Rad, CA) and transferred onto nitrocellulose membranes (Bio-Rad, CA) using a Trans Turbo Blot system (Bio-Rad, CA). Immunoblotting was performed with antibodies to p-S6 and t-S6 from Cell Signaling Technologies (all 1:1000 in TBS-T with 5% BSA). The 'p' and 't' prefixes signify 'phosphorylated' and 'total' forms respectively. Glyceraldehyde 3-phosphate dehydrogenase (GAPDH) detected with an anti-GAPDH antibody (#5174, Cell Signaling Technologies, MA) was used as a protein loading control. HRP-conjugated secondary antibodies against rabbit (#7074) were from Cell Signaling Technologies, MA. The chemiluminescence signal was generated using SuperSignal™ West Femto Enhanced Chemiluminescent Substrate (#34095, Thermo Scientific, MA) or Western Lightning® Plus-ECL Enhanced Chemiluminescence Substrate (NEL103001EA, Perkin Elmer, MA) and was captured using the ChemiDoc MP Imaging System (Bio-Rad). Resultant digital images were converted into a TIFF format and quantified using ImageJ software.

Generation of FKBP Knock-Out Cells.

A CRISPR/Cas9 system was used to deliver ribonucleoprotein complexes containing guide RNA (gRNA) sequences that target FKBP12

(GCCACTACTCACCGTCTCCT, location 1392950), FKBP12.6

(TGCCCCAAGCTCATCTAGCA, location 24063057), FKBP13

(GCAGATCGGGGTCAAGAAGC, location 64242479), FKBP25

(GGTTATAGGCTGTAACCAAG, location 45130715), FKBP52

(AAGACTCGGTCCCCAATCAT, location 2797173) and FKBP51

(TCATCAAGGCATGGGACATT, location 35620248) into 293T cells, using the Amaxa® 4D-Nucleofector™ X Kit (Lonza, V4XC-2032). Cell clones were screened by immunoblotting with anti-FKBP-specific antibodies: FKBP12 (Novus, NB300-508), FKBP12.6 (Abnova, H00002281-M01), FKBP13 (R&D Systems, MAB4356), FKBP25 (R&D Systems, MAB3955), FKBP52 (Cell signaling Technology, #11826) and FKBP51 (Cell signaling Technology, #12210). Single cell clones that were deficient for each FKBP were selected. Quintuple FKBP12/12.6/13/52/51 knock-out and FKBP12/12.6/25/52/51 knock-out cells were generated by sequentially knocking out five FKBP genes.

Treatment of Wild-Type (WT) and FKBP Knock-Out 293T Cells with RAD001 and Compound 2.

WT, FKBP12 knock-out, FKBP12/12.6/13/52/51 knock-out or FKBP12/12.6/25/52/51 knock-out 293T cells were plated at a density of 30,000 cells per well in poly-D-Lysine coated 96-well plates (Corning, #354461) in Dulbecco's modified Eagle's medium (ThermoFisher, #11995-065) supplemented with 10% fetal bovine serum (ThermoFisher, #16140-071). Cells were incubated at 37° C., 5% $CO_2$ for 48 hours until they reached ~80% confluence. Cells were treated with RAD001 or Compound 2 using either a 12-point or a 10-point dose range from 1000 nM to 0.0033 nM for 2 hours at 37° C. in triplicate. Media supplemented with blank Dimethyl sulfoxide (DMSO) was used as a control for both compounds. Phosphorylated amounts of S6K1 (Thr389) were detected by a sandwich ELISA kit (Cell signaling, #7063C) following the manufacture's protocol.

SPR Assay to Determine Binding Affinity to FK506-Binding Proteins (FKBP).

N-terminal avi-his6-tagged FKBP fusion proteins were expressed in E. coli and purified with nickel chromatography using standard procedures. Biotinylated his-avi-FKBPs were immobilized on a streptavidin chip using a Biacore 8K (GE Healthcare). To determine the kinetics-affinity of the rapalogs for FKBPs, rapalogs were diluted in DMSO to 50× working concentration. Next, 3.1 uLs of each rapalog solution was added to 150 uLs of buffer (50 mM Tris pH 7.5/150 mM NaCl/0.01% Tween 20/1 mM DTT) in a 384 deep well plate (greiner bio-one/78127) and mixed using a Biomek FX. The rapalog solution gradients (6 concentrations/2 fold dilutions, 3.1-100 nM or 31-1000 nM or 310-10000 nM) were then injected at 45 uL/min for 120 seconds: contact time and dissociation time was 1800 seconds in running buffer (50 mM Tris pH 7.5/150 mM NaCl/0.01% Tween 20/1 mM DTT/2% DMSO). The single-cycle kinetics data were fit to a 1:1 binding model to measure the association rate ka (1/Ms), the dissociation rate kd (1/s) and the affinity $K_D$ (M). To determine the apparent kinetics-affinity for ternary complex formation for rapalogs bound to FKBPs with mTOR, rapalogs were diluted in DMSO such that final concentration in DMSO was 500 μM. his$^6$-mTOR (amino acids 2019-2112) was diluted in buffer (50 mM Tris pH 7.5/150 mM NaCL/0.01% Tween 20/1 mM DTT) to prepare concentration gradient (6 concentrations/2 fold dilutions, 15.6-500 nM). 3.1 uLs of the 500 μM rapalog solutions were added to 150 uLs of the mTOR samples in a 384 deep well plate (greiner bio-one/78127) and mixed using a Biomek FX. The mTOR solution gradients were then injected at 45 uL/min for 120 seconds: contact time and dissociation time was 1800 seconds in running buffer (50 mM Tris pH 7.5/150 mM NaCl/0.01% Tween 20/1 mM DTT/2% DMSO). The single-cycle kinetics data was fit to a 1:1 binding model to measure the association rate ka (1/Ms), the dissociation rate kd (1/s) and the apparent affinity $K_D$ (M) for ternary complex formation. See Tables 6 and 7 below.

Differential pharmacology of rapalogs may be achieved in different cell or tissue types depending on 1) the relative abundance of FKBP homologs in these cells/tissues and 2) the specificity of binding to these different FKBP homologs (Mol. Cell Biol. (2013) 33:1357-1367).

Results

In vitro potency of mTOR inhibitors was defined by pS6 $IC_{50}$ (nM) in MEF TSC1-/- cells.

TABLE 5

| Compound | $IC_{50}$ (nM) |
|---|---|
| 1 | 0.55 |
| 2 | 0.11 |
| 3 | 0.26 |
| 4 | 1.2 |
| 5 | 1.8 |
| 6 | 13 |
| 7 | 2.4 |
| 8 | 4.5 |
| 9 | 2.7 |
| 10 | 12 |
| 11 | 0.94 |
| 12 | 1.1 |
| 13 | 5.3 |
| 14 | 7.2 |
| 15 | 3.6 |
| 16 | 50 |
| 17 | 1.6 |
| 18 | 6.6 |
| 19 | 0.34 |
| 20 | 1.7 |
| 21 | 2.1 |
| 22 | 0.11 |
| 23 | 26 |
| 24 | 0.52 |
| 25 | 1.8 |
| 26 | 0.086 |
| 27 | 1.9 |
| 28 | 0.35 |
| 29 | 30 |

TABLE 5-continued

| Compound | $IC_{50}$ (nM) |
|---|---|
| 30 | NA |
| 31 | NA |
| 32 | 18 |
| 33 | 0.67 |
| 34 | 27 |
| 35 | 4.4 |
| 36 | 1.6 |
| 37 | 0.21 |
| 38 | >500 |
| 39 | >500 |
| 40 | 160 |
| 41 | 33 |
| 42 | 0.300 |
| Intermediate 8 | 0.180 |

IC50 values are calculated as the average from multiple assays.

The equilibrium dissociation constants ($K_D$) to FKBP12, FKBP51, and FKBP52 are shown below in Table 6.

TABLE 6

| Compound | FKBP12 $K_D$ nM | FKBP51 $K_D$ nM | FKBP52 $K_D$ nM |
|---|---|---|---|
| RAD001 | 500 | 811 | 1766 |
| 1 | 0.061 | 11 | 9.8 |
| 2 | 4.8 | 144 | 374 |
| 3 | 0.20 | 40 | 61 |
| 4 | 0.55 | 315 | 256 |
| 11 | 0.29 | 45 | 63 |
| 12 | 0.39 | 117 | 135 |
| 18 | 0.73 | 573 | 436 |
| 24 | 0.54 | 25 | 90 |
| 26 | 0.83 | 47 | 80 |
| 42 | 6.5 | 1231 | 1383 |

Apparent affinity $K_D$ (M) for ternary complex formation is shown below in Table 7.

TABLE 7

| Compound | FKBP12 $K_D$ nM | FKBP12.6 $K_D$ nM | FKBP13 $K_D$ nM | FKBP25 $K_D$ nM | FKBP51 $K_D$ nM | FKBP52 $K_D$ nM |
|---|---|---|---|---|---|---|
| RAD001 | 21 | 47 | 21 | 75 | 348 | 253 |
| 2 | 25 | 55 | 127 | 2 | 52 | 36 |

Pharmacokinetic Profile of Compound 2 in Rats.

Figure 3A:
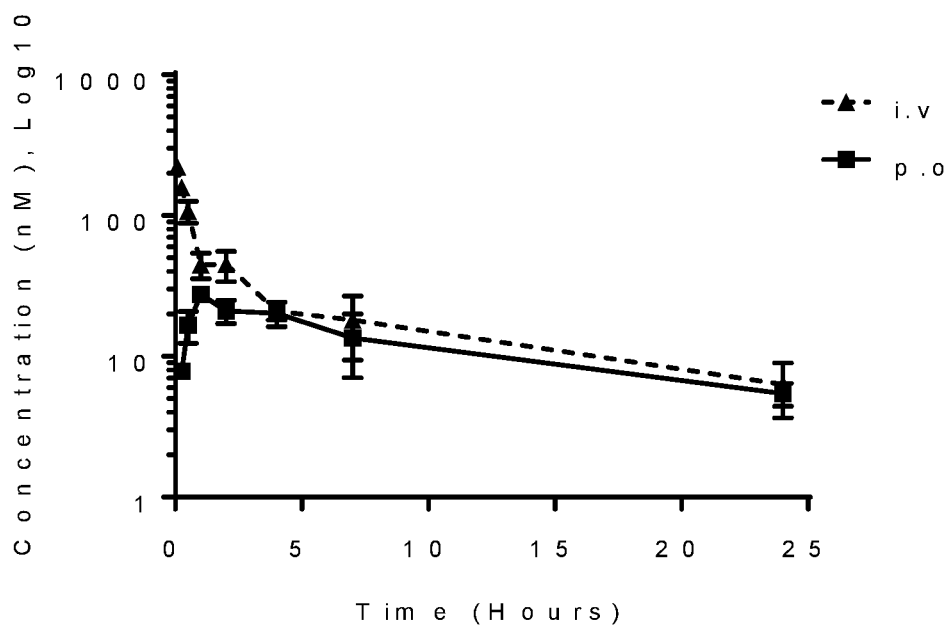
FIG. 3A depicts a line graph showing blood concentration of RAD001 in rats following intravenous (i.v.) and oral (p.o) dosing. Y axis—blood concentrations of RAD001 (nM). X axis—time (hours) for blood collection following RAD001 administration. Data are mean±standard deviation from 3 rats.
Figure 3B:
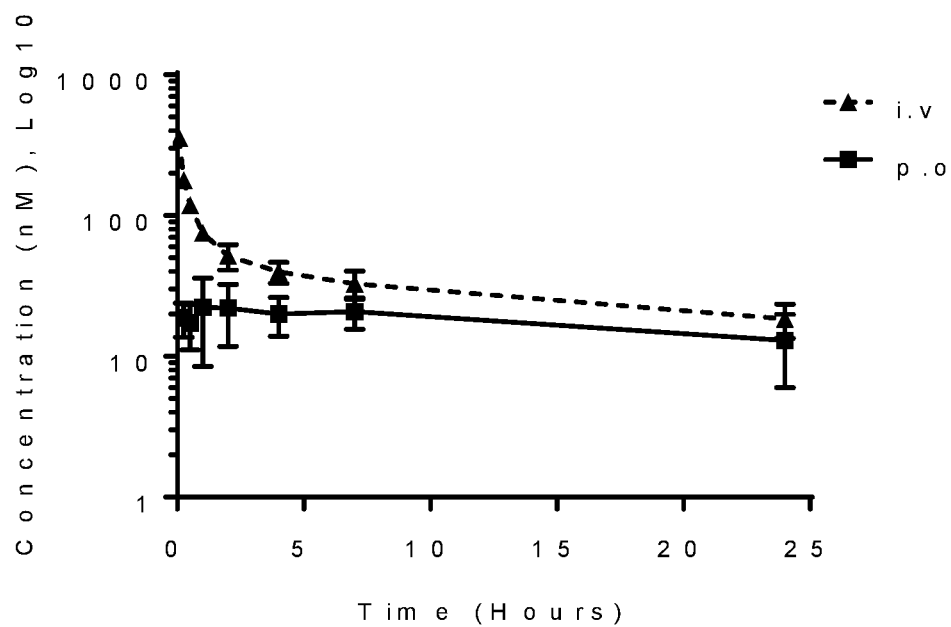
FIG. 3B depicts a line graph showing blood concentration of Compound 2 in rats following intravenous (i.v.) and oral (p.o.) dosing. Y axis—blood concentrations of Compound 2 (nM). X axis—time (hours) for blood collection following Compound 2 administration. Data are mean±standard deviation from 3 rats.

To compare bioavailability of Compound 2 versus RAD001 in the rat, compounds were formulated as solution formulations: Compound 2 was formulated in 15% PEG300, 7.5% Solutol, 7.5% Cremophore EL in MilliQ Water and RAD001 was formulated in 10% PEG300, 10% Solutol HS15, 10% Cremophore EL in PBS. Compounds were administered to rats aged 7-9 weeks (N=3 per group) p.o. at 3 mg/kg and intravenously (i.v). at 1 mg/kg (FIGS. 3A and 3B). For Compound 2 and RAD001 respectively, bioavailability was 16% and 19%, iv. terminal half-life 19 h and 9.5 h, clearance 13 mL/min/kg and 32 mL/min/kg.

113

Compound 2 Inhibits mTORc1 Pathway in the Rat Liver.

Figure 4A:
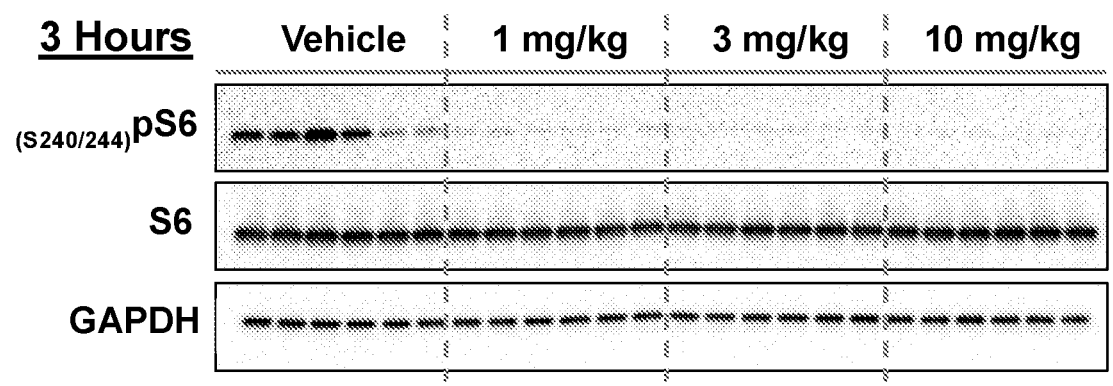
FIGS. 4A and 4B show that Compound 2 inhibits the mTORc1 pathway in rat liver. Rats were given a single oral dose of Compound 2 at 1, 3 or 10 mg/kg, and liver samples were collected at 3 hours following dosing. Rats treated with a vehicle were used as a control.
Figure 4B:
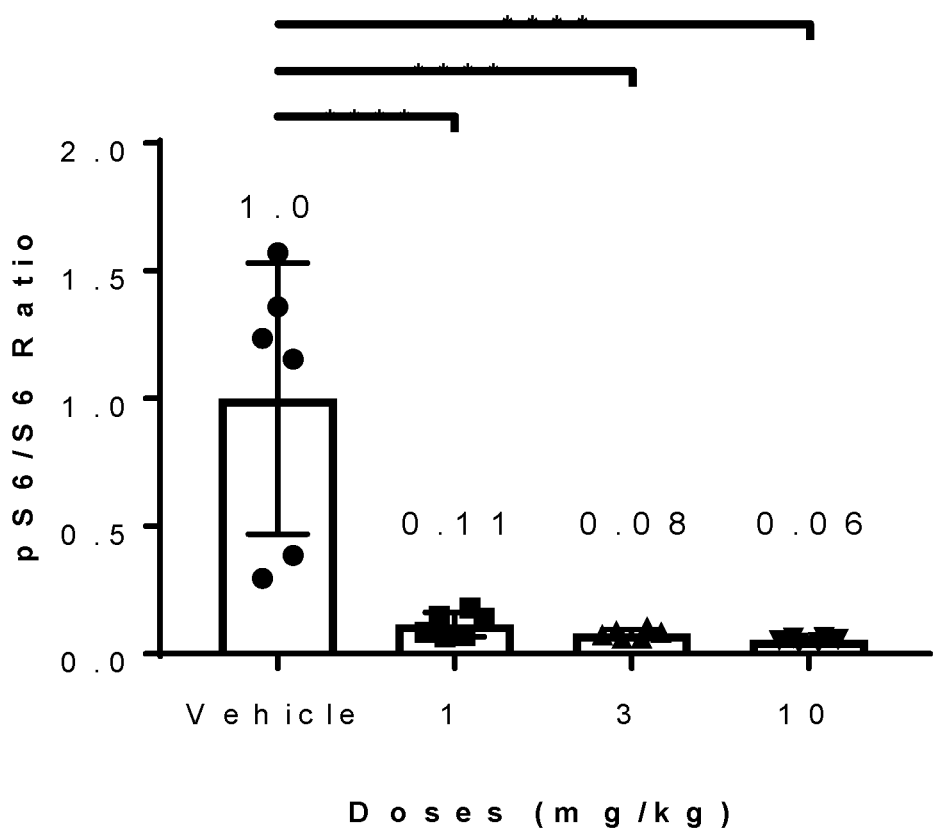

The ability of Compound 2 to inhibit mTORC1 pathway in vivo was determined in rats aged 4-6 months (FIGS. 4A and 4B). A single dose of Compound 2 at 1, 3 and 10 mg/kg (formulated as a custom made micro-emulsion preconcentrate, see e.g., Shavlakadze et al. J Gerontol A Biol Sci Med Sci. 73(7): 845-852, 2018) resulted in a significant de-phosphorylation (inactivation) of S6 in rat livers (compared with the vehicle control) (FIGS. 4A and 4B).

The Inhibitory Effect of Compound 2 is Less Dependent on FKBP12, Compared with RAD001.

Figure 5A:
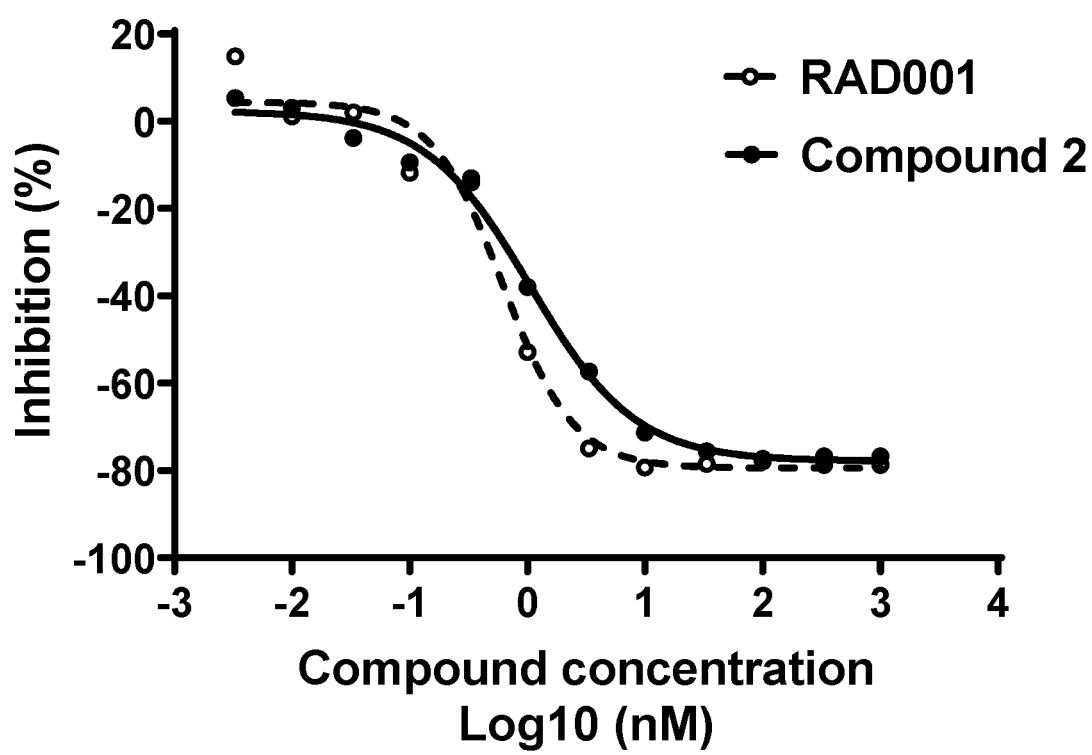
FIGS. 5A-5D depict line graphs showing inhibition of S6K1(Thr389) in wild-type (FIG. 5A), FKBP12 knock-out (FIG. 5B), FKBP12/12.6/13/52/51 knock-out (FIG. 5C) and FKBP12/12.6/25/52/51 knock-out (FIG. 5D) 293T cells, following treatment with Compound 2 (solid line) or RAD001 (dotted line). Cells were treated in triplicate. The Y axis represents percent inhibition relative to the S6K1 (Thr389) level in cells treated with media plus DMSO. The X axis represents concentrations for Compound 2 or RAD001.
Figure 5B:
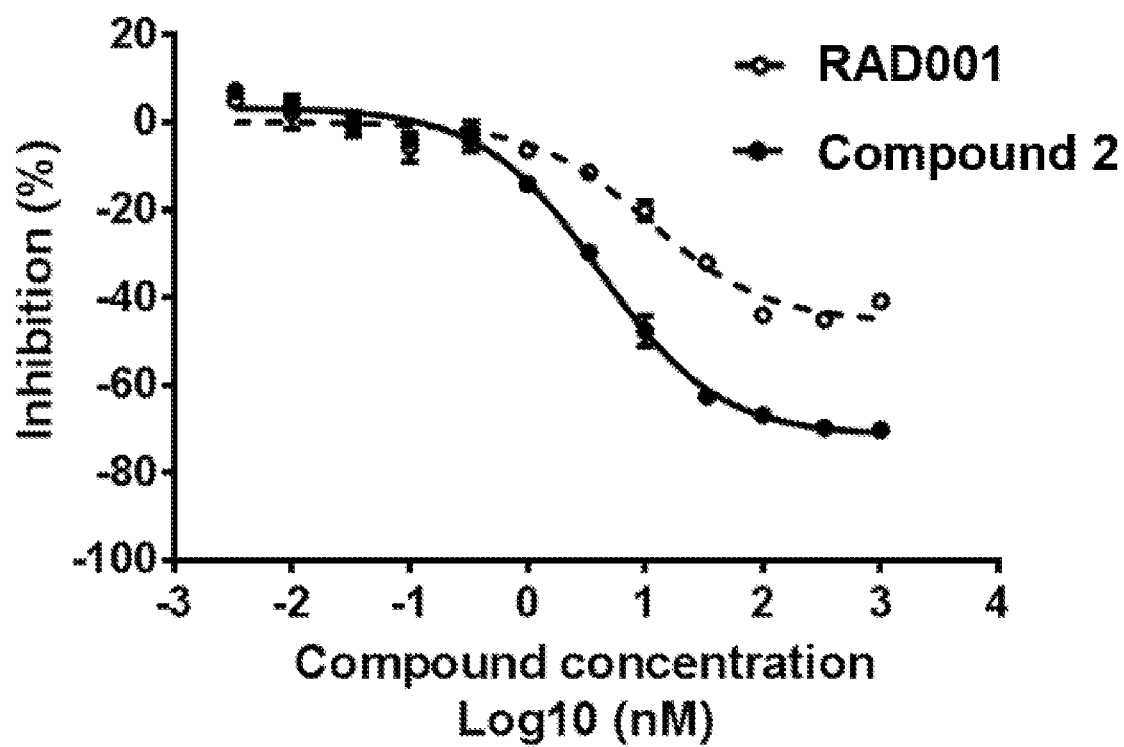

Initially, phosphorylated amounts of S6K1 (Thr389) were measured in WT and FKBP12 knock-out 293T cells, treated with Compound 2 or RAD001 (FIGS. 5A and 5B). S6K1 is a downstream target of mTORC1 and phosphorylation of its rapalog-sensitive Thir389 site is used as a functional readout of mTORC1 activity (Lee, C. H., Inoki, K. and Guan, K. L. (2007). mTOR pathway as a target in tissue hypertrophy. Annu. Rev. Pharmacol. Toxicol. 47, 443-467). In WT 293T cells, both RAD001 and Compound 2 were efficacious at achieving ~80% inhibition of S6K1(Thr389) phosphorylation (FIG. 5A). In the absence of FKBP12, ~70% de-phosphorylation of S6K1(Thr389) was still achieved with Compound 2, while only ~40% de-phosphorylation of S6K1 (Thr389) was achieved with RAD001 (FIG. 5B). These results indicate that in the absence of FKBP12, other FKBP homolog(s) may be responsible for the efficacy of Compound 2.

Figure 5C:
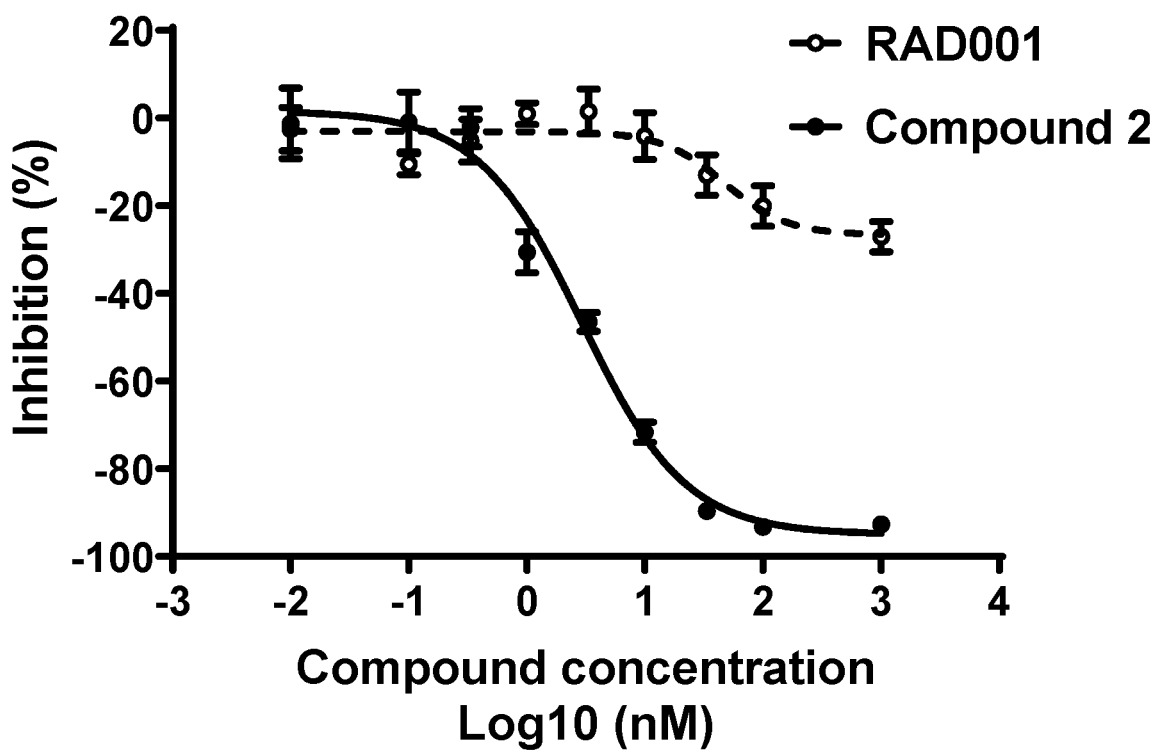

Next, the inhibitory effect (potency) of Compound 2 and RAD001 was assessed in 293T cells that lack five FKBPs: FKBP12/12.6/13/52/51 by measuring phosphorylated amounts of S6K1 (Thr389) (FIG. 5C). In these cells, RAD001 lost almost all it potency, while Compound 2 was efficacious in inhibiting S6K1 (Thr389) (FIG. 5C): at the highest tested concentration, Compound 2 inhibited S6K1 (Thr389) by ~90% (FIG. 5C). This result indicates that in the absence of FKBP12/12.6/13/52/51, pharmacological effect of Compound 2 may be mediated by another FKBP homolog.

Figure 5D:
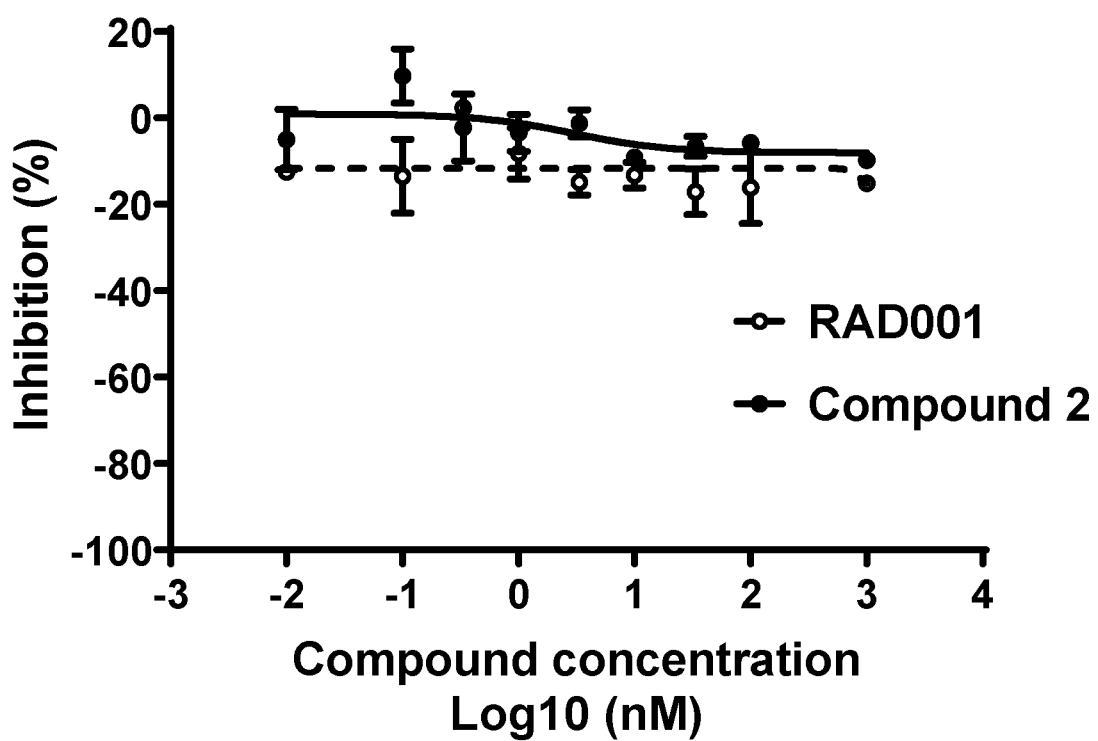

In order to identify an FKBP homolog responsible for the inhibitory effect of Compound 2 in the absence of FKBP12/12.6/13/51/52, potency of Compound 2 and RAD001 was assessed in 293T cells that lack FKBP12/12.6/25/52/51 by measuring phosphorylated amounts of S6K1 (Thr389) (FIG. 5D). In these cells, neither RAD001 nor Compound 2 were efficacious in inhibiting S6K1 (Thr389) (FIG. 5D). This result indicates that FKBP25 is sufficient for mediating the inhibitory effect of Compound 2, in the absence of other FKBP (FKBP 12/12.6/13/51/52) homologs.

Without wishing to be bound by theory, in the absence of FKBP12, other FKBPs may potentiate the inhibitory effect of Compound 2. Thus, Compound 2 may target a wider range of cell types as compared with RAD001, including cell types with low levels of FKBP12 expression and sufficient levels of other FKBPs.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

114

We claim:

1. A compound of Formula (I) or a pharmaceutically acceptable salt thereof, wherein:

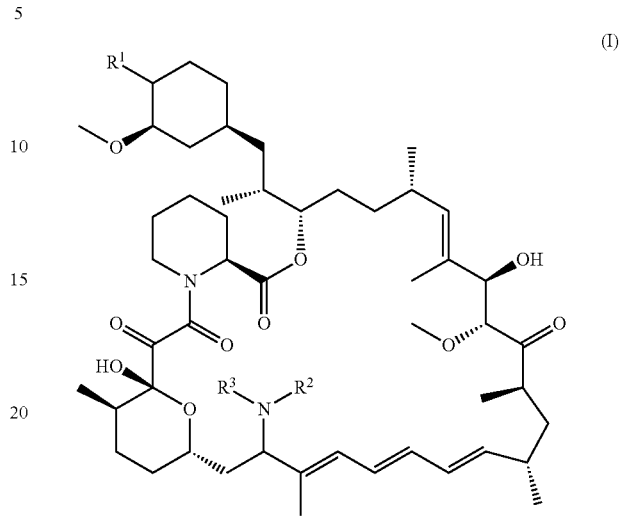

(I)

R$^1$ is selected from the group consisting of —OR$^a$ and a 5-6 membered heteroaryl;

R$^2$ and R$^3$ are each independently selected from the group consisting of H, C$_{1-6}$alkyl, —OR$^b$, —C$_{0-6}$alkylene-SO$_2$R$^4$, and —C(O)OR$^5$, R$^4$ is —OR$^5$, C$_{1-6}$alkyl, C$_{1-6}$haloalkyl, heteroC$_{1-6}$alkyl, C$_{1-6}$hydroxyalkyl, C$_{3-8}$ gscycloalkyl C$_{0-6}$alkyl;

R$^5$ is H or C$_{1-6}$alkyl;

R$^a$ is selected from the group consisting of H, —P(O)(R$^b$)$_2$, —C(O)R$^C$, —C(O)OR$^C$, C$_{1-6}$alkyl, and C$_{1-6}$hydroxyalkyl;

each R$^b$ is independently selected from the group consisting of H and C$_{1-6}$alkyl; and each R$^c$ is independently selected from the group consisting of H, C$_{1-6}$alkyl, and C$_{1-6}$hydroxyalkyl.

2. The compound of claim 1 or a pharmaceutically acceptable salt thereof, wherein R$^1$ is —OR$^a$.

3. The compound of claim 1 or a pharmaceutically acceptable salt thereof, wherein R$^1$ is 5-6 membered heteroaryl.

4. The compound of claim 1 or a pharmaceutically acceptable salt thereof, wherein R$^1$ is selected from the group consisting of hydroxyl,

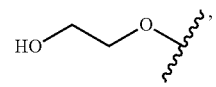

and a 5-membered heteroaryl.

5. The compound of claim 1 or a pharmaceutically acceptable salt thereof, wherein R$^2$ and R$^3$ are each independently selected from the group consisting of H and —OR$^b$.

6. The compound of claim 1 or a pharmaceutically acceptable salt thereof, wherein R$^2$ and R$^3$ are each independently selected from the group consisting of H, C$_{1-6}$alkyl, and —C$_{0-6}$alkylene-SO$_2$R$^4$.

7. The compound of claim 1 or a pharmaceutically acceptable salt thereof, wherein R$^2$ and R$^3$ are each independently selected from the group consisting of H, hydroxyl, —C$_{0-6}$alkylene-SO$_2$R$^4$, and —C(O)OR$^5$.

8. The compound of claim 1 or a pharmaceutically acceptable salt thereof, wherein:

R$^1$ is selected from the group consisting of hydroxy,

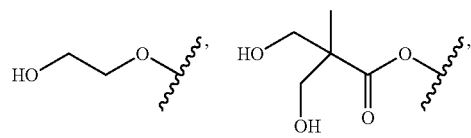

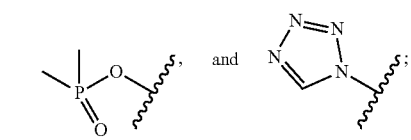

R$^2$ and R$^3$ are each independently selected from the group consisting of H, C$_{1-6}$alkyl, —OR$^b$, —C$_{0-6}$alkylene-SO$_2$R$^4$, and —C(O)OR$^5$;

R$^4$ is —OR$^5$, C$_{1-6}$alkyl, C$_{1-6}$haloalkyl, heteroC$_{1-6}$alkyl, C$_{1-6}$hydroxyalkyl, and C$_{3-8}$cycloalkylC$_{0-6}$alkyl; and R$^5$ is H or C$_{1-6}$alkyl.

9. The compound of claim 1 or a pharmaceutically acceptable salt thereof having structural Formula (I)-A or (1)-B:

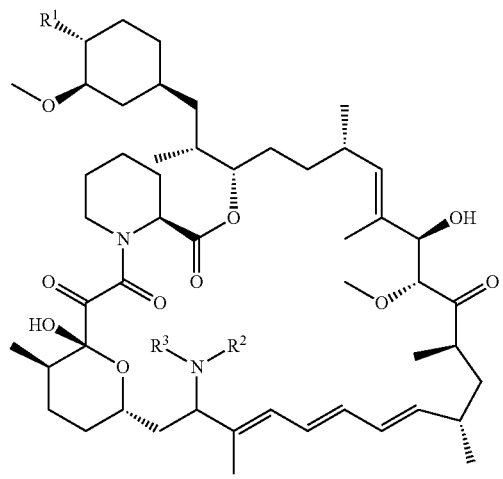

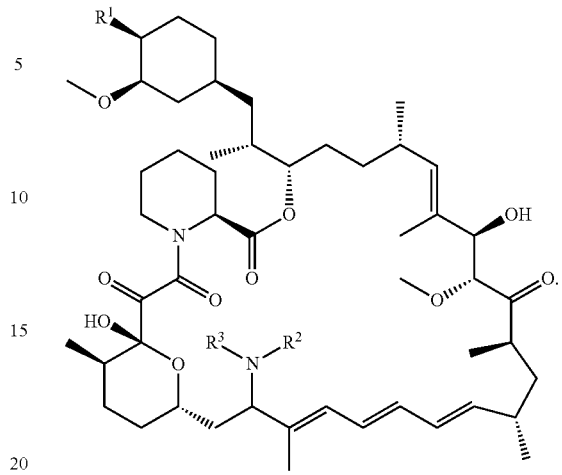

10. The compound of claim 1 or a pharmaceutically acceptable salt thereof having structural Formula (I)-C or (I)-D:

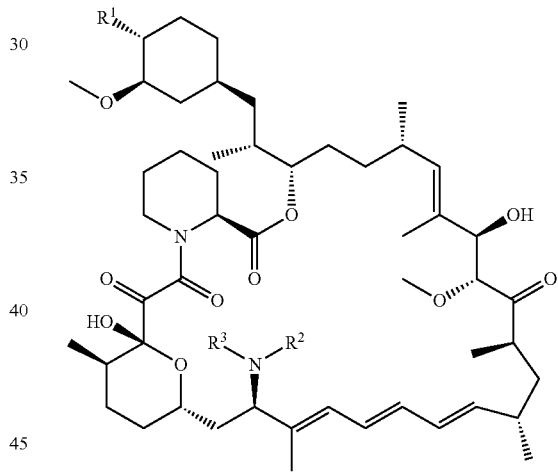

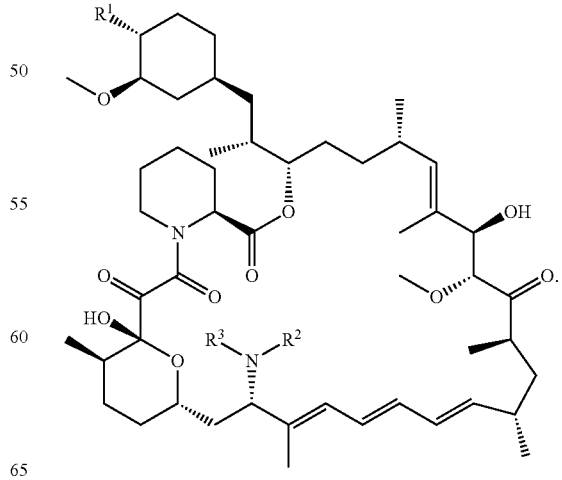

11. The compound of claim 1 or a pharmaceutically acceptable salt thereof having structural Formula (I)-E or (I)-F:
(I)-E
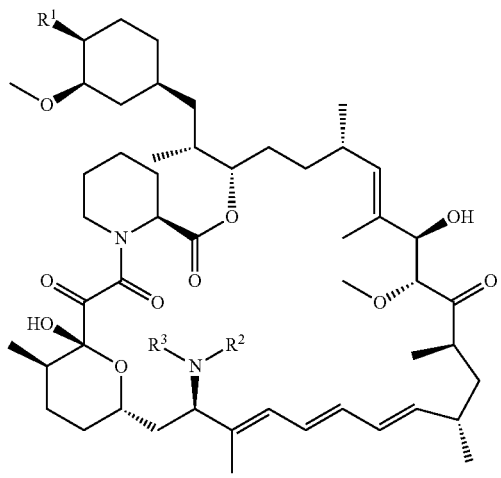
(I)-F
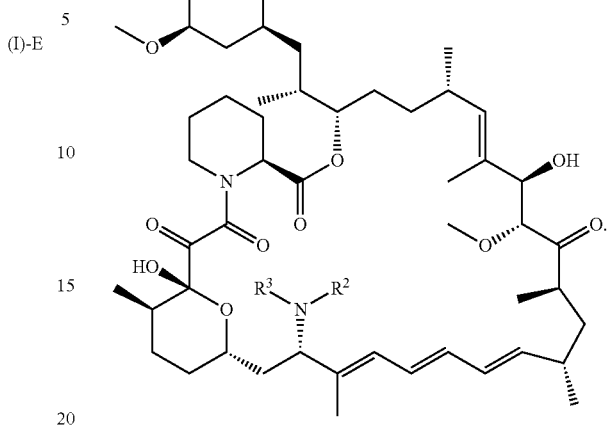
12. The compound of claim 1 or a pharmaceutically acceptable salt thereof, wherein the compound is selected from:
| Compound | Structure |
|---|---|
| 1 | 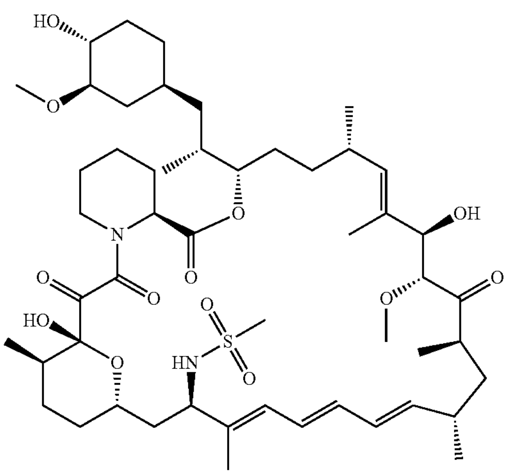 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@H]1O] |
| 2 | 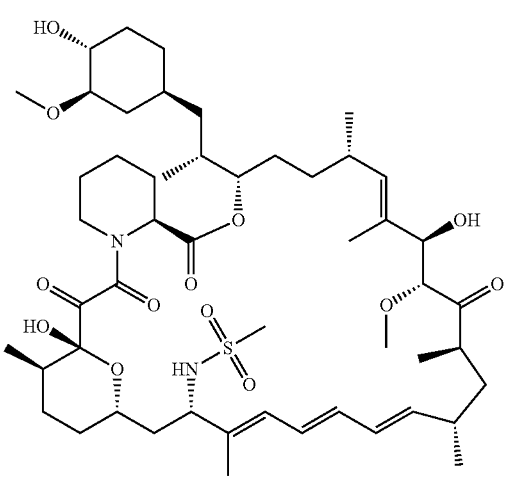 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@H]1O] |

| Compound | Structure |
|---|---|
| 3 | *(chemical structure)* |
| 4 | *(chemical structure)* |
| 5 | *(chemical structure)* |

-continued
| Compound | Structure |
|---|---|
| 6 | 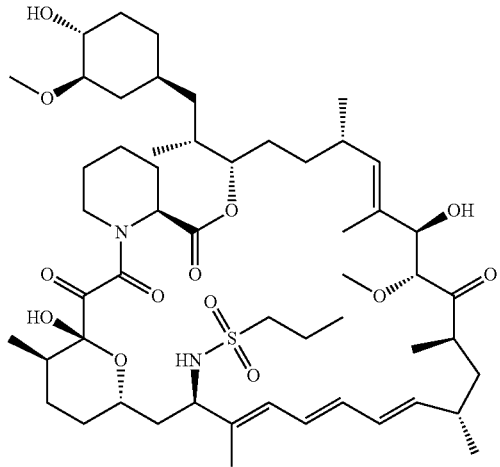 [SMILES: CCCS(=O)(=O)N[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |
| 7 | 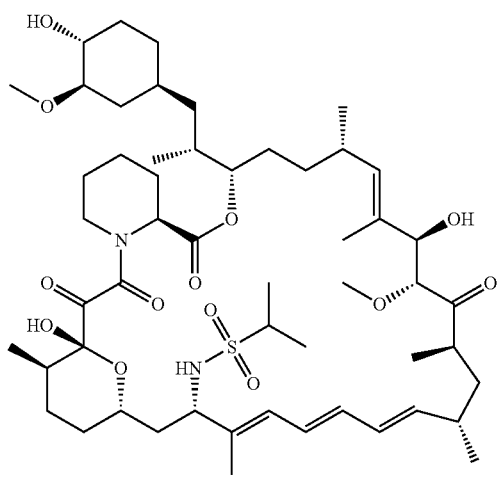 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C(C)C)C[C@@H]3CC[C@@H](C)[C@@](O)(O3)C(=O)C(=O)N3CCCC[C@H]3C(=O)O2)CC[C@H]1O] |
| 8 | 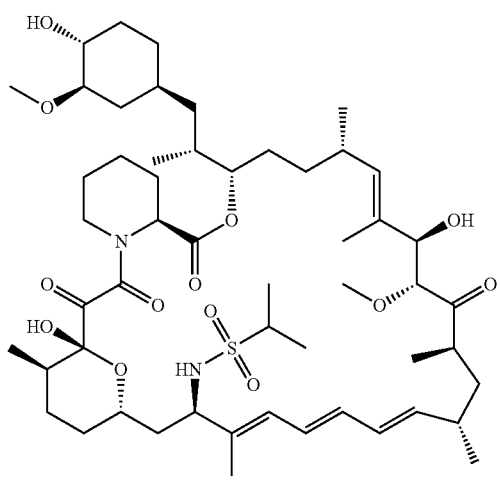 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)C(C)C)C[C@@H]3CC[C@@H](C)[C@@](O)(O3)C(=O)C(=O)N3CCCC[C@H]3C(=O)O2)CC[C@H]1O] |

-continued
| Compound | Structure |
|---|---|
| 9 | 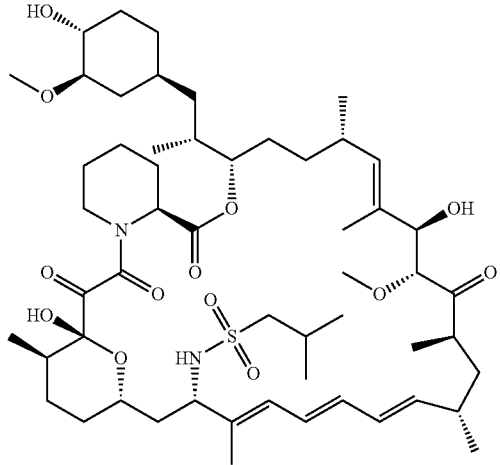 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)CC(C)C)C[C@@H]3CC[C@@H](C)[C@@](O)(O3)C(=O)C(=O)N3CCCC[C@H]3C(=O)O2)CC[C@H]1O] |
| 10 | 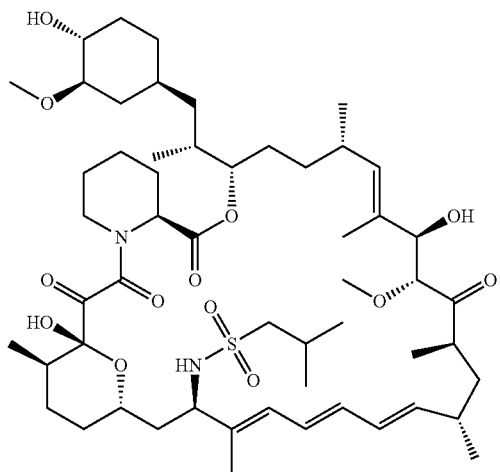 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)CC(C)C)C[C@@H]3CC[C@@H](C)[C@@](O)(O3)C(=O)C(=O)N3CCCC[C@H]3C(=O)O2)CC[C@H]1O] |
| 11 | 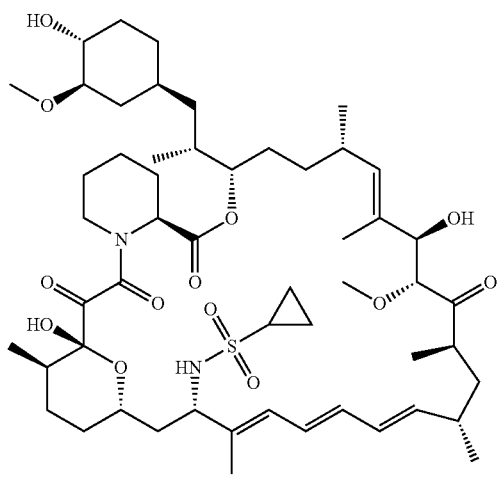 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C3CC3)C[C@@H]3CC[C@@H](C)[C@@](O)(O3)C(=O)C(=O)N3CCCC[C@H]3C(=O)O2)CC[C@H]1O] |

| Compound | Structure |
|---|---|
| 12 | (chemical structure) |
| 13 | (chemical structure) |
| 14 | (chemical structure) |

| Compound | Structure |
|---|---|
| 15 | 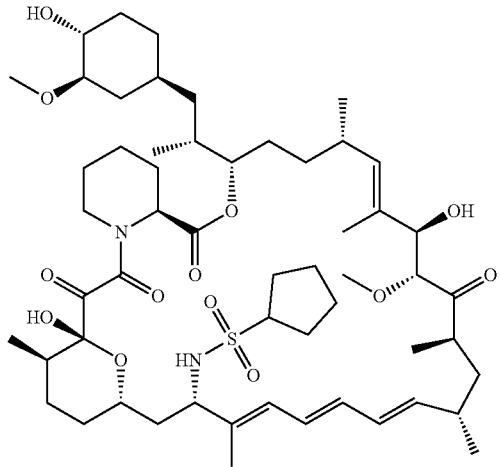 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)C3CCCC3)C[C@@H]3CC[C@@H](C)[C@@](O)(O3)C(=O)C(=O)N3CCCC[C@H]3C(=O)O2)CC[C@H]1O] |
| 16 | 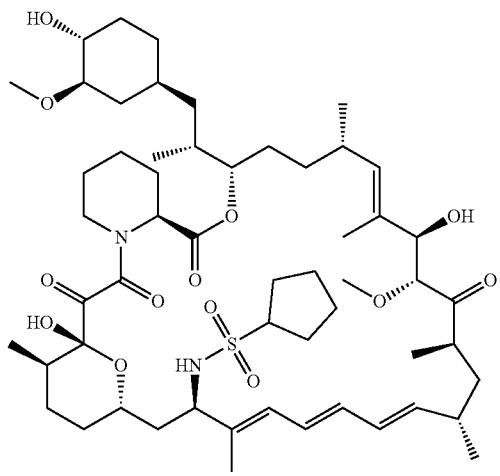 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)C3CCCC3)C[C@@H]3CC[C@@H](C)[C@@](O)(O3)C(=O)C(=O)N3CCCC[C@H]3C(=O)O2)CC[C@H]1O] |
| 17 | 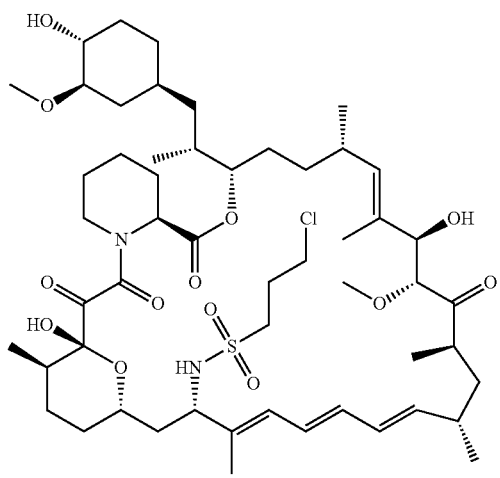 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)CCCCl)C[C@@H]3CC[C@@H](C)[C@@](O)(O3)C(=O)C(=O)N3CCCC[C@H]3C(=O)O2)CC[C@H]1O] |

| Compound | Structure |
|---|---|
| 18 | 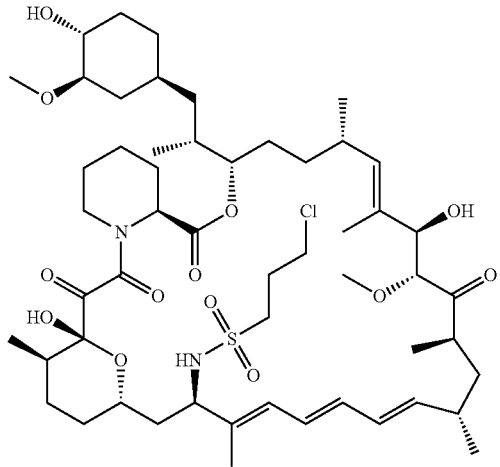 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)CCCCl)C[C@@H]3CC[C@@H](C)[C@@](O)(O3)C(=O)C(=O)N3CCCC[C@H]3C(=O)O2)CC[C@H]1O] |
| 19 | 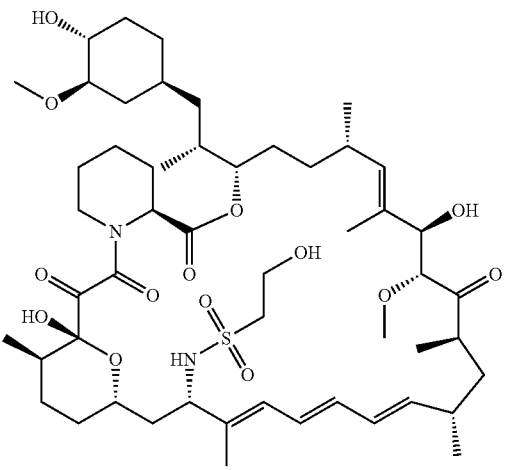 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(=O)(=O)CCO)C[C@@H]3CC[C@@H](C)[C@@](O)(O3)C(=O)C(=O)N3CCCC[C@H]3C(=O)O2)CC[C@H]1O] |
| 20 | 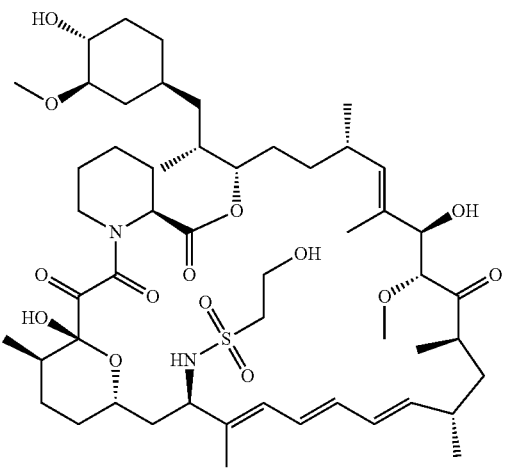 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(=O)(=O)CCO)C[C@@H]3CC[C@@H](C)[C@@](O)(O3)C(=O)C(=O)N3CCCC[C@H]3C(=O)O2)CC[C@H]1O] |

-continued

| Compound | Structure |
|---|---|
| 21 | 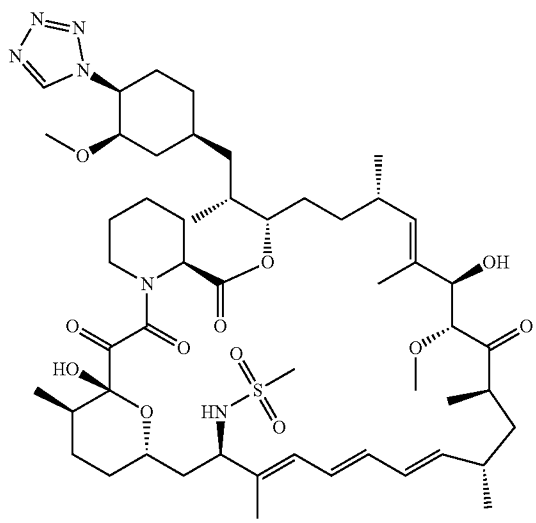 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@@H]1n1cnnn1] |
| 22 | 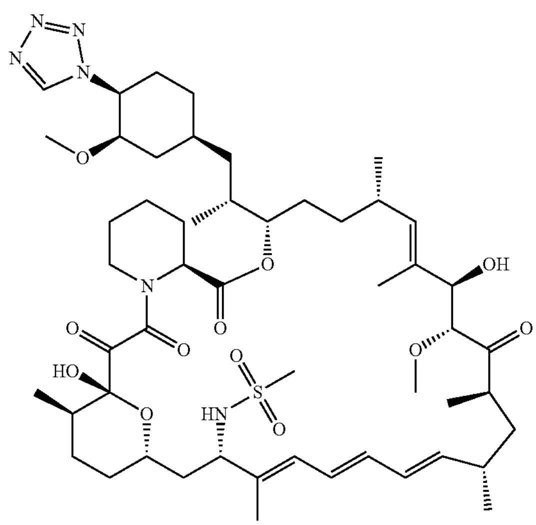 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@@H]1n1cnnn1] |
| 23 | 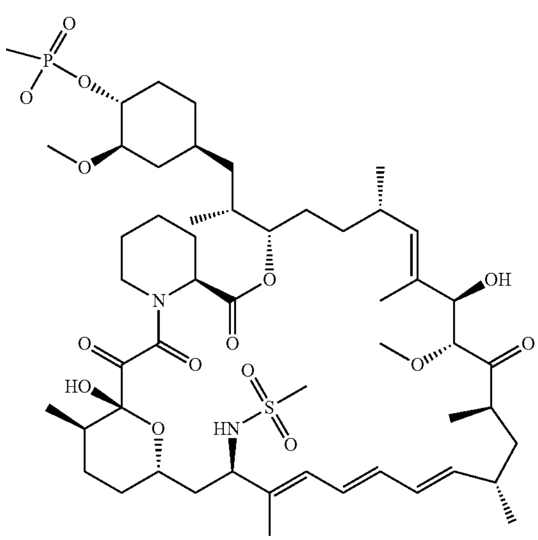 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@H]1OP(C)(=O)O] |

-continued
| Compound | Structure |
|---|---|
| 24 | 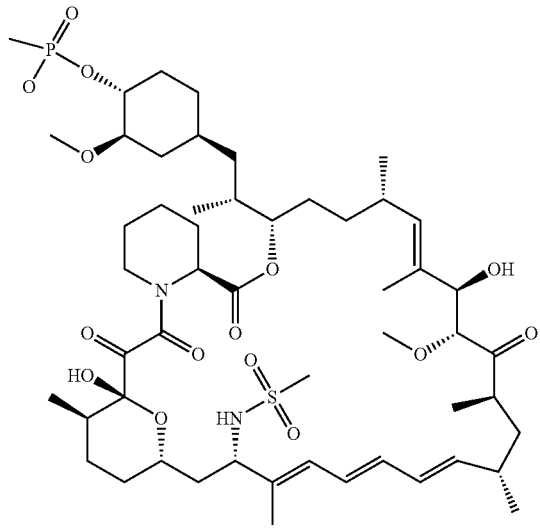 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@H]1OP(C)(=O)O] |
| 25 | 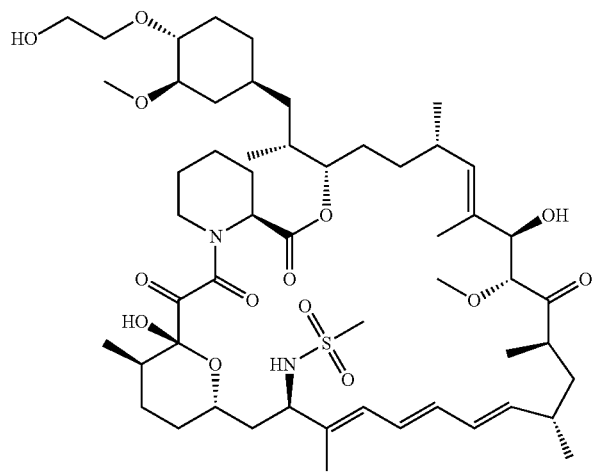 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NS(C)(=O)=O)C[C@@H]3CC[C@@H](C)[C@@](O)(O3)C(=O)C(=O)N3CCCC[C@H]3C(=O)O2)CC[C@H]1OCCO] |
| 26 | 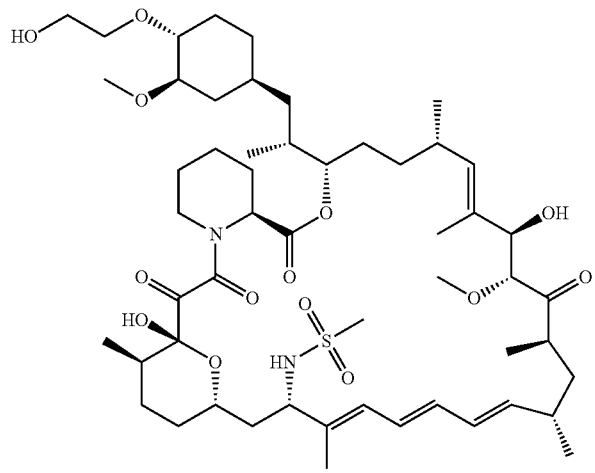 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NS(C)(=O)=O)C[C@@H]3CC[C@@H](C)[C@@](O)(O3)C(=O)C(=O)N3CCCC[C@H]3C(=O)O2)CC[C@H]1OCCO] |

-continued
| Compound | Structure |
|---|---|
| 27 | 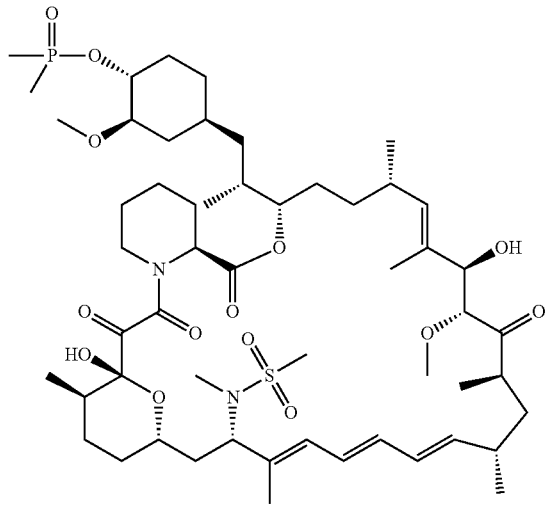 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(C)S(C)(=O)=O)C[C@@H]3CC[C@@H](C)[C@@](O)(O3)C(=O)C(=O)N3CCCC[C@H]3C(=O)O2)CC[C@H]1OP(C)(C)=O] |
| 28 | 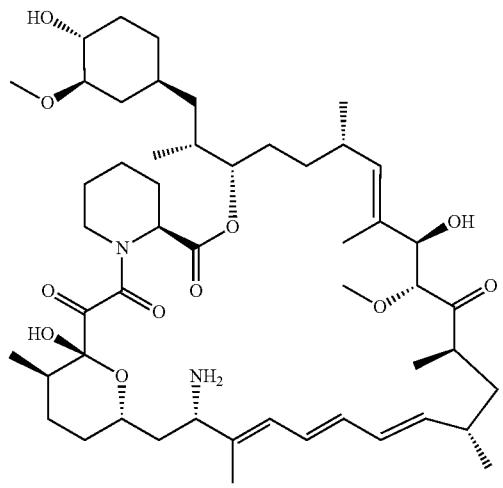 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N)C[C@@H]3CC[C@@H](C)[C@@](O)(O3)C(=O)C(=O)N3CCCC[C@H]3C(=O)O2)CC[C@H]1O] |
| 29 | 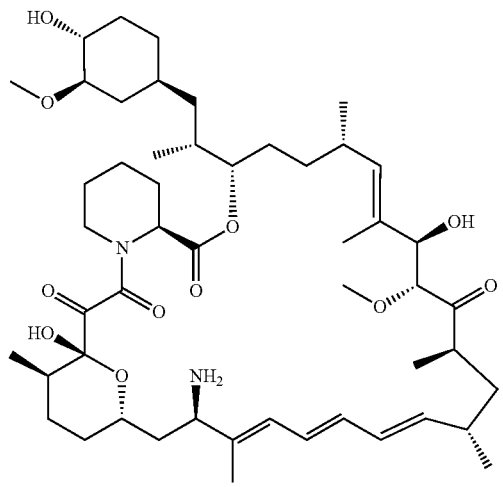 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N)C[C@@H]3CC[C@@H](C)[C@@](O)(O3)C(=O)C(=O)N3CCCC[C@H]3C(=O)O2)CC[C@H]1O] |

| Compound | Structure |
|---|---|
| 30 | 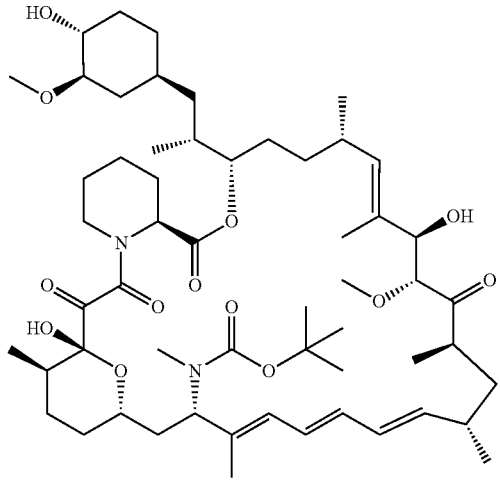 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(C)C(=O)OC(C)(C)C)C[C@@H]3CC[C@@H](C)[C@@](O)(O3)C(=O)C(=O)N3CCCC[C@H]3C(=O)O2)CC[C@H]1O] |
| 31 | 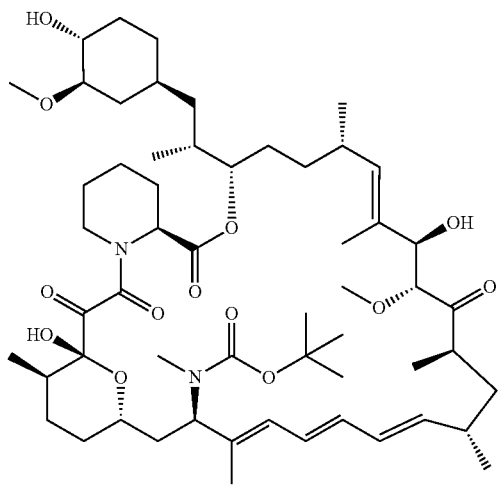 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N(C)C(=O)OC(C)(C)C)C[C@@H]3CC[C@@H](C)[C@@](O)(O3)C(=O)C(=O)N3CCCC[C@H]3C(=O)O2)CC[C@H]1O] |
| 32 | 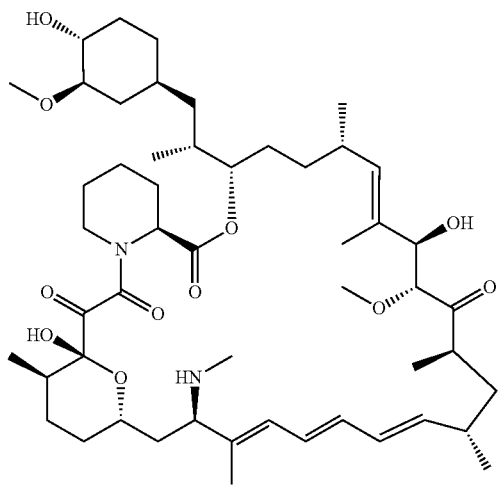 [SMILES: CN[C@@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |

| Compound | Structure |
|---|---|
| 33 | 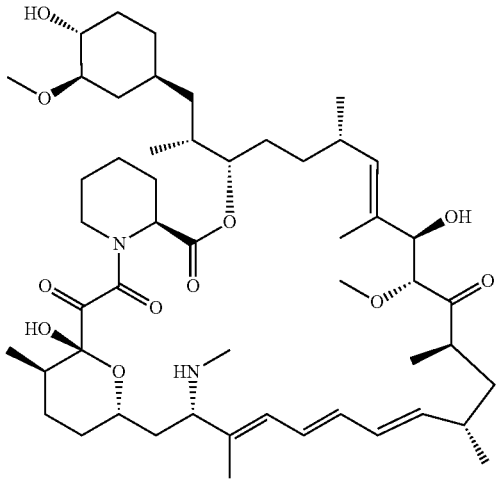 [SMILES: CN[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC[C@H](C)/C=C(\C)[C@@H](O)[C@@H](OC)C(=O)[C@H](C)C[C@H](C)/C=C/C=C/C=C/1C] |
| 34 | 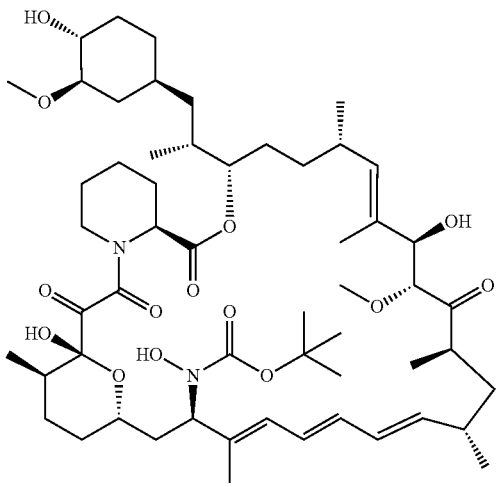 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](N(O)C(=O)OC(C)(C)C)C[C@@H]3CC[C@@H](C)[C@@](O)(O3)C(=O)C(=O)N3CCCC[C@H]3C(=O)O2)CC[C@H]1O] |
| 35 | 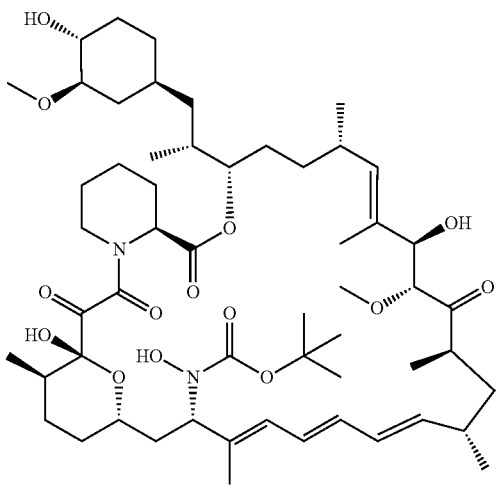 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](N(O)C(=O)OC(C)(C)C)C[C@@H]3CC[C@@H](C)[C@@](O)(O3)C(=O)C(=O)N3CCCC[C@H]3C(=O)O2)CC[C@H]1O] |

-continued
| Compound | Structure |
|---|---|
| 36 | 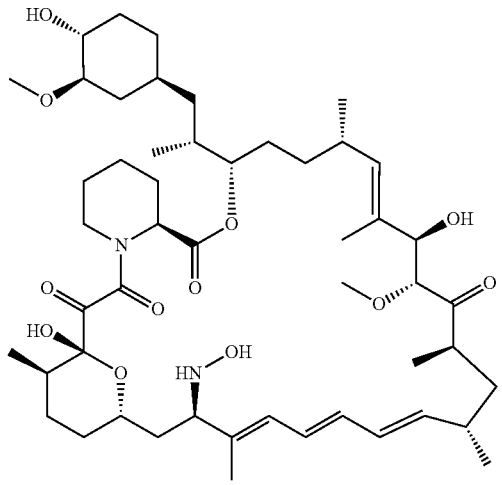 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NO)C[C@@H]3CC[C@@H](C)[C@@](O)(O3)C(=O)C(=O)N3CCCC[C@H]3C(=O)O2)CC[C@H]1O] |
| 37 | 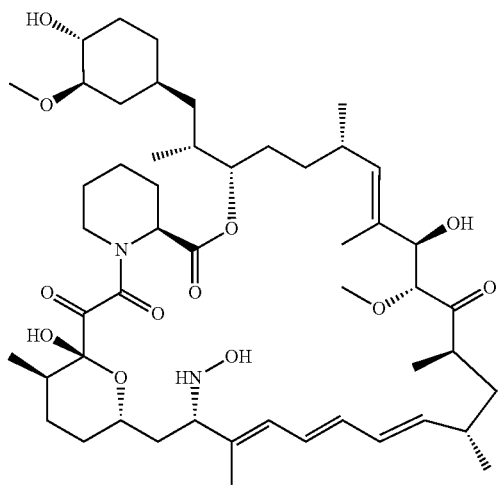 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NO)C[C@@H]3CC[C@@H](C)[C@@](O)(O3)C(=O)C(=O)N3CCCC[C@H]3C(=O)O2)CC[C@H]1O] |
| 38 | 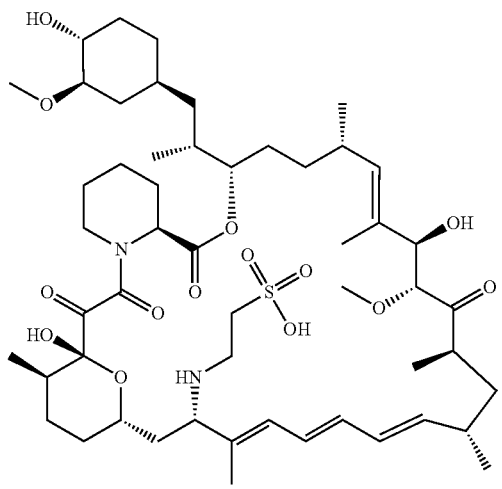 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NCCS(=O)(=O)O)C[C@@H]3CC[C@@H](C)[C@@](O)(O3)C(=O)C(=O)N3CCCC[C@H]3C(=O)O2)CC[C@H]1O] |

-continued
| Compound | Structure |
|---|---|
| 39 | 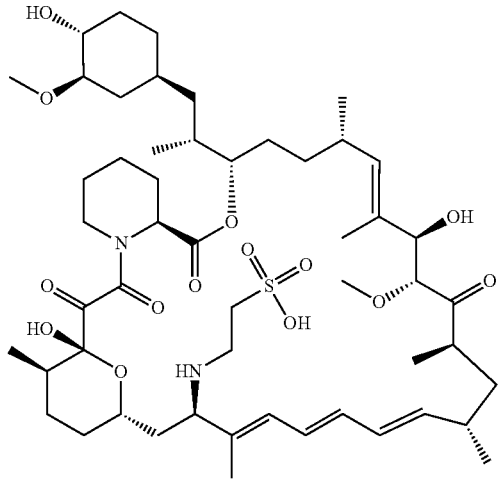 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NCCS(=O)(=O)O)C[C@@H]3CC[C@@H](C)[C@@](O)(O3)C(=O)C(=O)N3CCCC[C@H]3C(=O)O2)CC[C@H]1O] |
| 40 | 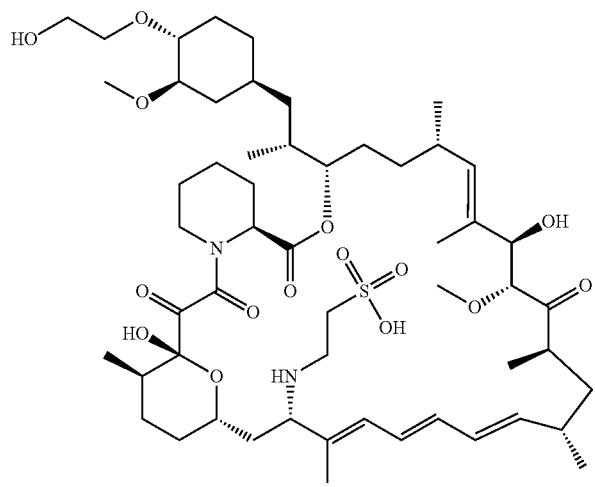 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@@H](NCCS(=O)(=O)O)C[C@@H]3CC[C@@H](C)[C@@](O)(O3)C(=O)C(=O)N3CCCC[C@H]3C(=O)O2)CC[C@H]1OCCO] |
| 41 | 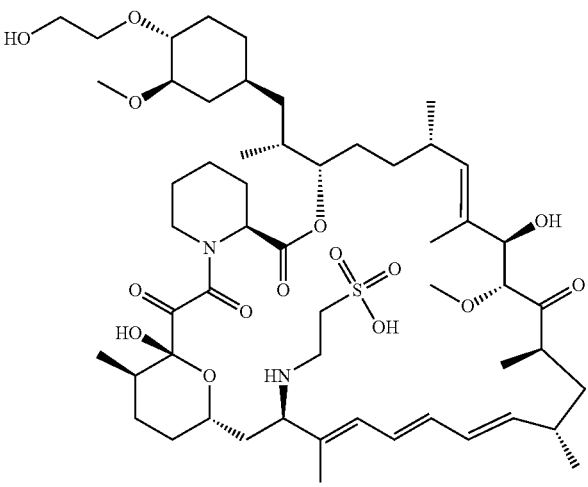 [SMILES: CO[C@@H]1C[C@H](C[C@@H](C)[C@@H]2CC[C@H](C)/C=C(\C)[C@@H](O)[C@@H](OC)C(=O)[C@H](C)C[C@H](C)/C=C/C=C/C=C(\C)[C@H](NCCS(=O)(=O)O)C[C@@H]3CC[C@@H](C)[C@@](O)(O3)C(=O)C(=O)N3CCCC[C@H]3C(=O)O2)CC[C@H]1OCCO] |

| Compound | Structure |
|---|---|
| 42 | 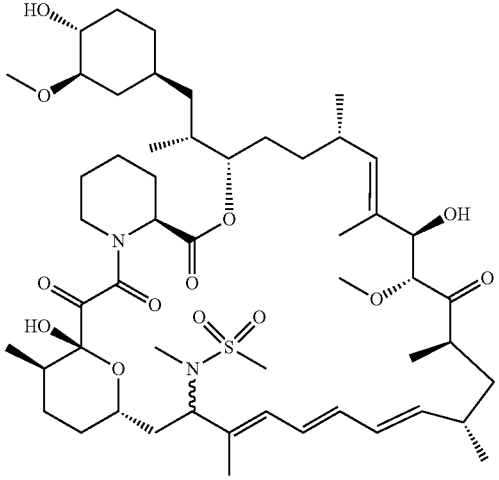 |

* Absolute sterochemistry at C16 undetermined

13. A pharmaceutical composition comprising a therapeutically effective amount of a compound of claim 1 or a pharmaceutically acceptable salt thereof and one or more pharmaceutically acceptable carriers.

14. A pharmaceutical combination comprising a therapeutically effective amount of a compound of claim 1 or a pharmaceutically acceptable salt thereof and one or more therapeutically active agents.

* * * * *